(12) United States Patent
Essigmann et al.

(10) Patent No.: US 9,283,242 B2
(45) Date of Patent: Mar. 15, 2016

(54) USES OF DIHYDRO BASES

(71) Applicant: Massachusetts Institute of Technology, Cambridge, MA (US)

(72) Inventors: John M. Essigmann, Cambridge, MA (US); Deyu Li, Cambridge, MA (US); Katherine J. Silvestre, Seekonk, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/161,675

(22) Filed: Jan. 22, 2014

(65) Prior Publication Data

US 2014/0206639 A1    Jul. 24, 2014

Related U.S. Application Data

(60) Provisional application No. 61/755,459, filed on Jan. 22, 2013.

(51) Int. Cl.
| | | |
|---|---|---|
| *A61K 31/7076* | (2006.01) | |
| *A61K 31/7068* | (2006.01) | |
| *A61K 31/708* | (2006.01) | |
| *A61K 31/7072* | (2006.01) | |
| *C07H 19/073* | (2006.01) | |
| *C07H 19/173* | (2006.01) | |

(52) U.S. Cl.
CPC ........... *A61K 31/7076* (2013.01); *A61K 31/708* (2013.01); *A61K 31/7068* (2013.01); *A61K 31/7072* (2013.01); *C07H 19/073* (2013.01); *C07H 19/173* (2013.01)

(58) Field of Classification Search
None
See application file for complete search history.

(56) References Cited

U.S. PATENT DOCUMENTS

| | | | |
|---|---|---|---|
| 3,221,010 A | 11/1965 | Duschinsky | |
| 3,462,416 A | 8/1969 | Hanze et al. | |
| 6,132,776 A | 10/2000 | Loeb et al. | |
| 7,642,247 B2 | 1/2010 | Daifuku et al. | |

FOREIGN PATENT DOCUMENTS

WO   WO2005/020885   *   3/2005

OTHER PUBLICATIONS

Pochet et al., ChemBioChem, 2003, 4(8), 742-747.*
Green et al., Journal of Biochemistry, 1957, vol. 228, pp. 601-609.*
International Search Report and Written Opinion for International Application No. PCT/US2014/012617 mailed May 7, 2014.
Matoušová et al., 2'-deoxy-5,6-dihydro-5-azacytidine—a less toxic alternative of 2'-deoxy-5-azacytidine: a comparative study of hypomethylating potential. Epigenetics. Jun. 2011;6(6):769-76. Epub Jun. 1, 2011.
PubChem CID-53761751. Create Date: Dec. 4, 2011. 3 pages.
PubChem CID-157173. Create Date: Aug. 9, 2005. 3 pages.
Baranovich et al., T-705 (favipiravir) induces lethal mutagenesis in influenza A H1N1 viruses in vitro. J Virol. Apr. 2013;87(7):3741-51. doi: 10.1128/JVI.02346-12. Epub Jan. 16, 2013.
Bonnac et al., Structure-activity relationships and design of viral mutagens and application to lethal mutagenesis. J Med Chem. Dec. 12, 2013;56(23):9403-14. doi: 10.1021/jm400653j. Epub Aug. 26, 2013.
Chen et al., Lethal mutagenesis in viruses and bacteria. Genetics. Oct. 2009;183(2):639-50. doi: 10.1534/genetics.109.106492. Epub Jul. 20, 2009.
Clay et al., Safety, Tolerability, and Pharmacokinetics of KP-1461 in Phase I Clinical Studies: A Single Oral Dose Study in Non-HIV-Infected Adults, and a 14-Day Dose-Escalating Study in Highly Antiretroviral-Experienced HIV-Infected Adults. J Int Assoc Physicians AIDS Care (Chic). Jul.-Aug. 2011;10(4):232-8. doi: 10.1177/1545109711406442. Epub May 18, 2011.
Clouser et al., Exploiting drug repositioning for discovery of a novel HIV combination therapy. J Virol. Sep. 2010;84(18):9301-9. doi: 10.1128/JVI.01006-10. Epub Jul. 7, 2010.
Crotty et al., Ribavirin's antiviral mechanism of action: lethal mutagenesis? J Mol Med (Berl). Feb. 2002;80(2):86-95. Epub Dec. 4, 2001.
Crotty et al., The broad-spectrum antiviral ribonucleoside ribavirin is an RNA virus mutagen. Nat Med. Dec. 2000;6(12):1375-9.
De La Torre, Arenavirus extinction through lethal mutagenesis. Virus Res. Feb. 2005;107(2):207-14.
Delaney et al., Assays for determining lesion bypass efficiency and mutagenicity of site-specific DNA lesions in vivo. Methods Enzymol. 2006;408:1-15.

(Continued)

*Primary Examiner* — Traviss C McIntosh, III
(74) *Attorney, Agent, or Firm* — Wolf, Greenfield & Sacks, P.C.

(57) ABSTRACT

The present invention provides pharmaceutical compositions comprising a dihydro base described herein (e.g., compound DHdC). The dihydro base may show multiple tautomerism and may increase mutation of an RNA and/or DNA of a virus or cancer cell. The dihydro base may be used to reduce DNA methylation (e.g., in a cancer cell). The present invention also provides kits including the inventive pharmaceutical compositions and methods of treating a viral infection (e.g., influenza, HIV infection, or hepatitis C) or cancer using the pharmaceutical compositions or kits.

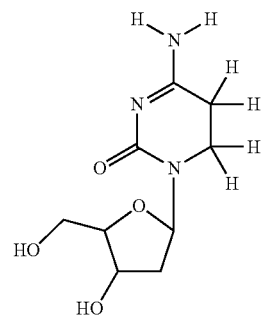

DHdC

10 Claims, 26 Drawing Sheets

(56) References Cited

OTHER PUBLICATIONS

Delaney et al., Mutagenesis, genotoxicity, and repair of 1-methyladenine, 3-alkylcytosines, 1-methylguanine, and 3-methylthymine in alkB *Escherichia coli*. Proc Natl Acad Sci U S A. Sep. 28, 2004;101(39):14051-6. Epub Sep. 20, 2004.

Dietz et al., Deep sequencing reveals mutagenic effects of ribavirin during monotherapy of hepatitis C virus genotype 1-infected patients. J Virol. Jun. 2013;87(11):6172-81. doi: 10.1128/JVI.02778-12. Epub Mar. 27, 2013.

Domingo et al., Future prospects for the treatment of rapidly evolving viral pathogens: insights from evolutionary biology. Expert Opin Biol Ther. Oct. 2008;8(10):1455-60. doi: 10.1517/14712598.8.10.1455.

Domingo et al., Viral quasispecies evolution. Microbiol Mol Biol Rev. Jun. 2012;76(2):159-216. doi: 10.1128/MMBR.05023-11.

Domingo et al., Viruses as quasispecies: biological implications. Curr Top Microbiol Immunol. 2006;299:51-82.

Eigen, Error catastrophe and antiviral strategy. Proc Natl Acad Sci U S A. Oct. 15, 2002;99(21):13374-6. Epub Oct. 7, 2002.

Elena, RNA virus genetic robustness: possible causes and some consequences. Curr Opin Virol. Oct. 2012;2(5):525-30. doi: 10.1016/j.coviro.2012.06.008. Epub Jul. 19, 2012.

Fox et al., Lethal mutagenesis: targeting the mutator phenotype in cancer. Semin Cancer Biol. Oct. 2012;20(5):353-9. doi: 10.1016/j.semcancer.2010.10.005. Epub Oct. 8, 2010.

Gandhi et al., A review comparing deoxyribonucleoside triphosphate (dNTP) concentrations in the mitochondrial and cytoplasmic compartments of normal and transformed cells. Nucleosides Nucleotides Nucleic Acids. May 2011;30(5):317-39. doi: 10.1080/15257770.2011.586955.

Graci et al., Lethal mutagenesis of picornaviruses with N—6-modified purine nucleoside analogues. Antimicrob Agents Chemother. Mar. 2008;52(3):971-9. doi: 10.1128/AAC.01056-07. Epub Jan. 7, 2008.

Graci et al., Quasispecies, error catastrophe, and the antiviral activity of ribavirin. Virology. Jul. 5, 2002;298(2):175-80.

Graci et al., Therapeutically targeting RNA viruses via lethal mutagenesis. Future Virol. Nov. 2008;3(6):553-566.

Harris et al., KP-1212/1461, a nucleoside designed for the treatment of HIV by viral mutagenesis. Antiviral Res. Jul. 2005;67(1):1-9.

Jaszczur et al., AID and Apobec3G haphazard deamination and mutational diversity. Cell Mol Life Sci. Sep. 2013;70(17):3089-108. doi: 10.1007/s00018-012-1212-1. Epub Nov. 22, 2012.

Koito et al., Intrinsic immunity against retrotransposons by APOBEC cytidine deaminases. Front Microbiol. Feb. 20, 2013;4:28. doi: 10.3389/fmicb.2013.00028. eCollection 2013.

Li et al., Tautomerism provides a molecular explanation for the mutagenic properties of the anti-HIV nucleoside 5-aza-5,6-dihydro-2'-deoxycytidine. Proc Natl Acad Sci U S A. Aug. 12, 2014;111(32):E3252-9. doi: 10.1073/pnas.1405635111. Epub Jul. 28, 2014.

Loeb et al., Lethal mutagenesis of HIV with mutagenic nucleoside analogs. Proc Natl Acad Sci U S A. Feb. 16, 1999;96(4):1492-7.

Manrubia et al., Pathways to extinction: beyond the error threshold. Philos Trans R Soc Lond B Biol Sci. Jun. 27, 2010;365(1548):1943-52. doi: 10.1098/rstb.2010.0076.

Moreno et al., Arenaviruses and lethal mutagenesis. Prospects for new ribavirin-based interventions. Viruses. Nov. 6, 2012;4(11):2786-805. doi: 10.3390/v4112786.

Mullins et al., Mutation of HIV-1 genomes in a clinical population treated with the mutagenic nucleoside KP1461. PLoS One. Jan. 14, 2011;6(1):e15135. doi: 10.1371/journal.pone.0015135.

Murakami et al., Mechanism of action of a novel viral mutagenic covert nucleotide: molecular interactions with HIV-1 reverse transcriptase and host cell DNA polymerases. Antiviral Res. Jul. 2005;67(1):10-7. Epub Jan. 26, 2005.

Ortega-Prieto et al., Extinction of hepatitis C virus by ribavirin in hepatoma cells involves lethal mutagenesis. PLoS One. Aug. 16, 2013;8(8):e71039. doi: 10.1371/journal.pone.0071039. eCollection 2013.

Perales et al., Lethal mutagenesis of viruses. Curr Opin Virol. Nov. 2011;1(5):419-22. doi: 10.1016/j.coviro.2011.09.001. Epub Oct. 4, 2011.

Rodman et al., Systemic pharmacokinetics and cellular pharmacology of zidovudine in human immunodeficiency virus type 1-infected women and newborn infants. J Infect Dis. Dec. 1999;180(6):1844-50.

Singh et al., Direct observation of multiple tautomers of oxythiamine and their recognition by the thiamine pyrophosphate riboswitch. ACS Chem Biol. Jan. 17, 2014;9(1):227-36. doi: 10.1021/cb400581f. Epub Nov. 19, 2013.

Smith et al., Lethal mutagenesis of HIV. Virus Res. Feb. 2005;107(2):215-28.

Smyth et al., The origin of genetic diversity in HIV-1. Virus Res. Nov. 2012;169(2):415-29. doi: 10.1016/j.virusres.2012.06.015. Epub Jun. 21, 2012.

Tripathi et al., Stochastic simulations suggest that HIV-1 survives close to its error threshold. PLoS Comput Biol. 2012;8(9):e1002684. doi: 10.1371/journal.pcbi.1002684. Epub Sep. 13, 2012.

Van Der Kuyl et al., The biased nucleotide composition of the HIV genome: a constant factor in a highly variable virus. Retrovirology. Nov. 6, 2012;9:92. doi: 10.1186/1742-4690-9-92.

International Preliminary Report on Patentability for International Application No. PCT/US2014/012617 mailed Aug. 6, 2015.

\* cited by examiner

Figure 13B

USES OF DIHYDRO BASES

RELATED APPLICATIONS

The present application claims priority under 35 U.S.C. §119(e) to U.S. provisional patent application, U.S. Ser. No. 61/755,459, filed Jan. 22, 2013, which is incorporated herein by reference.

GOVERNMENT SUPPORT

This invention was made with U.S. Government support under Grant Nos. CA080024 and CA026731 awarded by the U.S. National Institutes of Health. The U.S. Government has certain rights in the invention.

BACKGROUND OF THE INVENTION

A major obstacle for viral disease treatment is viral persistence, which makes many current anti-rival therapies only temporality effective. Using HIV/AIDS as an example, nucleoside/nucleotide analog reverse transcriptase (RT) inhibitors, such as AZT, are the most commonly used drugs for inhibiting HIV reception. However, drug resistance generated by HIV mutations severely reduces the efficacy of those drugs. One reason for drug resistance against these chain terminators is the evolution of the HIV RT under selective pressure by the drug.

An approach, called "lethal mutagenesis" has recently been developed (Loeb et al., *Proc. Natl. Acad. Sci. USA*, 1999, 96, 1492-1497; Mullins et al., PLoS ONE, 2011, 6, e15135; Clay et al., *Journal of the International Association of Physicians in AIDS Care*, 2011, 10, 232-238; Harris et al., *Antiviral Res.* 2005, 67, 1-9). This approach involves nucleotide analogs that can be incorporated into the HIV genome and extended (they are not chain terminators) and increase the mutation rate of HIV. When the mutation rate of HIV is over its "error catastrophe limit," the HIV will produce mostly non-viable progeny. Those nucleotide analogs are thus examples of lethal mutagens. The lethal mutagenesis approach has been shown to be safe by a drug candidate KP1212 (below) in Phase I and II clinical trials and offers the possibility of treatment of the persistent population of HIV, which would become increasingly dominated by weak or non-viable viruses.

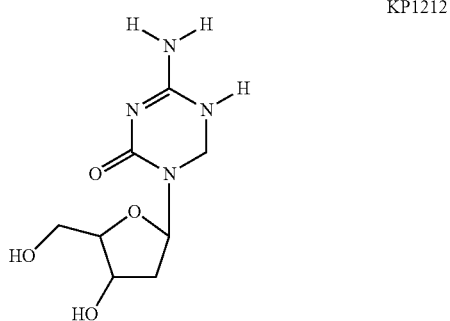 [SMILES: NC1=NC(=O)N(C2CC(O)C(CO)O2)CN1]

KP1212

SUMMARY OF THE INVENTION

The present invention provides dihydro bases (e.g., DHdC, 4,5-DHdG, 7,8-DHdG, DHdU, 4,5-DHdA, 7,8-DHdA, DHdT, 5-R-DHdT, 5-S-DHdT, DH-5-OH-dC, DH-5-halo-dC, KP1212, substituted DHdC (e.g., DH-5-OH-dC or DH-5-halo-dC), substituted 4,5-DHdG, substituted 7,8-DHdG, substituted DHdU, substituted 4,5-DHdA, substituted 7,8-DHdA, substituted DHdT, substituted 5-R-DHdT, substituted 5-S-DHdT, and substituted KP1212) (see, e.g., FIGS. 1 and 20). In certain embodiments, a dihydro base described herein is substituted DHdC (e.g., DH-5-OH-dC or DH-5-halo-dC), substituted 4,5-DHdG, substituted 7,8-DHdG, substituted DHdU, substituted 4,5-DHdA, substituted 7,8-DHdA, substituted DHdT, substituted 5-R-DHdT, substituted 5-S-DHdT, or substituted KP1212.

In another aspect, the present invention provides pharmaceutical compositions and kits including a dihydro base described herein.

The dihydro bases described herein may show multiple tautomerism and thus can increase the mutation rate of an RNA and/or DNA of a virus or cancer cell.

The dihydro bases described herein also can be useful as hypomethylating agents. These can be useful to inhibit DNA methyltransferases. This inhibition can be useful to treat cancer (e.g., alone or in combination with one or more chemotherapeutic or other cancer therapeutic agents). For example, aberrant DNA methylation and a consequent silencing of cancer-related genes are commonly found in human tumor cells (Matoušováet al., *Epigenetics* 2011, 6, 769-776). Inhibitors of DNA methyltransferases may represent a gentle therapeutic alternative to standard chemotherapy. They are incorporated into the DNA, reactivate methylated genes and protect them from re-methylation.

The present invention also provides methods of treating a viral infection (e.g., influenza, HIV infection, or hepatitis C) using the dihydro bases, pharmaceutical compositions, and kits described herein.

The present invention also provides methods of treating cancer using the dihydro bases, pharmaceutical compositions, and kits described herein. According to aspects of the disclosure, a lethal mutagenesis approach also can be used to treat cancer. Nucleotide analogs (e.g., dihydro bases described herein) can increase the mutation rate of the DNA of cancer cells (e.g., cancer cells with a mutator phenotype) to over the "error catastrophe limit" and thus show genotoxicity and/or mitochondrial toxicity against the cancer cells.

The present invention further provides methods of preparing the dihydro bases described herein. In certain embodiments, a method of preparing a dihydro base (e.g., substituted or unsubstituted DHdC) includes hydrogenating a base (e.g., substituted or unsubstituted dC) in the presence of a catalyst (e.g., Rh/alumina) using flow chemistry.

DETAILED DESCRIPTION OF CERTAIN EMBODIMENTS OF THE INVENTION

Figure 12:
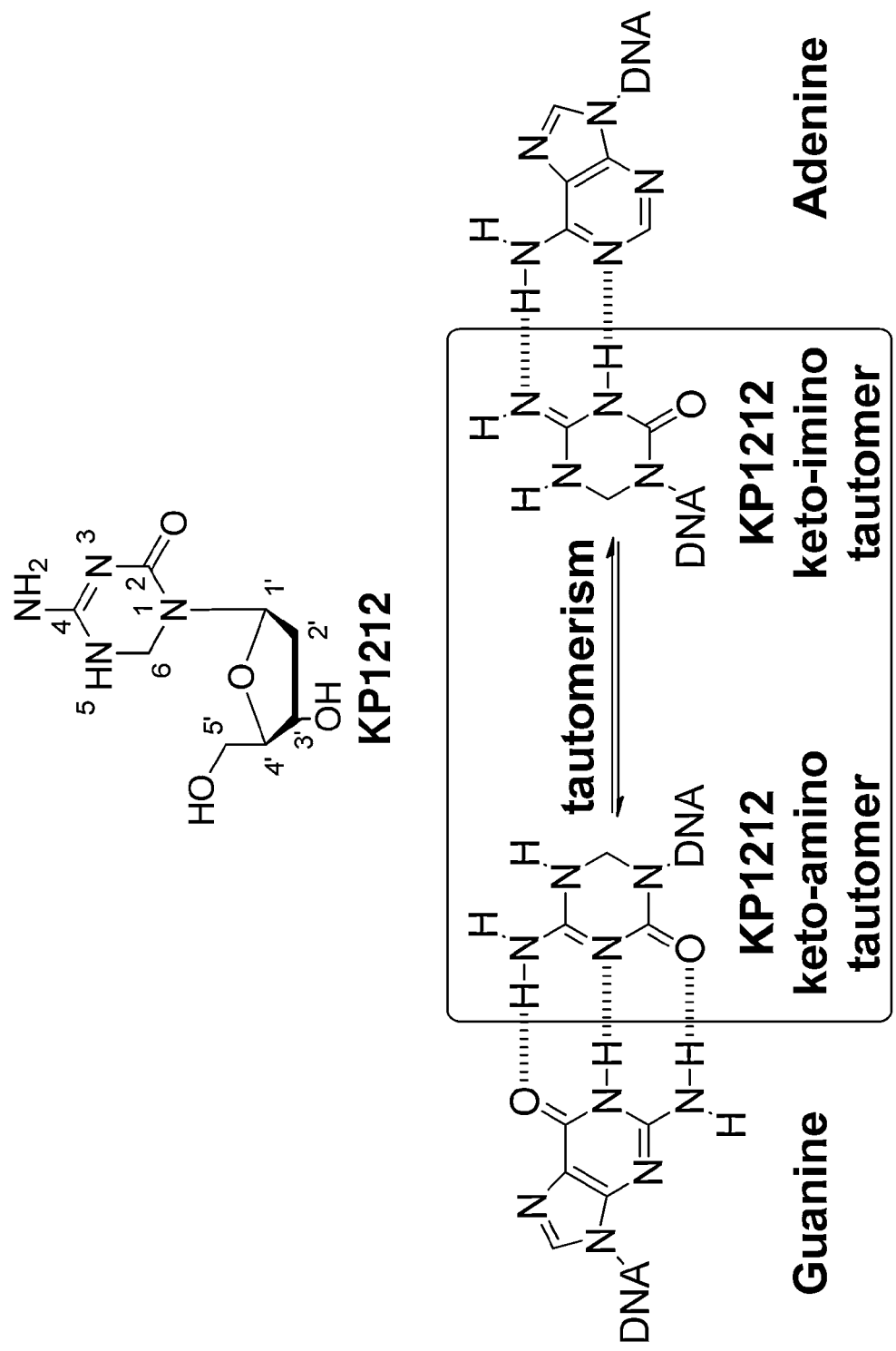
FIG. 12 shows exemplary base-pairings of exemplary tautomers of compound KP1212 with guanine and adenine.

Viral lethal mutagenesis is a strategy whereby the innate immune system or mutagenic pool nucleotides increase the error rate of viral replication above the error catastrophe limit. Lethal mutagenesis is proposed as a mechanism for several anti-viral compounds, including Ribavirin, which is useful for treating RS virus infection (RSV) and 5-aza-5,6-dihydro-2'-deoxycytidine (KP1212), a dihydro base which causes A to G and G to A mutations in HIV. NMR and infrared spectroscopy results indicate that KP1212 was shown to exist as a broad ensemble of interconverting tautomers, among which enolic forms dominated. The mutagenic properties of KP1212 were determined empirically by in vitro and in vivo replication of a single-stranded vector containing a single KP1212. It was found that KP1212 paired with both A (10%) and G (90%), which is in accord with clinical observations. A model is proposed that correlates the mutagenicity of KP1212 with its tautomeric distribution in solution. When incorporated into HIV DNA by RT, KP1212 allows DNA synthesis to continue. However, the modified base of KP1212 is able to tautomerize and base-pair alternately with guanine and adenine (FIG. 12).

In one aspect, the present invention provides pharmaceutical compositions including one or more dihydro bases (e.g., including or excluding one or more of DHdC, 4,5-DHdG, 7,8-DHdG, DHdU, 4,5-DHdA, 7,8-DHdA, DHdT, 5-R-DHdT, 5-S-DHdT, DH-5-OH-dC, DH-5-halo-dC, or KP1212), or a pharmaceutically acceptable salt, solvate, hydrate, polymorph, co-crystal, tautomer, stereoisomer, isotopically labeled derivative, or prodrug thereof, in an amount effective for increasing the mutation rate of an RNA and/or DNA of a virus or cancer cell, for treating a viral infection, for treating cancer, for inducing apoptosis of a cancer cell, or decreasing DNA methylation in a cancer cell. In certain embodiments, a dihydro base described herein is tautomeric or, in other words, shows a multiple tautomerism (e.g., being present in at least two different tautomeric forms). In certain embodiments, a dihydro base described herein shows a multiple tautomerism under physiological conditions. The present invention also provides methods of using one or more dihydro bases (e.g., including or excluding one or more of DHdC, 4,5-DHdG, 7,8-DHdG, DHdU, 4,5-DHdA, 7,8-DHdA, DHdT, 5-R-DHdT, 5-S-DHdT, DH-5-OH-dC, DH-5-halo-dC, or KP1212), or a pharmaceutically acceptable salt, solvate, hydrate, polymorph, co-crystal, tautomer, stereoisomer, isotopically labeled derivative, or prodrug thereof, for increasing the mutation rate of an RNA and/or DNA of a virus or cancer cell, for treating a viral infection, for treating cancer, for inducing apoptosis of a cancer cell, or decreasing DNA methylation in a cancer cell. The present invention further provides kits including one or more dihydro bases (e.g., including or excluding one or more of DHdC, 4,5-DHdG, 7,8-DHdG, DHdU, 4,5-DHdA, 7,8-DHdA, DHdT, 5-R-DHdT, 5-S-DHdT, DH-5-OH-dC, DH-5-halo-dC, or KP1212), or a pharmaceutically acceptable salt, solvate, hydrate, polymorph, co-crystal, tautomer, stereoisomer, isotopically labeled derivative, or prodrug thereof, or a pharmaceutical composition thereof, for use in an inventive method.

The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the dihydro bases described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of a compound (e.g., a dihydro base described herein) that are associated with a solvent, usually by a solvolysis reaction. This physical association may include hydrogen bonding. Conventional solvents include water, methanol, ethanol, acetic acid, DMSO, THF, diethyl ether, and the like. The dihydro bases described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound (e.g., a dihydro base described herein) which is associated with water. Typically, the number of the water molecules contained in a hydrate of a compound is in a definite ratio to the number of the compound molecules in the hydrate. Therefore, a hydrate of a compound may be represented, for example, by the general formula R.xH$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5H$_2$O)), and polyhydrates (x is a number greater than 1, e.g., dihydrates (R.2H$_2$O) and hexahydrates (R.6H$_2$O)).

The term "polymorph" refers to a crystalline form of a compound (e.g., a dihydro base described herein), or a salt, hydrate, or solvate thereof, in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "tautomers" or "tautomerism" refer to compounds (e.g., dihydro bases described herein) that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest. A compound shows a multiple tautomerism if the compound shows more than one tautomeric forms. A compound shows a single tautomerism if the compound shows only one tautomeric form.

It is also to be understood that compounds (e.g., dihydro bases described herein) that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N.Y., 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

Figure 1:
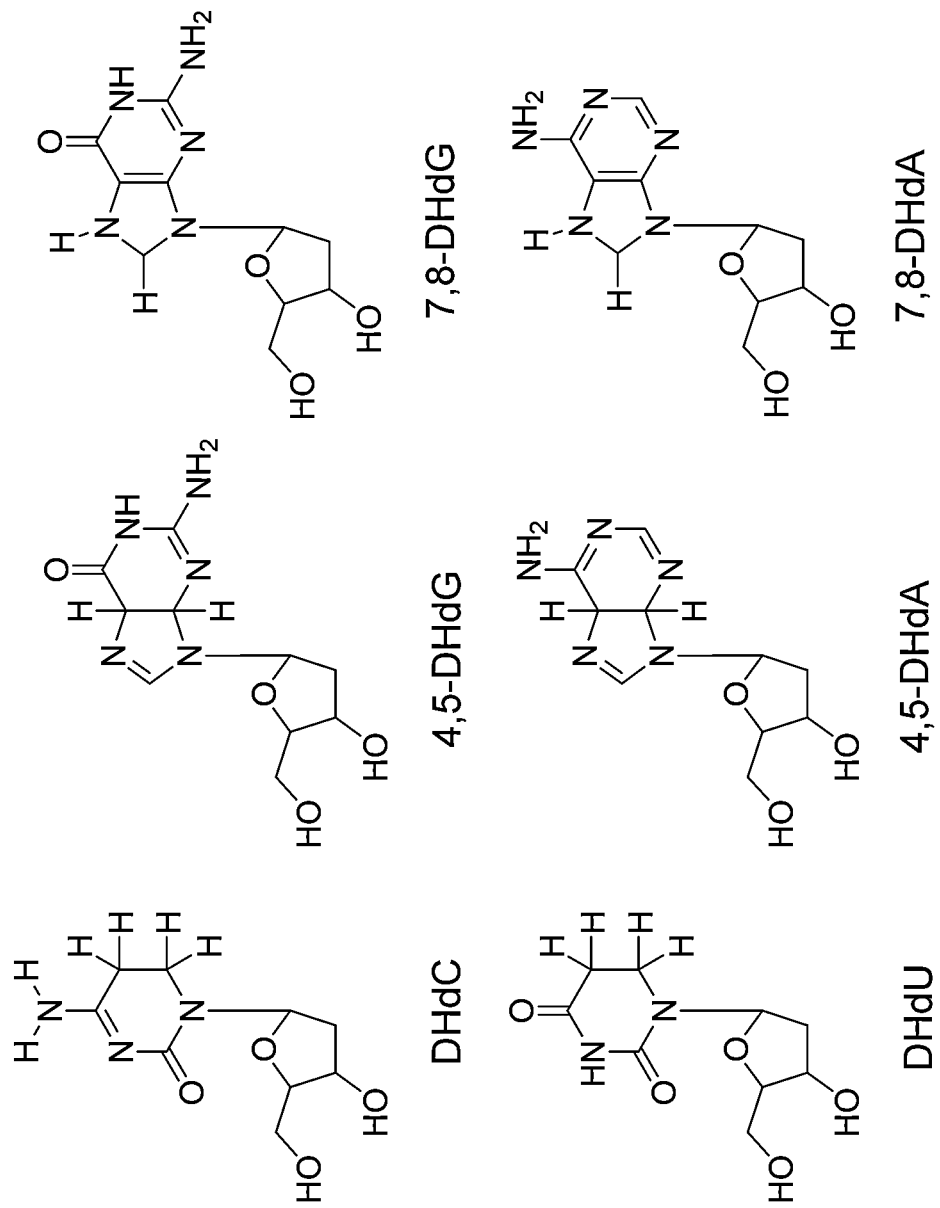
FIG. 1 shows exemplary tautomers of exemplary dihydro bases (e.g., DHdC, 4,5-DHdG, 7,8-DHdG, DHdU, 4,5-DHdA, and 7,8-DHdA).
Figure 20:
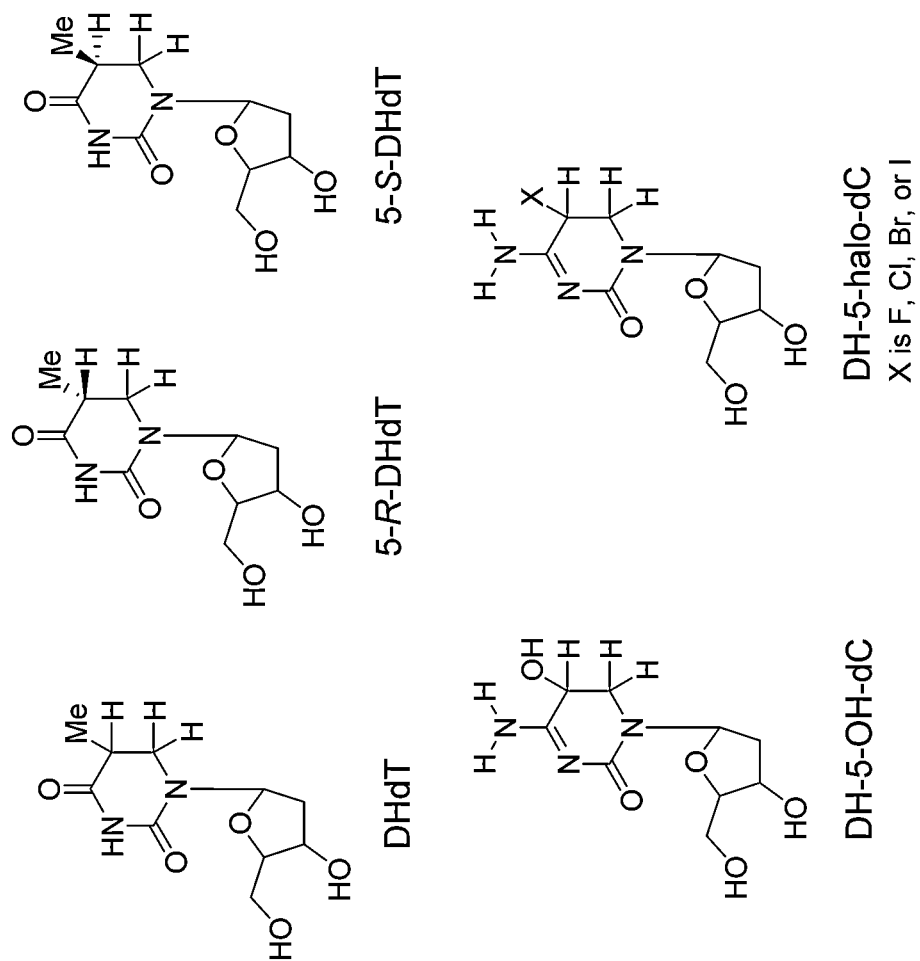
FIG. 20 shows exemplary tautomers of additional exemplary dihydro bases (e.g., DHdT, 5-R-DHdT, 5-S-DHdT, DH-5-OH-dC, and DH-5-halo-dC).

In another aspect, the present invention provides pharmaceutical compositions and kits including a dihydro base. In certain embodiments, the dihydro bases described herein are nucleoside analogs. Examples of the dihydro bases include DHdC, 4,5-DHdG, 7,8-DHdG, DHdU, 4,5-DHdA, 7,8-DHdA, and pharmaceutically acceptable salts, solvates, hydrates, polymorphs, co-crystals, tautomers, stereoisomers, isotopically labeled derivatives, and prodrugs thereof. (FIG. 1). Additional exemplary dihydro bases include DHdT, 5-R-DHdT, 5-S-DHdT, and pharmaceutically acceptable salts, solvates, hydrates, polymorphs, co-crystals, tautomers, stereoisomers, isotopically labeled derivatives, and prodrugs thereof (FIG. 20). Dihydro bases described herein also include substituted DHdC, substituted 4,5-DHdG, substituted 7,8-DHdG, substituted DHdU, substituted 4,5-DHdA, substituted 7,8-DHdA, substituted DHdT, substituted 5-R-DHdT, substituted 5-S-DHdT, substituted KP1212, and pharmaceutically acceptable salts, solvates, hydrates, polymorphs, co-crystals, tautomers, stereoisomers, isotopically labeled derivatives, and prodrugs thereof. In certain embodiments, a dihydro base described herein is substituted DHdC (e.g., DH-5-OH-dC, DH-5-halo-dC), or a pharmaceutically acceptable salt, solvate, hydrate, polymorph, co-crystal, tautomer, stereoisomer, isotopically labeled derivative, or prodrug thereof. In certain embodiments, a dihydro base described herein is not KP1212, or a pharmaceutically acceptable salt, solvate, hydrate, polymorph, co-crystal, tautomer, stereoisomer, isotopically labeled derivative, or prodrug thereof. In certain embodiments, a pharmaceutical composition of the invention includes a dihydro base described herein, or a pharmaceutically acceptable salt thereof.

In certain embodiments, a pharmaceutical composition of the invention includes DHdC, or a pharmaceutically acceptable salt, solvate, hydrate, polymorph, co-crystal, tautomer, stereoisomer, isotopically labeled derivative, or prodrug thereof, and optionally a pharmaceutically acceptable excipient. In certain embodiments, a pharmaceutical composition of the invention includes substituted DHdC (e.g., DH-5-OH-dC, DH-5-halo-dC), or a pharmaceutically acceptable salt, solvate, hydrate, polymorph, co-crystal, tautomer, stereoisomer, isotopically labeled derivative, or prodrug thereof, and optionally a pharmaceutically acceptable excipient. In certain embodiments, a pharmaceutical composition of the invention includes KP1212, or a pharmaceutically acceptable salt, solvate, hydrate, polymorph, co-crystal, tautomer, stereoisomer, isotopically labeled derivative, or prodrug thereof, and optionally a pharmaceutically acceptable excipient.

In certain embodiments, a dihydro base described herein, or a pharmaceutically acceptable salt, solvate, hydrate, polymorph, co-crystal, tautomer, stereoisomer, isotopically labeled derivative, or prodrug thereof, is provided in a pharmaceutical composition of the invention in an amount (e.g., therapeutically effective amount or prophylactic amount) effective for use in a method of the invention. In certain embodiments, a dihydro base described herein, or a pharmaceutically acceptable salt, solvate, hydrate, polymorph, co-crystal, tautomer, stereoisomer, isotopically labeled derivative, or prodrug thereof, is provided in a pharmaceutical composition of the invention in an amount effective for treating a viral infection in a subject in need thereof. In certain embodiments, a dihydro base described herein, or a pharmaceutically acceptable salt, solvate, hydrate, polymorph, co-crystal, tautomer, stereoisomer, isotopically labeled derivative, or prodrug thereof, is provided in a pharmaceutical composition of the invention in an amount effective for treating cancer in a subject in need thereof.

The exact amount of a dihydro base required to achieve an effective amount will vary from subject to subject, depending, for example, on species, age, and general condition of a subject, severity of the side effects or disorder, identity of the particular dihydro base(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a dihydro base for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a dihydro base per unit dosage form.

In certain embodiments, a dihydro base described herein may be administered at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

In some embodiments, a dihydro base described herein is administered one or more times per day, for multiple days. In some embodiments, the dosing regimen is continued for days, weeks, months, or years.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

In general, the term "substituted", whether preceded by the term "optionally" or not, means that at least one hydrogen present on a group (e.g., a carbon, oxygen, or nitrogen atom) is replaced with a permissible substituent, e.g., a substituent which upon substitution results in a stable compound (e.g., a dihydro base), e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

In certain embodiments, the substituents are independently a carbon atom substituent when attached to a carbon atom, an oxygen atom substituent when attached to an oxygen atom, or a nitrogen atom substituent when attached to a nitrogen atom.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)+X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —OC$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$alkyl)$_2$, —OC(=O)NH(C$_{1-6}$alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$ (C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$alkyl), —P(=O)(C$_{1-6}$alkyl)$_2$, —OP(=O)(C$_{1-6}$alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

In certain embodiments, a carbon atom substituent is halogen, unsubstituted C$_{1-6}$ alkyl, C$_{1-6}$ alkyl substituted with at least one halogen, —CN, —OH, —O(unsubstituted C$_{1-6}$ alkyl or C$_{1-6}$ alkyl substituted with at least one halogen), —NH$_2$, —NH(unsubstituted C$_{1-6}$ alkyl or C$_{1-6}$ alkyl substituted with at least one halogen), —N(unsubstituted C$_{1-6}$ alkyl or C$_{1-6}$ alkyl substituted with at least one halogen)$_2$, —COOH, or —CONH$_2$. In certain embodiments, a carbon atom substituent is halogen, unsubstituted C$_{1-6}$ alkyl, C$_{1-6}$ alkyl substituted with at least one halogen, or —OH.

Exemplary oxygen atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. In certain embodiments, the oxygen protecting group is silyl, TBDPS, TBDMS, TIPS, TES, TMS, MOM, THP, t-Bu, Bn, allyl, acetyl, pivaloyl, or benzoyl. In certain embodiments, an oxygen atom substituent is unsubstituted C$_{1-6}$ alkyl, C$_{1-6}$ alkyl substituted with at least one halogen, silyl, TBDPS, TBDMS, TIPS, TES, TMS, MOM, THP, t-Bu, Bn, allyl, acetyl, pivaloyl, or benzoyl. In certain embodiments, an oxygen atom substituent is unsubstituted C$_{1-6}$ alkyl or C$_{1-6}$ alkyl substituted with at least one halogen.

Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$ R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined herein. In certain embodiments, the substituent present on a nitrogen atom is a nitrogen protecting group (also referred to as an amino protecting group). In certain embodiments, the nitrogen protecting group is Bn, Boc, Cbz, Fmoc, trifluoroacetyl, triphenylmethyl, acetyl, or Ts. In certain embodiments, a nitrogen atom substituent is unsubstituted C$_{1-6}$ alkyl, C$_{1-6}$ alkyl substituted with at least one halogen, Bn, Boc, Cbz, Fmoc, trifluoroacetyl, triphenylmethyl, acetyl, or Ts. In certain embodiments, a nitrogen atom substituent is unsubstituted C$_{1-6}$ alkyl or C$_{1-6}$ alkyl substituted with at least one halogen.

"Halo" or "halogen" refers to fluorine (fluoro, F), chlorine (chloro, Cl), bromine (bromo, Br), or iodine (iodo, I).

"Alkyl" refers to a radical of a straight-chain or branched saturated hydrocarbon group having from 1 to 20 carbon atoms ("C$_{1-20}$ alkyl"). In some embodiments, an alkyl group has 1 to 10 carbon atoms ("C$_{1-10}$ alkyl"). In some embodiments, an alkyl group has 1 to 9 carbon atoms ("C$_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Haloalkyl" is alkyl substituted with at least one halogen atom. "Perhaloalkyl" is haloalkyl that includes no hydrogen atoms.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 p electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 p electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group) if not otherwise provided explicitly. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

In certain embodiments, a dihydro base described herein is substituted DHdC, substituted 4,5-DHdG, substituted 7,8-DHdG, substituted DHdU, substituted 4,5-DHdA, substituted 7,8-DHdA, substituted DHdT, substituted 5-R-DHdT, substituted 5-S-DHdT, substituted DH-5-OH-dC, substituted DH-5-halo-dC, or a pharmaceutically acceptable salt, solvate, hydrate, polymorph, co-crystal, tautomer, stereoisomer, isotopically labeled derivative, or prodrug thereof. In certain embodiments, a dihydro base described herein is substituted DHdC (e.g., 5-substituted DHdC, 6-substituted DHdC, or 5,6-disubstituted DHdC), or a pharmaceutically acceptable salt, solvate, hydrate, polymorph, co-crystal, tautomer, stereoisomer, isotopically labeled derivative, or prodrug thereof. In certain embodiments, a dihydro base described herein is 5-substituted DHdC of Formula (I-1), 6-substituted DHdC of Formula (I-2), or 5,6-disubstituted DHdC of Formula (I-3):

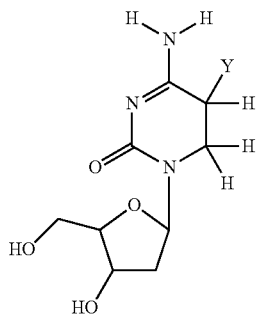
(I-1)

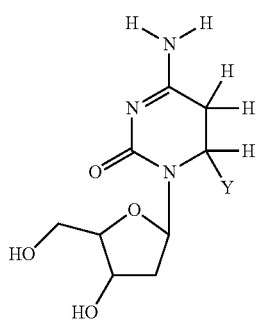
(I-2)

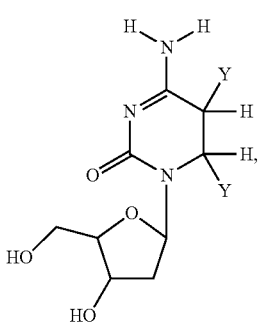
(I-3)

or a pharmaceutically acceptable salt, solvate, hydrate, polymorph, co-crystal, tautomer, stereoisomer, isotopically labeled derivative, or prodrug thereof, wherein each instance of Y is independently a non-hydrogen atom or group, such as a carbon atom substituent described herein (e.g., halogen, unsubstituted $C_{1-6}$ alkyl, $C_{1-6}$ alkyl substituted with at least one halogen, —CN, —OH, —O(unsubstituted $C_{1-6}$ alkyl or $C_{1-6}$ alkyl substituted with at least one halogen), —NH$_2$, —NH(unsubstituted $C_{1-6}$ alkyl or $C_{1-6}$ alkyl substituted with at least one halogen), —N(unsubstituted $C_{1-6}$ alkyl or $C_{1-6}$ alkyl substituted with at least one halogen)$_2$, —COOH, or —CONH$_2$). In certain embodiments, each instance of Y is independently halogen or —OH. In certain embodiments, a dihydro base described herein is substituted DHdC, or a pharmaceutically acceptable salt, tautomer, or stereoisomer thereof. In certain embodiments, a dihydro base described herein is DH-5-OH-dC (e.g., DH-5-(R)—OH-dC or DH-5-(S)—OH-dC, or a mixture thereof), or a pharmaceutically acceptable salt, solvate, hydrate, polymorph, co-crystal, tautomer, stereoisomer, isotopically labeled derivative, or prodrug thereof. In certain embodiments, a dihydro base described herein is DH-5-halo-dC (e.g., DH-5-(R)-halo-dC or DH-5-(S)-halo-dC, or a mixture thereof), or a pharmaceutically acceptable salt, solvate, hydrate, polymorph, co-crystal, tautomer, stereoisomer, isotopically labeled derivative, or prodrug thereof. In certain embodiments, a dihydro base described herein is DH-5-F-dC ((e.g., DH-5-(R)—F-dC or DH-5-(S)—F-dC, or a mixture thereof), or a pharmaceutically acceptable salt, solvate, hydrate, polymorph, co-crystal, tautomer, stereoisomer, isotopically labeled derivative, or prodrug thereof. In certain embodiments, a dihydro base described herein is DH-5-Cl-dC (e.g., DH-5-(R)—Cl-dC or DH-5-(S)—Cl-dC, or a mixture thereof), or a pharmaceutically acceptable salt, solvate, hydrate, polymorph, co-crystal, tautomer, stereoisomer, isotopically labeled derivative, or prodrug thereof. In certain embodiments, a dihydro base described herein is DH-5-Br-dC (e.g., DH-5-(R)—Br-dC or DH-5-(S)—Br-dC, or a mixture thereof), or a pharmaceutically acceptable salt, solvate, hydrate, polymorph, co-crystal, tautomer, stereoisomer, isotopically labeled derivative, or prodrug thereof. In certain embodiments, a dihydro base described herein is DH-5-I-dC (e.g., DH-5-(R)—I-dC or DH-5-(S)—I-dC, or a mixture thereof), or a pharmaceutically acceptable salt, solvate, hydrate, polymorph, co-crystal, tautomer, stereoisomer, isotopically labeled derivative, or prodrug thereof. In certain embodiments, a dihydro base described herein is DH-5-NH$_2$-dC, DH-5-Me-dC, DH-6-OH-dC, DH-6-halo-dC, DH-6-NH$_2$-dC, DH-6-Me-dC or a pharmaceutically acceptable salt, solvate, hydrate, polymorph, co-crystal, tautomer, stereoisomer, isotopically labeled derivative, or prodrug thereof.

DH-5-NH$_2$-dC

DH-5-Me-dC

DH-6-OH-dC

X is F, Cl, Br, or I
DH-6-halo-dC

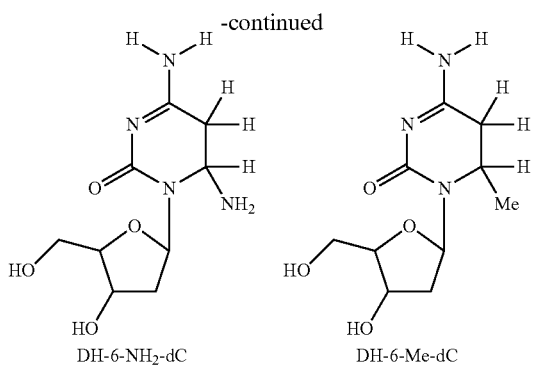

DH-6-NH₂-dC      DH-6-Me-dC

In certain embodiments, a dihydro base described herein is substituted DHdU (e.g., 5-substituted DHdU, 6-substituted DHdU, or 5,6-disubstituted DHdU), or a pharmaceutically acceptable salt, solvate, hydrate, polymorph, co-crystal, tautomer, stereoisomer, isotopically labeled derivative, or prodrug thereof. In certain embodiments, a dihydro base described herein is 5-substituted DHdU of Formula (II-1), 6-substituted DHdU of Formula (II-2), or 5,6-disubstituted DHdU of Formula (II-3):

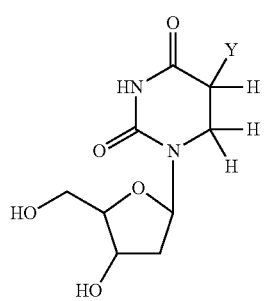

(II-1)

(II-2)

(II-3)

or a pharmaceutically acceptable salt, solvate, hydrate, polymorph, co-crystal, tautomer, stereoisomer, isotopically labeled derivative, or prodrug thereof, wherein Y is as described herein. In certain embodiments, a dihydro base described herein is DH-5-OH-dU, DH-5-halo-dU, DH-5-NH₂-dU, DH-6-OH-dU, DH-6-halo-dU, DH-6-NH₂-dU, DH-6-Me-dU, or a pharmaceutically acceptable salt, solvate, hydrate, polymorph, co-crystal, tautomer, stereoisomer, isotopically labeled derivative, or prodrug thereof.

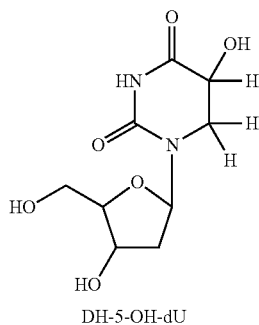

DH-5-OH-dU

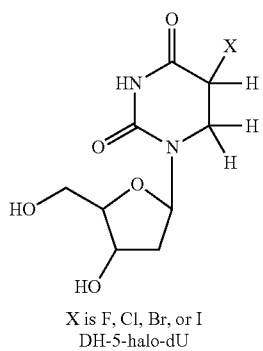

X is F, Cl, Br, or I
DH-5-halo-dU

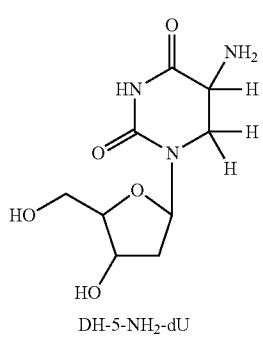

DH-5-NH₂-dU

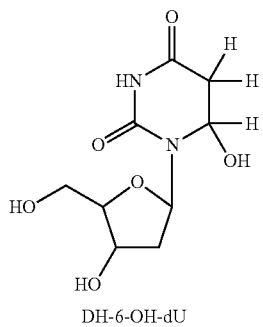

DH-6-OH-dU

-continued

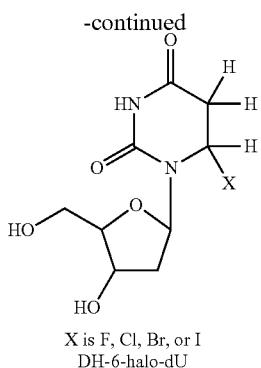

X is F, Cl, Br, or I
DH-6-halo-dU

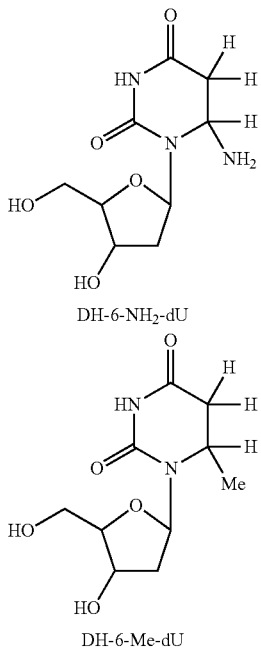

DH-6-NH₂-dU

DH-6-Me-dU

In certain embodiments, a dihydro base described herein is substituted DHdT (e.g., 6-substituted DHdT), or a pharmaceutically acceptable salt, solvate, hydrate, polymorph, co-crystal, tautomer, stereoisomer, isotopically labeled derivative, or prodrug thereof. In certain embodiments, a dihydro base described herein is 6-substituted DHdT of Formula (III-1):

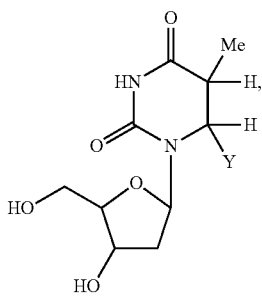

(III-1)

or a pharmaceutically acceptable salt, solvate, hydrate, polymorph, co-crystal, tautomer, stereoisomer, isotopically labeled derivative, or prodrug thereof, wherein Y is as described herein. In certain embodiments, a dihydro base described herein is DH-6-OH-dT, DH-6-halo-dT, DH-6-NH₂-dT, DH-6-Me-dT, or a pharmaceutically acceptable salt, solvate, hydrate, polymorph, co-crystal, tautomer, stereoisomer, isotopically labeled derivative, or prodrug thereof.

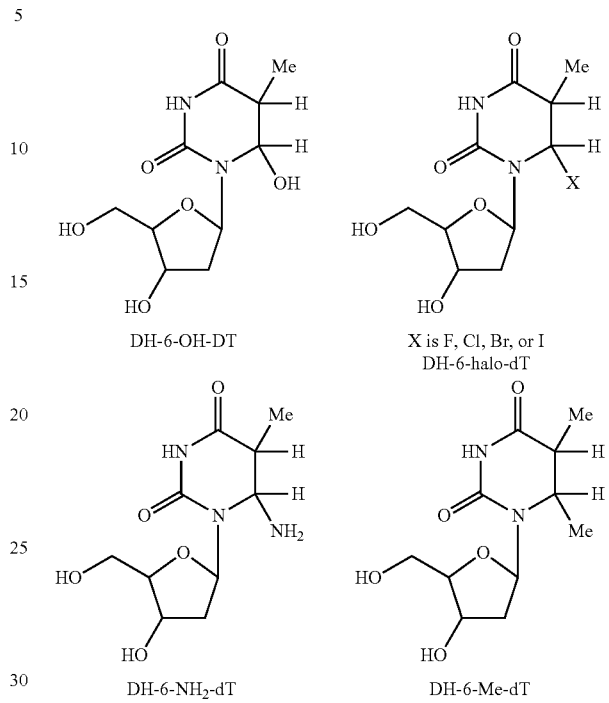

DH-6-OH-DT

X is F, Cl, Br, or I
DH-6-halo-dT

DH-6-NH₂-dT

DH-6-Me-dT

In certain embodiments, a dihydro base described herein is substituted KP1212, or a pharmaceutically acceptable salt, solvate, hydrate, polymorph, co-crystal, tautomer, stereoisomer, isotopically labeled derivative, or prodrug thereof. In certain embodiments, a dihydro base described herein is not substituted KP1212, or a pharmaceutically acceptable salt, solvate, hydrate, polymorph, co-crystal, tautomer, stereoisomer, isotopically labeled derivative, or prodrug thereof.

In certain embodiments, the dihydro bases show a multiple tautomerism. The dihydro bases described herein (e.g., DHdC) may show multiple tautomerism and may be useful lethal mutagens. The dihydro bases may be structurally similar to natural nucleosides, and different tautomeric forms of the dihydro bases may cause different responses by the genome of a virus or cancer cell. Therefore, the mutation rate of the genome (e.g., RNA and/or DNA) of the virus or cancer cell may be increased. In other words, the dihydro bases may be mutagenic and may induce mutagenesis. For example, the dihydro bases may be taken up by a virus-infected cell or a cancer cell as a nucleoside and be phosphorylated by cellular kinases to the corresponding deoxynucleoside triphosphate(s). These can induce mutagenesis.

Many viruses exhibit a high mutation rate when replicating their genomes, enabling quick adaptation to both changing cellular environments and therapeutics (Frenkel, L. M. et al. Multiple viral genetic analyses detect low-level human immunodeficiency virus type 1 replication during effective highly active antiretroviral therapy. J. Virol. 77, 5721-5730 (2003); Mullins, J. I. & Jensen, M. A. Evolutionary dynamics of HIV-1 and the control of AIDS. Curr. Top. Microbiol. Immunol. 299, 171-192 (2006); Johnston, R. HW cure: controversy, consensus, and a consortium. AIDS Res. Hum. Retroviruses 26, 943-946 (2010); Esté, J. A. & Cihlar, T. Current status and challenges of antiretroviral research and therapy. Antiviral Res. 85, 25-33 (2010); Broder, S. The development of antiretroviral therapy and its impact on the HIV-1/AIDS pandemic. Antiviral Res. 85, 1-18 (2010)). Mammalian innate immune systems have developed a mechanism to exploit this high mutation rate against the virus; in a phenomenon termed "lethal mutagenesis," (Eigen, M. Error catastrophe and antiviral strategy. Proc. Natl. Acad. Sci. U.S.A. 99, 13374-13376 (2002); Loeb, L. A. et al. Lethal mutagenesis of HIV with mutagenic nucleoside analogs. Proc. Natl. Acad. Sci. U.S.A. 96, 1492-1497 (1999); Smith, R. A., Loeb, L. A. & Preston, B. D. Lethal mutagenesis of HIV. Virus Res. 107, 215-228 (2005); Clouser, C. L., Patterson, S. E. & Mansky, L. M. Exploiting drug repositioning for discovery of a novel HIV combination therapy. J. Virol. 84, 9301-9309 (2010); Graci, J. D. & Cameron, C. E. Therapeutically targeting RNA viruses via lethal mutagenesis. Future Virol. 3, 553-566 (2008); Perales, C., Martín, V. & Domingo, E. Lethal mutagenesis of viruses. Curr. Opin. Virol. 1, 419-422 (2011); Elena, S. F. RNA virus genetic robustness: possible causes and some consequences. Curr. Opin. Virol. 2, 525-530 (2012); De la Torre, J. C. Arenavirus extinction through lethal mutagenesis. Virus Res. 107, 207-214 (2005); Bonnac, L. F., Mansky, L. M. & Patterson, S. E. Structure-activity relationships and design of viral mutagens and application to lethal mutagenesis. J. Med. Chem. (in press) (2013)), the immune system employs nucleic acid-modifying enzymes (e.g., APOBEC and ADAR) to increase the viral mutation rate sharply, stressing the functional gene product repertoire of the virus to the point that the viral population collapses (Koito, A. & Ikeda, T. Intrinsic immunity against retrotransposons by APOBEC cytidine deaminases. Front Microbiol. 4, 28 (2013); Jaszczur, M., Bertram, J. G., Pham, P., Scharff, M. D. & Goodman, M. F. AID and Apobec3G haphazard deamination and mutational diversity. Cell. Mol. Life Sci. 70, 3089-3108 (2013); Smyth, R. P., Davenport, M. P. & Mak, J. The origin of genetic diversity in HIV-1. Virus Res. 169, 415-429 (2012)). Several antiviral agents are proposed to work at least in part by a chemical version of lethal mutagenesis (e.g., ribavirin against hepatitis C virus (Ortega-Prieto, A. M. et al. Extinction of hepatitis C virus by ribavirin in hepatoma cells involves lethal mutagenesis. PLoS ONE 8, e71039 (2013); Dietz, J. et al. Deep sequencing reveals mutagenic effects of ribavirin during monotherapy of hepatitis C virus genotype 1-infected patients. J. Virol. 87, 6172-6181 (2013); Moreno, H., Grande-Pérez, A., Domingo, E. & Martín, V. Arenaviruses and lethal mutagenesis. Prospects for new ribavirin-based interventions. Viruses 4, 2786-2805 (2012); Graci, J. D. & Cameron, C. E. Quasispecies, error catastrophe, and the antiviral activity of ribavirin. Virology 298, 175-180 (2002); Crotty, S. et al. The broad-spectrum antiviral ribonucleoside ribavirin is an RNA virus mutagen. Nat. Med. 6, 1375-1379 (2000)), 5-hydroxy-2'-deoxycytidine against HIV (Loeb, L. A. et al. Lethal mutagenesis of HIV with mutagenic nucleoside analogs. Proc. Natl. Acad. Sci. U.S.A. 96, 1492-1497 (1999)) and T-705 against influenza viruses (Baranovich, T. et al. T-705 (favipiravir) induces lethal mutagenesis in influenza A H1N1 viruses in vitro. J. Virol. 87, 3741-3751 (2013))). When a sufficient number of these mutagenic nucleoside analogs is incorporated into viral genomes, the analogs increase the viral mutation rate above the error catastrophe limit, the rate above which no viable progeny are produced (Eigen, M. Error catastrophe and antiviral strategy. Proc. Natl. Acad. Sci. U.S.A. 99, 13374-13376 (2002); Manrubia, S. C., Domingo, E. & Lázaro, E. Pathways to extinction: beyond the error threshold. Philos. Trans. R. Soc. Lond., B, Biol. Sci. 365, 1943-1952 (2010); Domingo, E., Sheldon, J. & Perales, C. Viral quasispecies evolution. Microbiol. Mol. Biol. Rev. 76, 159-216 (2012); Domingo, E., Grande-Pérez, A. & Martín, V. Future prospects for the treatment of rapidly evolving viral pathogens: insights from evolutionary biology. Expert Opin. Biol. Ther. 8, 1455-1460 (2008); Domingo, E. et al. Viruses as quasispecies: biological implications. Curr. Top. Microbiol. Immunol. 299, 51-82 (2006)).

The mutagenic nucleoside triphosphate(s) then can be incorporated during RNA template-directed synthesis of the minus DNA strand of a virus in a virus-infected cell. Mutagenesis in the virus-infected cell may occur more frequently in the genome of the cells because of the incorporation of a mutagenic analog (e.g., a dihydro base described herein) into an RNA-DNA hybrid. First, reverse transcription occurs in the cytoplasm, whereas repair of cellular DNA is a nuclear process. Second, DNA repair enzymes have evolved to utilize double-stranded DNA that is present in a B-type structure, whereas RNA-DNA hybrids are in an A-type structure. In particular, a methyltransferase may fail to repair efficiently altered substrates when present in the DNA strand of an RNA-DNA hybrid. As a result, altered nucleotide residues in the DNA strand are not excised, and they pair with non-complementary nucleotides. Upon synthesis of a double-stranded viral DNA intermediate, the mutations are fixed; excision of the altered nucleotide would not obliterate the mutation. In contrast, incorporation of the mutagenic analog into the genome of the virus or cancer cell is subject to removal during DNA repair. After integration of the double-stranded viral DNA containing the mutation into the host genome, transcription results in corresponding base substitutions in the viral RNA. Iteration of this process by viral replication or cancerous proliferation will result in the progressive accumulation of mutations throughout the genome; some of these mutations would diminish the replication or proliferation. Eventually the mutations would exceed the error threshold for maintenance of the quasispecies, resulting in a precipitous decline in replication or proliferation.

Compounds described herein also can be used as hypomethylating agents that inhibit the activity of DNA methyltransferases thereby reducing the methylation and silencing of one or more genes (e.g., tumor suppressors) associated with cancer. Based upon the mechanism of action of 5-methylcytosine forming methyltransferases, which are believed to be epigenome modifying agents, the dihydro bases described herein may be refractory to natural genome methylation. Hence, the dihydro bases may find uses as epigenome modifying agents. Such agents may be useful as analytical reagents to people studying genome regulation. The dihydro bases may also have clinical utility. Accordingly, a cancer treatment can include the use of one or more compounds described herein. In some embodiments, compounds that show tautomerism (e.g., having a similar NMR profile to KP1212) do not exhibit significant cytotoxicity and can be used therapeutically as hypomethylating agents.

In some embodiments, one or more compounds described herein (e.g., dihydro bases or substituted forms thereof) can be useful to treat or assist in the treatment of an infection or disease described herein. In some embodiments, one or more compounds described herein can be administered alone. In some embodiments, one or more compounds described herein can be administered in combination with an additional agent (e.g., in the form of a preparation comprising two or more compounds, or as separate preparations that are administered together or separately during a treatment regimen) for the treatment of the infection or disease described herein. In some embodiments, compounds described herein can be used alone or in combination with one or more other antiviral agents to treat a viral infection.

In some embodiments, compounds described herein can be used alone or in combination with one or more anti-cancer agents (e.g., chemotherapeutic agents, other cytotoxic agents, or other anti-cancer agents) to treat cancer.

Figure 2:
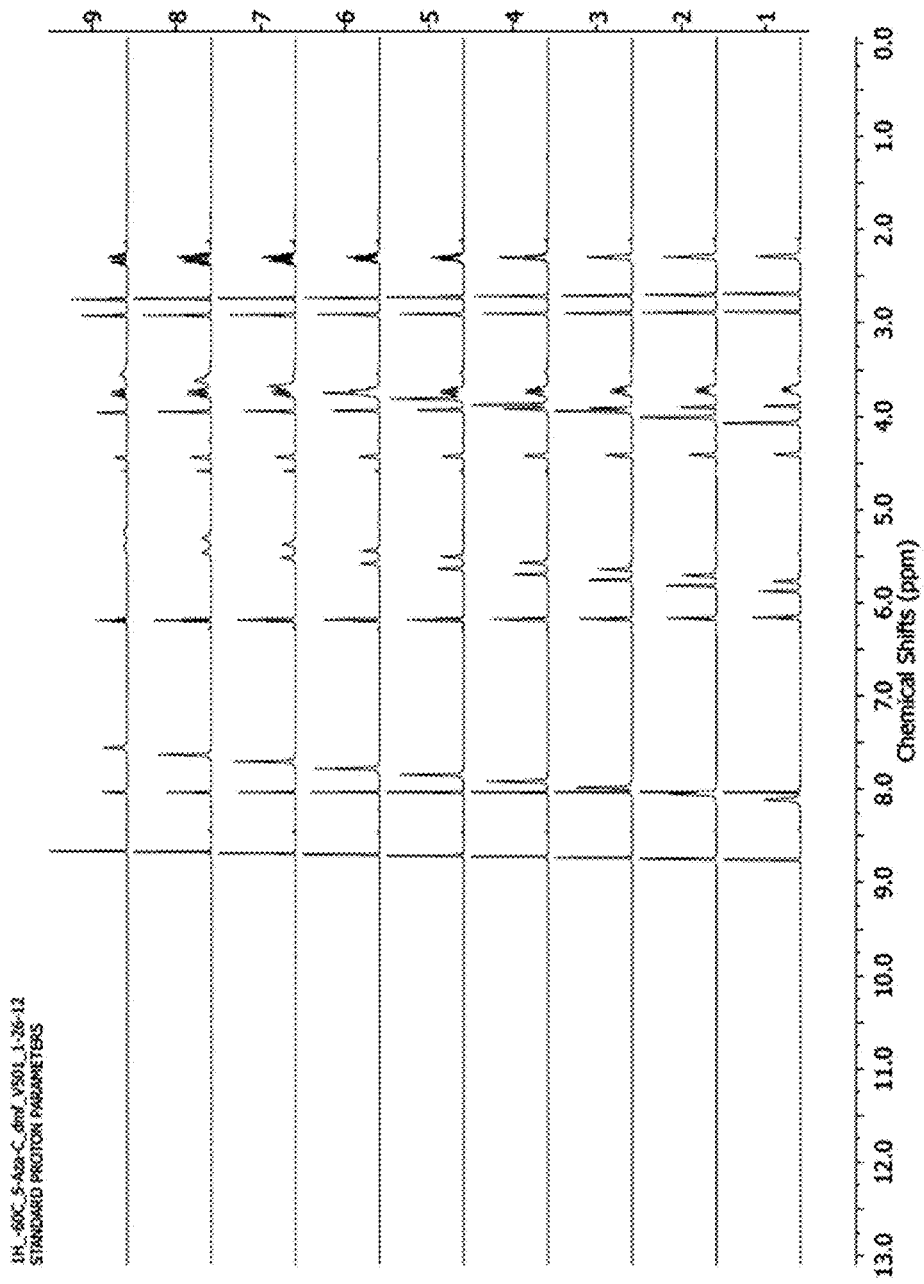
FIG. 2 shows exemplary Variable Temperature NMR (DMF-$d_7$) results indicating that compound 5-Aza-dC shows single tautomerism.
Figure 3:
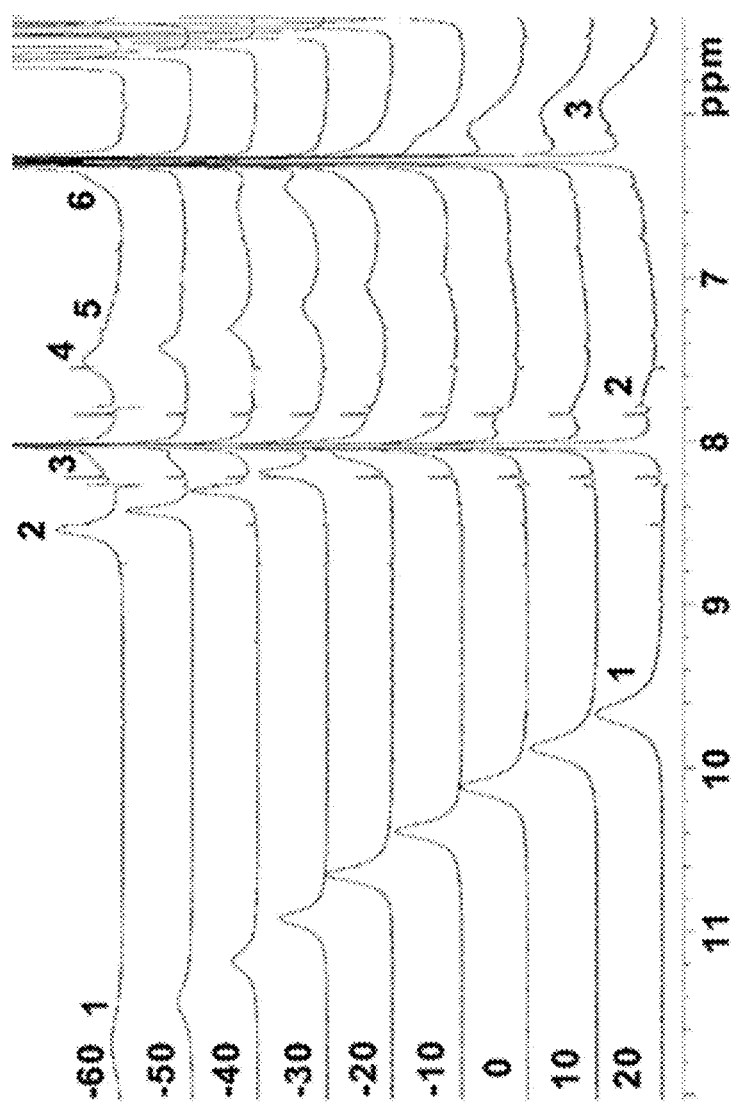
FIG. 3 shows exemplary Variable Temperature NMR (DMF-$d_7$) results indicating that compound KP1212 shows multiple tautomerism.
Figure 3:
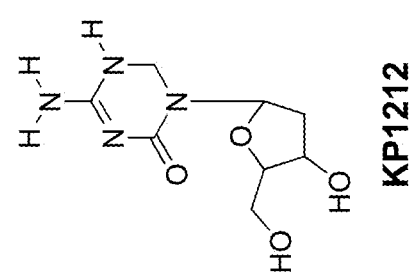
Figure 4:
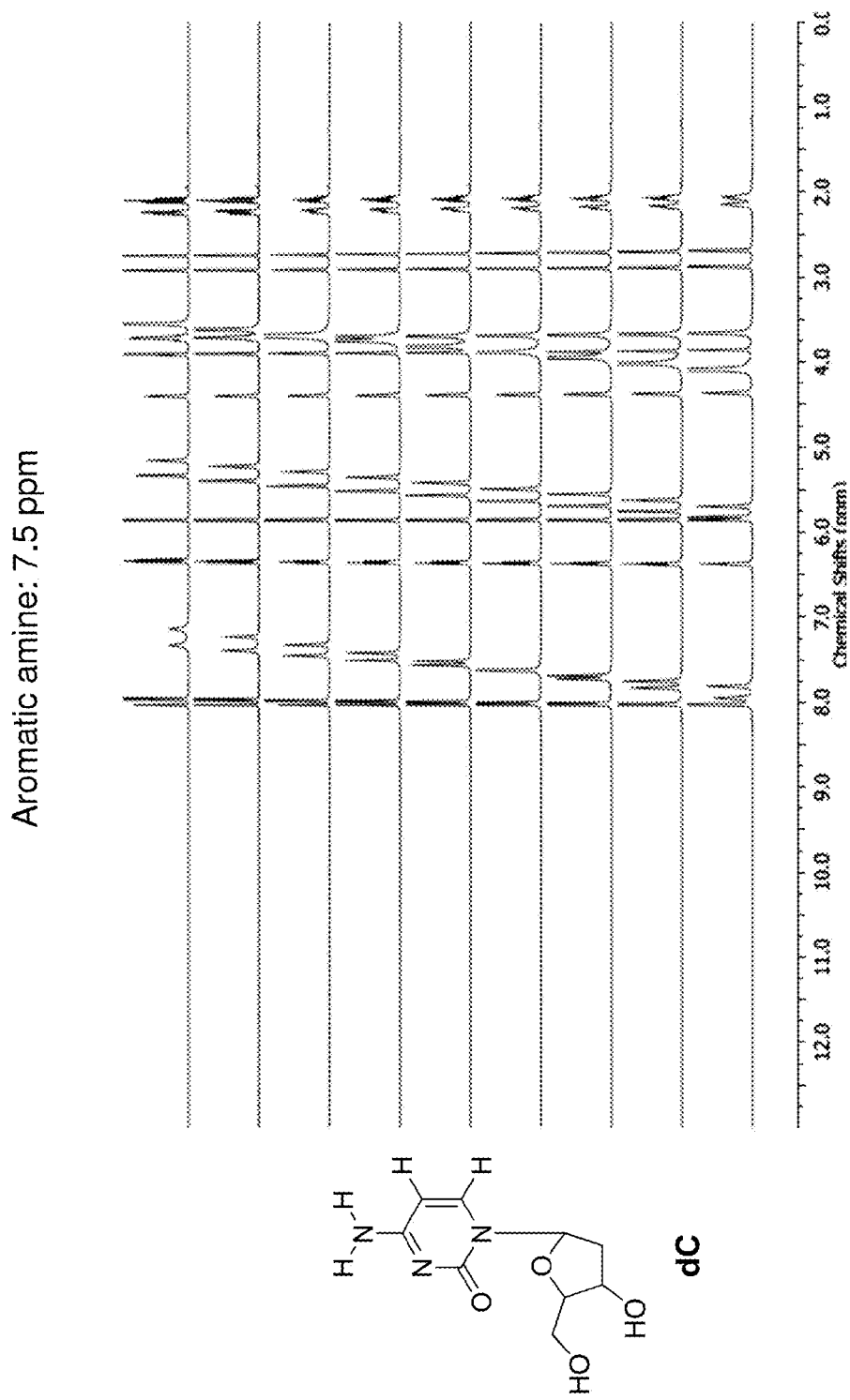
FIG. 4 shows exemplary Variable Temperature NMR (DMF-$d_7$) results indicating that compound dC shows single tautomerism.
Figure 5:
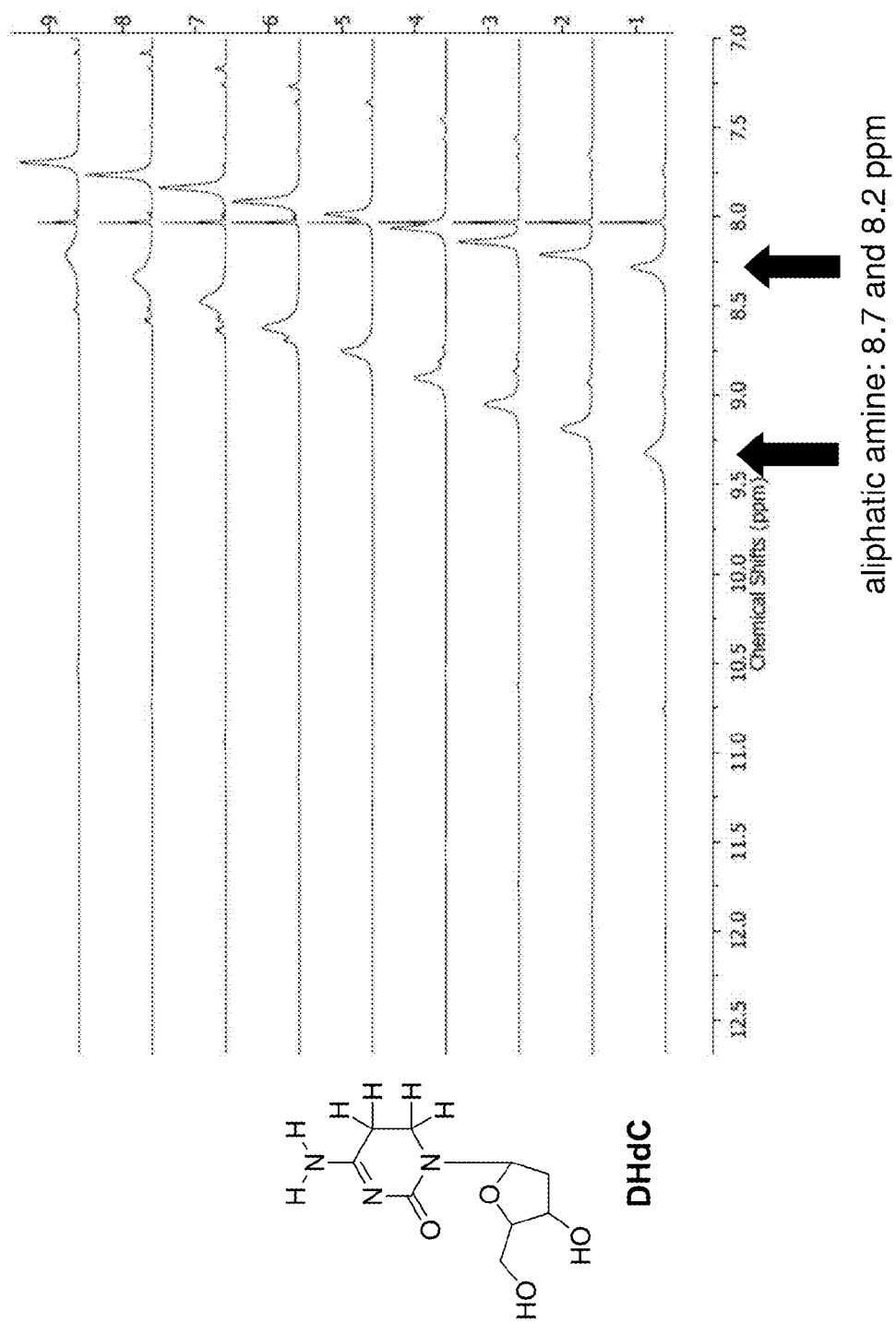
FIG. 5 shows exemplary Variable Temperature NMR (DMF-$d_7$) results indicating that dihydro base DHdC shows multiple tautomerism.

Compound 5-Aza-dC does not show multiple tautomerism (FIG. 2, Variable Temperature NMR (DMF-$d_7$) indicates single tautomerism of compound 5-Aza-dC). In contrast, KP1212, a dihydrogenated product from 5Aza-dC, shows multiple tautomerism (FIG. 3, Variable Temperature NMR (DMF-$d_7$) indicates multiple tautomerism of KP1212). KP1212 is an HIV inhibitor and has been proven to be mutagenestic. Similarly, deoxycytidine (dC) does not show multiple tautomerism (FIG. 4, Variable Temperature NMR (DMF-$d_7$) indicates single tautomerism of compound dC). From a structural standpoint, there are two differences between dC and KP1212. First, the carbon atom in position 5 is replaced by a nitrogen atom. Second, the 5,6-double bond in dC is reduced to a single bond in KP1212. In order to understand why KP1212 is able to readily tautomerize, while dC shows no evidence of tautomerization, each of these changes (C5 substitution and 5,6 saturation) was investigated independently. The unsaturated analog with a nitrogen atom substituted on the ring, 5-aza-2'-deoxycytidine (5-aza-dC) is commercially available and is used for the treatment of myelodysplastic syndromes under the name decitabine (Kantarjian H, Issa J P, Rosenfeld C S, et al. *Cancer* 2006, 106, 1794-1803; Kantarjian H M, O'Brien S, Cortes J, et al. *Cancer* 2003, 98, 522-528). Proton NMR studies of 5-aza-dC show almost no evidence of tautomerization (FIG. 2). This observation suggests that the effect of substituting a nitrogen atom at position 5 is not enough to explain KP1212's ability to tautomerize. Without wishing to be bound by any particular theory, the hydrogenation of the 5,6-double bond in the pyrimidine motif contributes greatly to the efficacy of KP1212 as a mutagenic nucleoside analog. Hydrogenation breaks the aromaticity of the pyrimidine base moiety, causing the electron density on the ring to become more localized. In addition, the heterocyclic ring may become puckered at the 5- and 6-positions when the aromaticity is broken. This puckering could contribute to the low cytotoxicity of KP1212, as human DNA polymerases may reject KP1212 due to its unnatural puckered shape. In contrast, compound DHdC, a dihydrogenated product from compound dC, shows multiple tautomerism (FIG. 5, Variable Temperature NMR (DMF-$d_7$) indicates multiple tautomerism of compound DHdC). Therefore, the dihydro bases described herein (e.g., compound DHdC) can show similar multiple tautomerism as KP1212, and thus can mimic the mutagenesis and/or hypomethylation properties of KP1212.

The dihydro bases described herein (e.g., compound DHdC) can be prepared according to methods known in the art. See, e.g., Green et al., *Journal of Biological Chemistry* 1957, 228, 601-9. An exemplary synthesis of compound DHdC is shown in Scheme 1 and the reaction conditions are shown in Table 1.

Scheme 1. Exemplary synthesis of compound DHdC

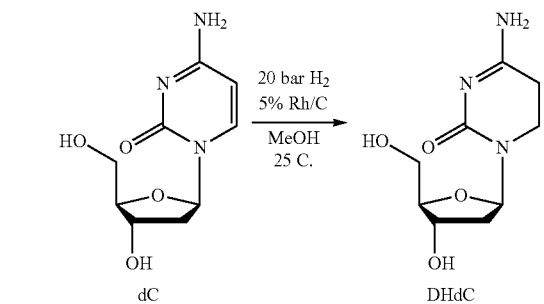

TABLE 1

Reagents and conditions for exemplary synthesis of compound DHdC

| Reaction | Catalyst | Concentration of dC | Temperature | Pressure | Percent DHdC | Byproducts |
|---|---|---|---|---|---|---|
| KS-001 | Rh/C (5%) | 0.037M | 25° C. | 20 bar | about 40% | No |
| KS-002 | Rh/C (5%) | 0.020M | 25° C. | 20 bar | about 30% | No |
| KS-003 | Rh/C (5%) | 0.020M | 25° C. | 80 bar | about 40% | No |
| KS-004 | Rh/C (5%) | 0.020M | 60° C. | 20 bar |  | Yes |

Figure 6:
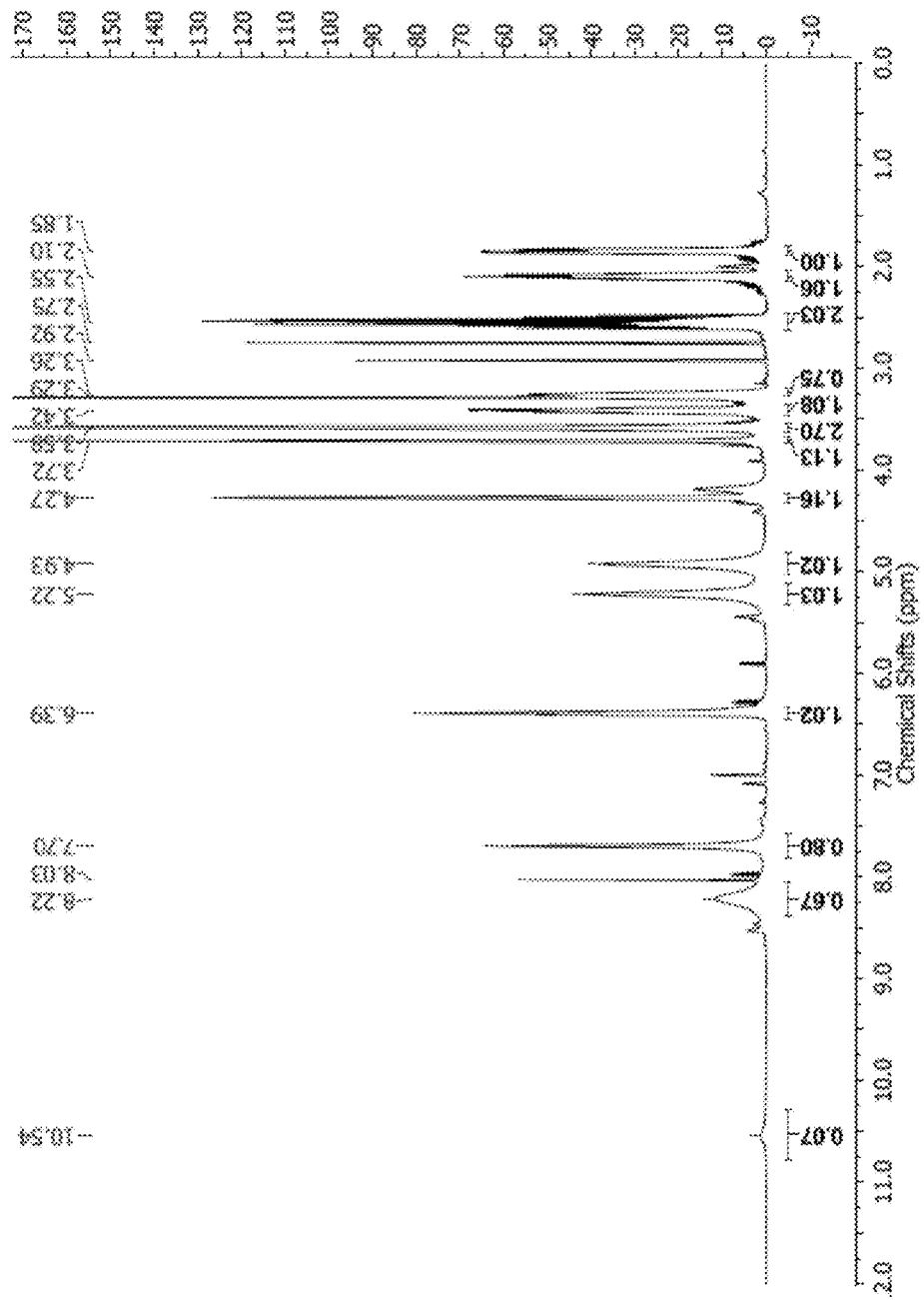
FIG. 6 shows an exemplary $^1$H NMR spectrum of a purified sample of dihydro base DHdC after Reaction KS-001-003.
Figure 7:
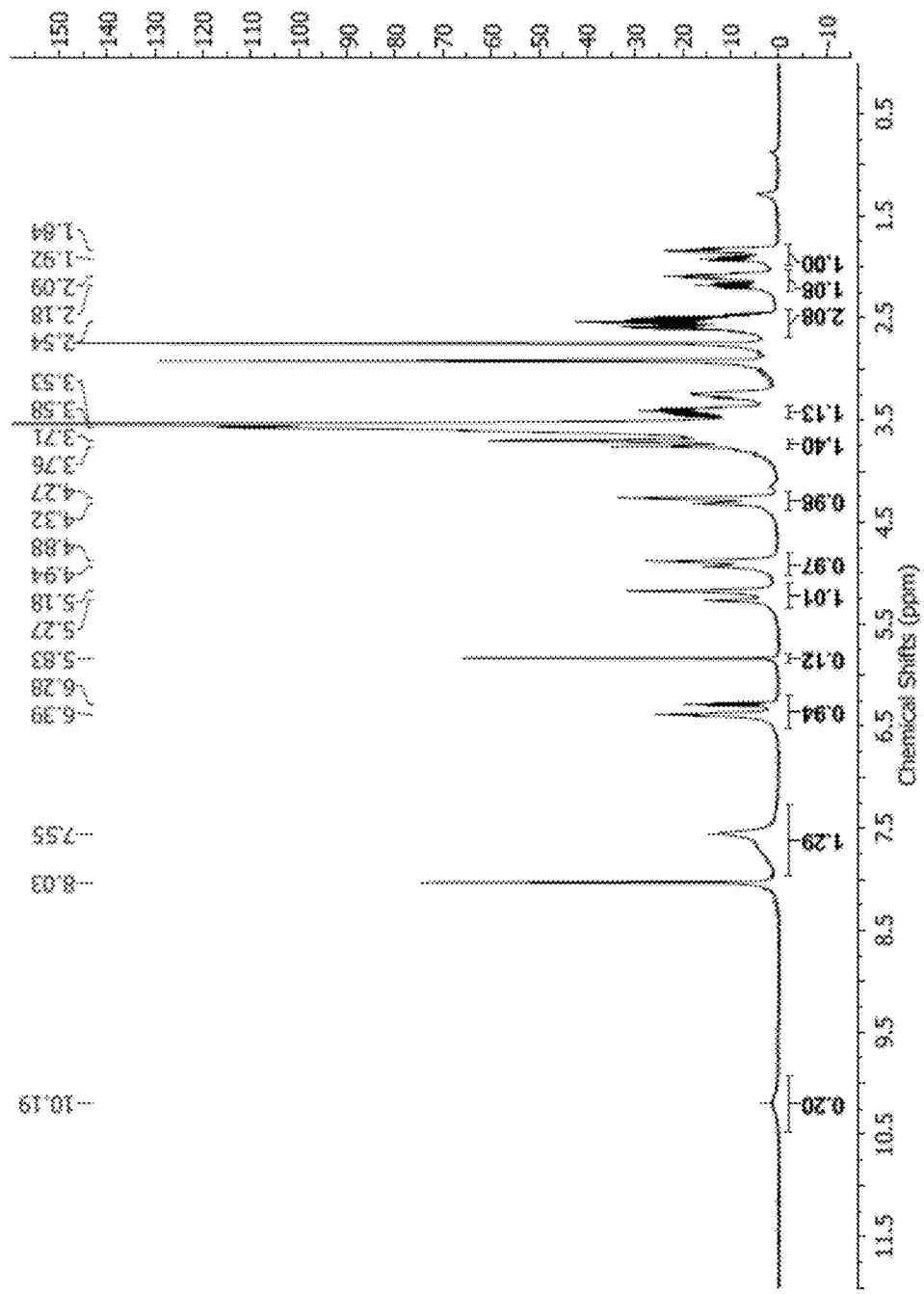
FIG. 7 shows an exemplary $^1$H NMR spectrum of a repurified sample of dihydro base DHdC after Reaction KS-001-003

In one example, compound DHdC was purified using a Biotage on silica gel using 12-50% methanol in DCM. After purification, TLC showed one spot and NMR showed about 5% starting material. FIG. 6 is a $^1$H NMR of the purified compound DHdC after Reaction KS-001-003. After repurification, TLC showed two closely spaced product spots. Two sets of peaks were observed in the repurified product NMR (FIG. 7). This may be because silica gel is acidic and may have catalyzed anomerization of compound DHdC.

In another example, a reverse phase column was used to purify compound DHdC.

DHdC may also be prepared according to Scheme 1A.

Scheme 1A. Exemplary synthesis of compound DHdC

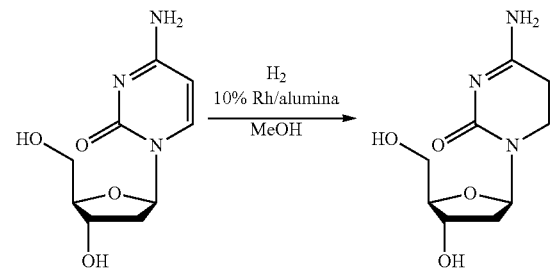

Previous work on the hydrogenation of dC revealed that rhodium on alumina was an effective catalyst for the reduction of the 5,6-double bond (Cohn, W. E. and Doherty, D. G. *JACS* 1956, 78, 2863-2868; Green, M. and Cohen, S. S. *J. Biol. Chem.* 1957, 228, 601-609; Hanze, A. R. *JACS* 1967, 89, 6720-6725). However, the authors noted that over-hydrogenation and hydrolysis of the 4-amino group presented difficulties. To address these concerns, flow chemistry was used to control the amount of time the nucleoside spends in contact with the catalyst and hydrogen gas, thereby avoiding over-hydrogenation. The nucleoside was dissolved in methanol instead of water to prevent hydrolysis of the amino group. In a preparation pursuant to Scheme 1A, DHdC was synthesized from dC via hydrogenation with 80-90% conversion in several flow reactions. One challenge presented by the reaction and purification processes is anomerization of the ribose sugar to form the α-anomer. The α-anomer of nucleoside derivatives cannot be easily used by RT or DNA polymerases and thus is unlikely to have medicinal relevance. Anomerization appears to be catalyzed by acidic conditions, as anomerization occurs to a great extent when Rh/alumina is used as the catalyst instead of Rh/C. However, slightly acidic conditions typically increase the rate of hydrogenation reactions, as more protons are available to react with the starting material. As a result, Rh/alumina displays a higher conversion rate than Rh/C (80-90% compared to 20-30%). The increase in conversion rate provided by Rh/alumina was great enough that it was determined to be a better catalyst for the hydrogenation reaction than Rh/C, even though the undesired α-anomer would have to be separated from the desired β-anomer. To prevent further anomerization during purification on acidic silica gel, MeOH saturated with ammonia (MeOH—NH$_3$) was used as the polar solvent in the mobile phase.

Therefore, another aspect of the present invention relates to methods of preparing the dihydro bases as described herein. In certain embodiments, a method of preparing a dihydro base (e.g., substituted or unsubstituted DHdC) includes hydrogenating a base (e.g., substituted or unsubstituted dC) in the presence of a catalyst (e.g., Rh/alumina) to provide the dihydro base. In certain embodiments, a method of preparing a dihydro base includes flow chemistry. In certain embodiments, a method of preparing a dihydro base includes an alcoholic solvent (e.g., MeOH). In certain embodiments, a method of preparing a dihydro base does not include water as a solvent. In certain embodiments, a method of preparing a dihydro base further includes purifying the dihydro base provided by the step of hydrogenating using flash chromatography (e.g., normal or reverse phase flash chromatography eluted with a basic mobile phase (e.g., MeOH—NH$_3$, EtOH—NH$_3$, PrOH—NH$_3$, or acetonitrile-NH$_3$)).

An exemplary synthesis of compound DHdU is shown in Scheme 2 and the reaction conditions are shown in Table 2.

Scheme 2. Exemplary synthesis of compound DHdU

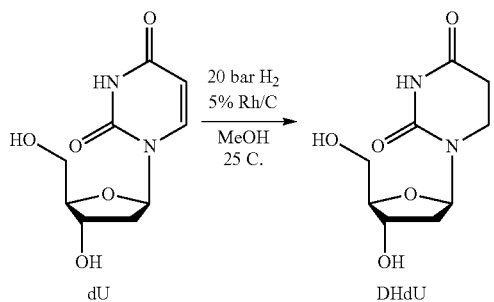

TABLE 2

Reagents and conditions for exemplary synthesis of compound DHdU

| Reaction | Catalyst | Concentration of dU | Temperature | Pressure | Percent DHdC | Byproduct |
|---|---|---|---|---|---|---|
| KS-006 | Rh/C (5%) | 0.037M | 25° C. | 20 bar | ~100% | No |

The dihydro bases and pharmaceutical compositions can be useful in treating and/or preventing a viral infection or cancer in a subject. In one aspect, the present invention provides methods of treating a viral infection. In another aspect, the present invention provides methods of preventing a viral infection. In certain embodiments, the subject is a human. In certain embodiments, the subject is a non-human animal. In certain embodiments, the subject is a non-human mammal. In certain embodiments, the viral infection that may be treated by the dihydro bases, pharmaceutical compositions, and/or kits described herein is an RNA virus infection. In certain embodiments, the viral infection is a retrovirus infection. In certain embodiments, the viral infection is a DNA virus infection. Dengue fever, Dengue hemorrhagic fever (DHF), Dengue shock syndrome (DSS), hepatitis A, hepatitis B, hepatitis C, hepatitis D, hepatitis E, hepatitis F, Coxsackie A virus infection, Coxsackie B virus infection, fulminant viral hepatitis, severe acute respiratory syndrome (SARS), viral myocarditis, influenza virus infection (e.g., influenza A virus infection (e.g., an H1N1, H1N2, H2N1, H2N2, H2N3, H3N1, H3N2, H3N8, H5N1, H7N7, H1N2, H9N2, H7N2, H7N3, H7N9, H5N2, H10N7 virus infection), influenza B virus infection, influenza C virus infection), parainfluenza virus infection, an RS virus (RSV) infection (e.g., RSV bronchiolitis, RSV pneumonia, especially an infant and childhood RSV infection and RSV pneumonia in the patients with cardiopulmonary disorders), measles virus infection, vesicular stomatitis virus infection, rabies virus infection, Ebola virus infection, Japanese encephalitis, Junin virus infection, human cytomegalovirus infection, herpes virus infection (e.g., iltovirus infection, mardivirus infection, simplexvirus infection (herpes simplex virus 1 infection), varicellovirus infection, cytomegalovirus infection, muromegalovirus infection, proboscivirus infection, roseolovirus infection, lymphocryptovirus infection, macavirus infection, percavirus infection, rhadinovirus infection), poliovirus infection, Marburg virus infection, Lassa fever virus infection, Venezuelan equine encephalitis, Rift Valley Fever virus infection, Korean hemorrhagic fever virus infection, Crimean-Congo hemorrhagic fever virus infection, HIV infection, acquired immunodeficiency syndrome (AIDS), encephalitis, Saint Louise encephalitis, Kyasanur Forest disease, Murray Valley encephalitis, tick-borne encephalitis, West Nile encephalitis, yellow fever, or a viral infection in subjects with immune disorders. In certain embodiments, the viral infection is an influenza virus infection. In certain embodiments, the viral infection is an influenza A virus infection. In certain embodiments, the viral infection is human flu (e.g., H1N1, H2N2, H3N2, H5N1, H7N7, H1N2, H9N2, H7N2, H7N3, or H10N7 virus infection). In certain embodiments, the viral infection is bird flu (e.g., H5N1 or H7N9 virus infection). In certain embodiments, the viral infection is swine influenza (e.g., H1N1, H1N2, H2N1, H3N1, H3N2, or H2N3 virus infection, or influenza C virus infection). In certain embodiments, the viral infection is equine influenza (e.g., H7N7 or H3N8 virus infection). In certain embodiments, the viral infection is canine influenza (e.g., H3N8 virus infection). In certain embodiments, the viral infection is an influenza B virus infection. In certain embodiments, the viral infection is an influenza C virus infection. In certain embodiments, the viral infection is HIV infection or AIDS. In certain embodiments, the viral infection is hepatitis C.

In another aspect, the present invention provides methods of treating cancer. In yet another aspect, the present invention provides methods of preventing cancer. In certain embodiments, the cancer that may be treated by the dihydro bases, pharmaceutical compositions, and/or kits described herein is acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endothelio sarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); a hematopoietic cancer (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; or vulvar cancer (e.g., Paget's disease of the vulva). In certain embodiments, the cancer is a cancer with a mutator phenotype (e.g., a cancer with an increased mutation rate in the cancer cells, compared to a different cancer).

Any of the pharmaceutical compositions described herein can be formulated for a suitable administration route, e.g., orally, parenterally, by inhalation spray, topically, rectally, nasally, buccally, vaginally or via an implanted reservoir. The term "parenteral" as includes subcutaneous, intracutaneous, intravenous, intramuscular, intraarticular, intraarterial, intrasynovial, intrasternal, intrathecal, intralesional and intracranial injection or infusion techniques.

A sterile injectable pharmaceutical composition, e.g., a sterile injectable aqueous or oleaginous suspension, can be formulated according to techniques known in the art using suitable dispersing or wetting agents (such as Tween® 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A pharmaceutical composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation pharmaceutical composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A pharmaceutical composition of the invention can also be administered in the form of suppositories for rectal administration.

The pharmaceutical compositions of the invention optionally include a pharmaceutical acceptable excipient. Pharmaceutically acceptable excipients that may be included in a pharmaceutical composition of the invention include inert diluents, solubilizing agents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the pharmaceutical composition. An excipient present in an inventive pharmaceutical composition must be "pharmaceutically acceptable" in the sense that the excipient is compatible with the active ingredient of the pharmaceutical composition (and preferably, capable of stabilizing the pharmaceutical composition) and not deleterious to a subject to whom the pharmaceutical composition is administered. For example, solubilizing agents such as cyclodextrins, which may form specific, more soluble complexes with the dihydro bases described herein, can be utilized as pharmaceutically acceptable excipients for delivery of the dihydro bases described herein into the subject. Examples of other pharmaceutically acceptable excipients include colloidal silicon dioxide, magnesium stearate, cellulose, sodium lauryl sulfate, and D&C Yellow #10.

The pharmaceutical compositions may also include one or more pharmaceutical agents, such as antifungal agents, antiprotozoan agents, anti-bacterial agents, anti-viral agents, anti-inflammatory agents, pain-relieving agents, and antiproliferative agents. In certain embodiments, the combination of a dihydro base described herein and additional pharmaceutical agent shows a synergistic effect.

Also encompassed by the invention are kits (e.g., pharmaceutical packs). The inventive kits may be useful for treating and/or preventing a viral infection and/or cancer. The kits provided may comprise a dihydro base or pharmaceutical composition described herein and a container (e.g., a vial, ampule, bottle, syringe, and/or dispenser package, or other suitable container). In some embodiments, provided kits may optionally further include a second container comprising a pharmaceutical excipient for dilution or suspension of a dihydro base or pharmaceutical composition described herein. In some embodiments, the pharmaceutical composition or dihydro base provided in the container and the second container are combined to form one unit dosage form. In certain embodiments, the kits further include instructions for administering the dihydro base or pharmaceutical composition, to a subject to treat the rival infection and/or cancer.

In certain embodiments, a kit of the invention includes DHdC, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, a kit of the invention includes substituted DHdC (e.g., DH-5-OH-dC, DH-5-halo-dC), or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, a kit of the invention includes KP1212, or a pharmaceutically acceptable salt, solvate, hydrate, polymorph, co-crystal, tautomer, stereoisomer, isotopically labeled derivative, or prodrug thereof, or a pharmaceutical composition thereof.

In another aspect, the present invention provides methods of treating a viral infection in a subject in need thereof.

In another aspect, the present invention provides methods of treating cancer in a subject in need thereof.

In another aspect, the present invention provides methods of increasing the mutation of a RNA and/or DNA of a virus or cancer cell.

Another aspect of the present invention relates to methods of killing a virus or inhibiting the replication of a virus.

Another aspect of the present invention relates to methods of inducing apoptosis of a cancer cell.

In yet another aspect, the present invention provides the pharmaceutical compositions of the invention for use in the treatment and/or prevention of a viral infection and/or cancer in a subject in need thereof.

In certain embodiments, the methods of the invention comprise administering to the subject or contacting the virus or cancer cell with an effective amount of a dihydro base or pharmaceutical composition described herein. In certain embodiments, the effective amount is a therapeutically effective amount. In certain embodiments, the effective amount is a prophylactically effective amount.

The following definitions are more general terms used throughout the present application:

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is non-human animal. In certain embodiments, the animal is fish.

The terms "administer," "administering," or "administration" refers to implanting, absorbing, ingesting, injecting, inhaling, or otherwise introducing a dihydro base described herein, or a pharmaceutical composition thereof, in or on a subject.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein, such as a fungal or protozoan infection. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of exposure to a pathogen). Treatment may also be continued after symptoms have resolved, for example, to delay or prevent recurrence.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, and/or enhances the therapeutic efficacy of another therapeutic agent.

Exemplary embodiments of the invention include embodiments 1 to 26:

Embodiment 1

A dihydro base of the formula:

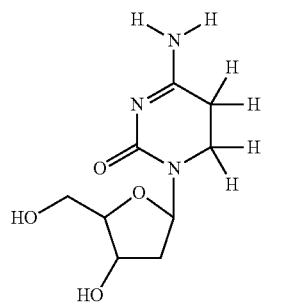

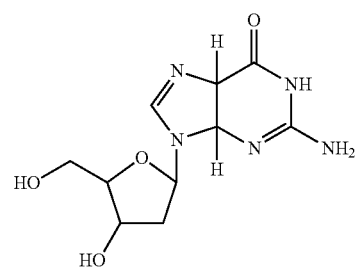

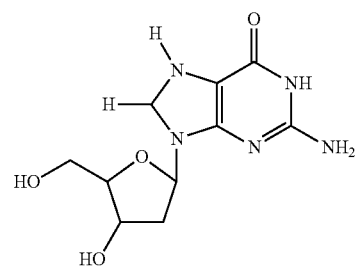

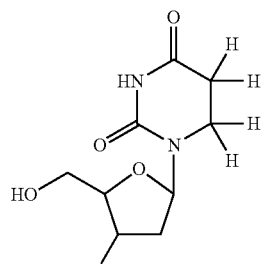

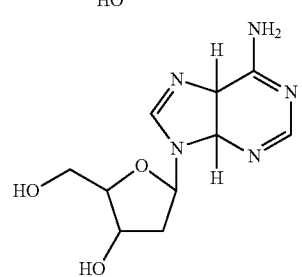

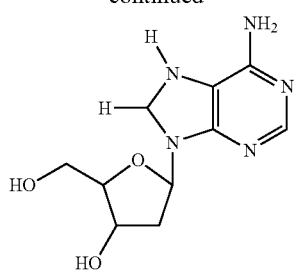

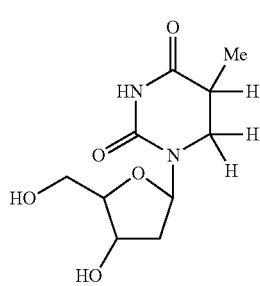  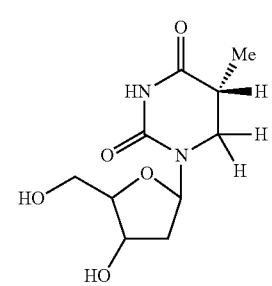

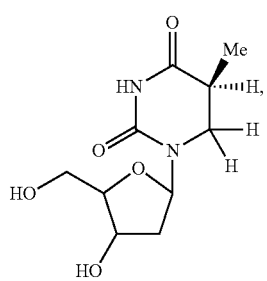

or a pharmaceutically acceptable salt, tautomer, or stereoisomer thereof, wherein at least one hydrogen atom of each formula is independently substituted by a non-hydrogen atom or group.

Embodiment 2

The dihydro base of embodiment 1, wherein the dihydro base is of the formula:

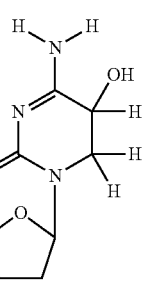  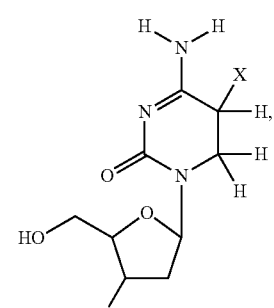

X is F, Cl, Br, or I or a pharmaceutically acceptable salt, tautomer, or stereoisomer thereof.

Embodiment 3
A pharmaceutical composition comprising a dihydro base of embodiment 1 or 2 or of the formula:
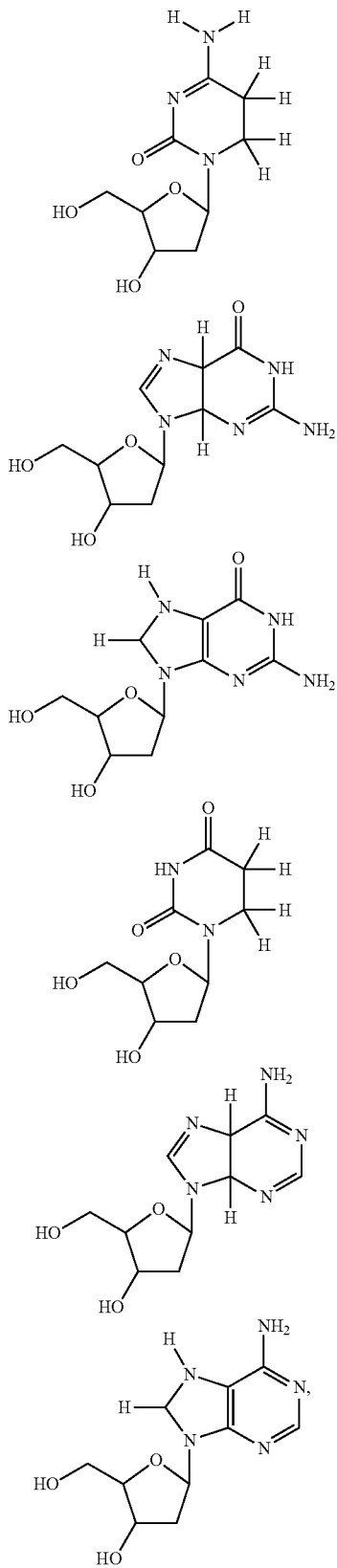
or a pharmaceutically acceptable salt, tautomer, or stereoisomer thereof, and optionally a pharmaceutically acceptable excipient.
Embodiment 4
The pharmaceutical composition of embodiment 3, wherein the dihydro base is of the formula:
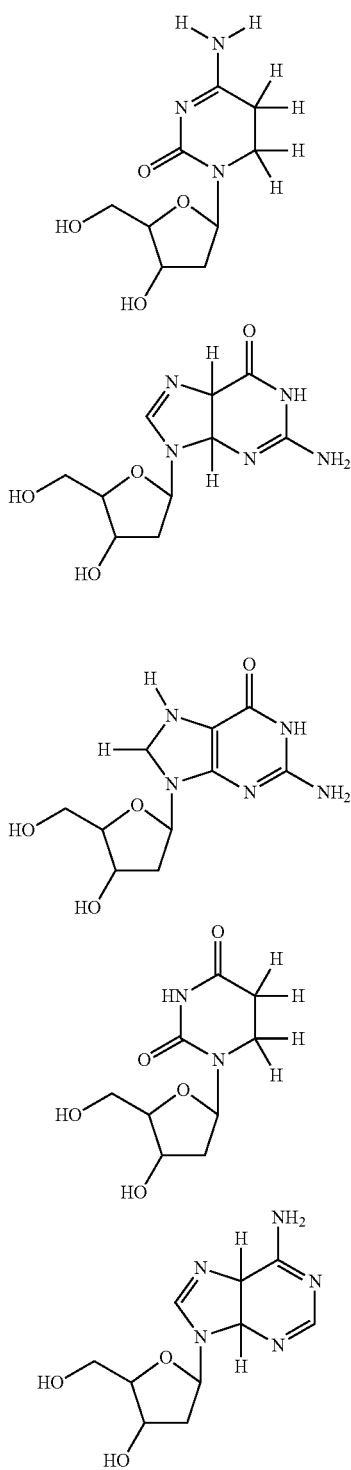

-continued

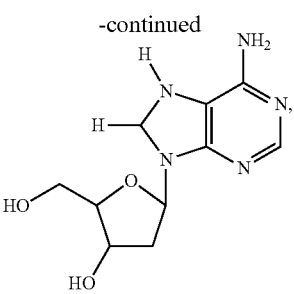

or a pharmaceutically acceptable salt, tautomer, or stereoisomer thereof, and optionally a pharmaceutically acceptable excipient.

Embodiment 5

The pharmaceutical composition of embodiment 3, wherein the dihydro base is of the formula:

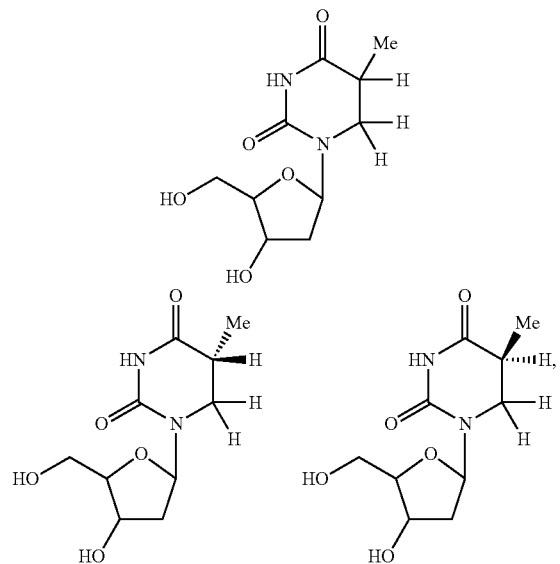

or a pharmaceutically acceptable salt, tautomer, or stereoisomer thereof, and optionally a pharmaceutically acceptable excipient.

Embodiment 6

The pharmaceutical composition of embodiment 3, wherein the dihydro base is of the formula:

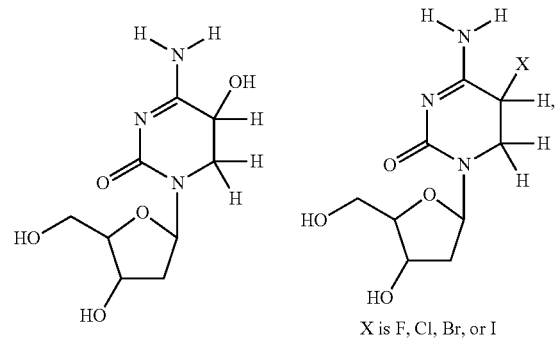

X is F, Cl, Br, or I or a pharmaceutically acceptable salt, tautomer, or stereoisomer thereof, and optionally a pharmaceutically acceptable excipient.

Embodiment 7

The pharmaceutical composition of embodiment 3, 4, 5, or 6, wherein the pharmaceutical composition comprises an effective amount of the dihydro base, or a pharmaceutically acceptable salt, tautomer, or stereoisomer thereof, for treating a viral infection in a subject in need thereof.

Embodiment 8

The pharmaceutical composition of embodiment 3, 4, 5, or 6, wherein the pharmaceutical composition comprises an effective amount of the dihydro base, or a pharmaceutically acceptable salt, tautomer, or stereoisomer thereof, for treating cancer in a subject in need thereof.

Embodiment 9

The pharmaceutical composition of any one of embodiments 3-8, further comprising an additional pharmaceutical agent in combination with the dihydro base, or a pharmaceutically acceptable salt, tautomer, or stereoisomer thereof.

Embodiment 10

A method of treating a viral infection in a subject in need thereof, the method comprising administering to the subject a therapeutically effective amount of a dihydro base of embodiment 1 or 2, or a pharmaceutically acceptable salt, tautomer, or stereoisomer thereof, or a pharmaceutical composition of any one of embodiments 3-9.

Embodiment 11

A method of increase the mutation rate of an RNA and/or DNA of a virus, the method comprising contacting the virus with an effective amount of a dihydro base of embodiment 1 or 2, or a pharmaceutically acceptable salt, tautomer, or stereoisomer thereof, or a pharmaceutical composition of any one of embodiments 3-9.

Embodiment 12

A method of increase the mutation rate of an RNA and/or DNA of a virus, the method comprising contacting the virus with an effective amount of a compound of the formula:

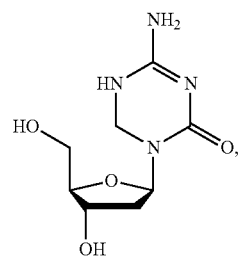

or a pharmaceutically acceptable salt or tautomer thereof.

Embodiment 13

A method of killing a virus or inhibiting replication of a virus, the method comprising contacting the virus with an effective amount of a dihydro base of embodiment 1 or 2, or a pharmaceutically acceptable salt, tautomer, or stereoisomer thereof, or a pharmaceutical composition of any one of embodiments 3-9.

Embodiment 14

A method of treating cancer in a subject in need thereof, the method comprising administering to the subject a therapeutically effective amount of a dihydro base of embodiment 1 or 2, or a pharmaceutically acceptable salt, tautomer, or stereoisomer thereof, or a pharmaceutical composition of any one of embodiments 3-9.

Embodiment 15

A method of increasing the mutation rate of an RNA and/or DNA of a cancer cell, the method comprising contacting the cancer cell with an effective amount of a dihydro base of embodiment 1 or 2, or a pharmaceutically acceptable salt, tautomer, or stereoisomer thereof, or a pharmaceutical composition of any one of embodiments 3-9.

Embodiment 16

A method of inducing apoptosis of a cancer cell, the method comprising contacting the cancer cell with an effective amount of a dihydro base of embodiment 1 or 2, or a pharmaceutically acceptable salt, tautomer, or stereoisomer thereof, or a pharmaceutical composition of any one of embodiments 3-9.

Embodiment 17

A method of decreasing DNA methylation in a cancer cell in a subject in need thereof, the method comprising administering to the subject a therapeutically effective amount of a dihydro base of embodiment 1 or 2, or a pharmaceutically acceptable salt, tautomer, or stereoisomer thereof, or a pharmaceutical composition of any one of embodiments 3-9.

Embodiment 18

A method of treating cancer in a subject in need thereof, the method comprising administering to the subject a therapeutically effective amount of a compound of the formula:

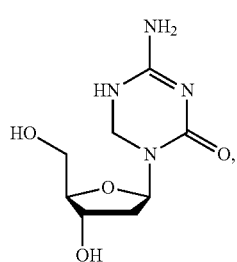

or a pharmaceutically acceptable salt or tautomer thereof.

Embodiment 19

A method of increasing the mutation rate of an RNA and/or DNA of a cancer cell, the method comprising contacting the cancer cell with an effective amount of a compound of the formula:

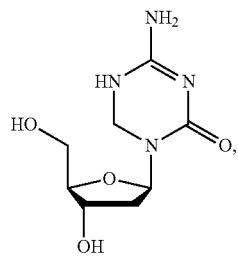

or a pharmaceutically acceptable salt or tautomer thereof.

Embodiment 20

A method of inducing apoptosis of a cancer cell, the method comprising contacting the cancer cell with an effective amount of a compound of the formula:

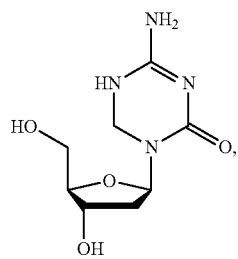

or a pharmaceutically acceptable salt or tautomer thereof.

Embodiment 21

A method of decreasing DNA methylation in a cancer cell in a subject in need thereof, the method comprising administering to the subject a therapeutically effective amount of a compound of the formula:

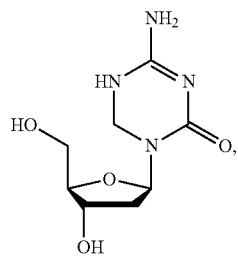

or a pharmaceutically acceptable salt or tautomer thereof.

Embodiment 22

The method of any one of embodiments 7-8, 10, 14, 17-18, and 21, wherein the subject is a human.

Embodiment 23

The pharmaceutical composition of embodiment 7 or the method of embodiment 10, wherein the viral infection is an influenza virus infection.

Embodiment 24

The pharmaceutical composition of embodiment 7 or the method of embodiment 10, wherein the viral infection is human immunodeficiency virus (HIV) infection.

Embodiment 25

The pharmaceutical composition of embodiment 8 or the method of any one of embodiments 14-21, wherein the cancer is a cancer with a mutator phenotype.

Embodiment 26

A kit comprising:
a dihydro base of embodiment 1 or 2, or a pharmaceutically acceptable salt, tautomer, or stereoisomer thereof, or a pharmaceutical composition of any one of embodiments 3-9; and
instructions for using the kit.

The present application refers to various issued patent, published patent applications, journal articles, and other publications, all of which are incorporated herein by reference.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1

Preparation of the Compounds

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

Preparation of Dihydro Base DHdC

In an exemplary experiment, DHdC was prepared according to Scheme 3. 2'-Deoxycytidine (284.8 mg, 1.253 mmol) was dissolved in 25 mL MeOH via sonication to form a 0.05 M solution. Three stainless steel cartridges were packed with about 400 mg of Rh/alumina (5%) each and connected in series. The solution was loaded into an 8 mL stainless steel syringe in a syringe pump and connected to the cartridges and a hydrogen gas tank via a Y-linker. The solution and hydrogen gas were pumped through the connected cartridges at a flow rate of 80 µL/min with hydrogen gas pressure of 175 psi. The outflow was connected in ~5 mL fractions and checked via TLC (30% MeOH—$NH_3$ in DCM on silica, starting material $R_f$=0.29, product $R_f$=0.14). All fractions showed similar conversion rates and were combined and concentrated via rotary evaporation to 282 mg of a white, sticky solid. Proton NMR showed ~80% conversion to product with partial anomerization (~20-30% alpha anomer) of the ribose sugar. To purify the beta anomer product, a column of silica gel was prepared using 10% MeOH—$NH_3$ in DCM. The product was dissolved in a minimal amount of MeOH—$NH_3$ in DCM and loaded onto the column. The column was eluted with a gradient of 10-30% MeOH—$NH_3$ in DCM. Fractions that appeared to contain the desired product on TLC were combined and concentrated via rotary evaporation to yield 61.3 mg of a light yellow solid. Proton NMR showed <10% of the undesired α-anomer and >90% of the desired β-anomer. The product was repurified using a pipette column prepared with silica gel using 10% MeOH—$NH_3$ in DCM. The product was dissolved in a minimal amount of MeOH—$NH_3$ in DCM and loaded onto the column. The column was eluted with a gradient of 10-20% MeOH—$NH_3$ in DCM. Fractions that appeared to contain the desired product on TLC were combined and concentrated via rotary evaporation to yield 32.1 mg of a light yellow solid. Proton NMR showed full conversion to the desired product with no starting material remaining and <5% of the undesired α-anomer.

Example 2

Figure 8:
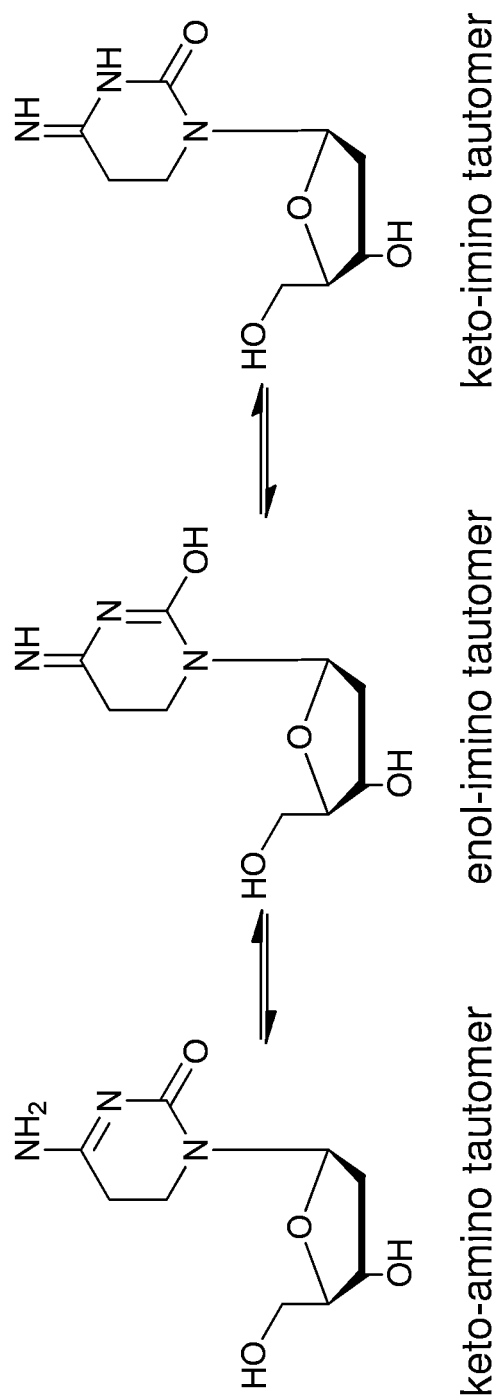
FIG. 8 shows exemplary tautomers of dihydro base DHdC.
Figure 9:
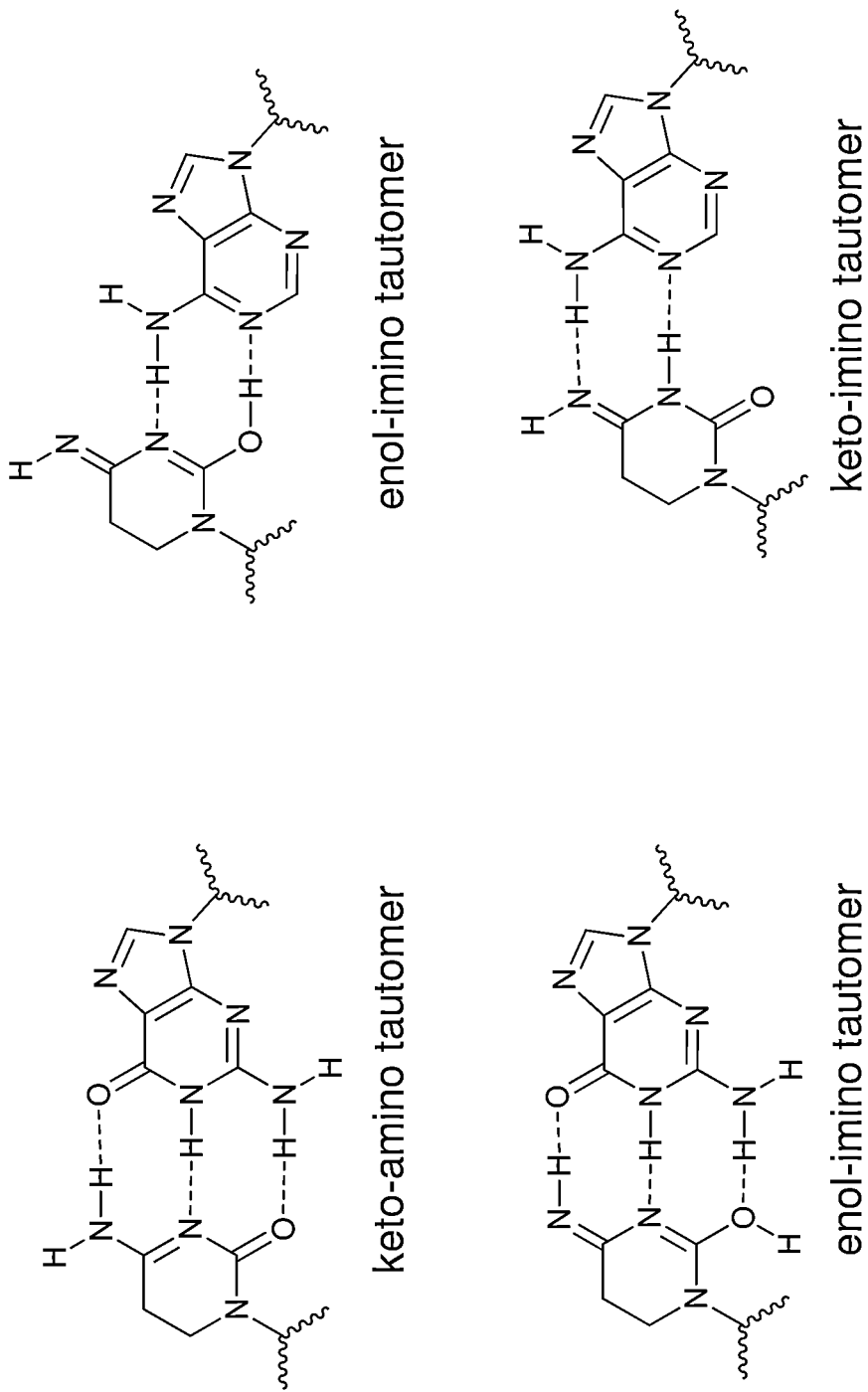
FIG. 9 shows exemplary base pairings of exemplary tautomers of dihydro base DHdC with guanine and adenine.
Figure 10:
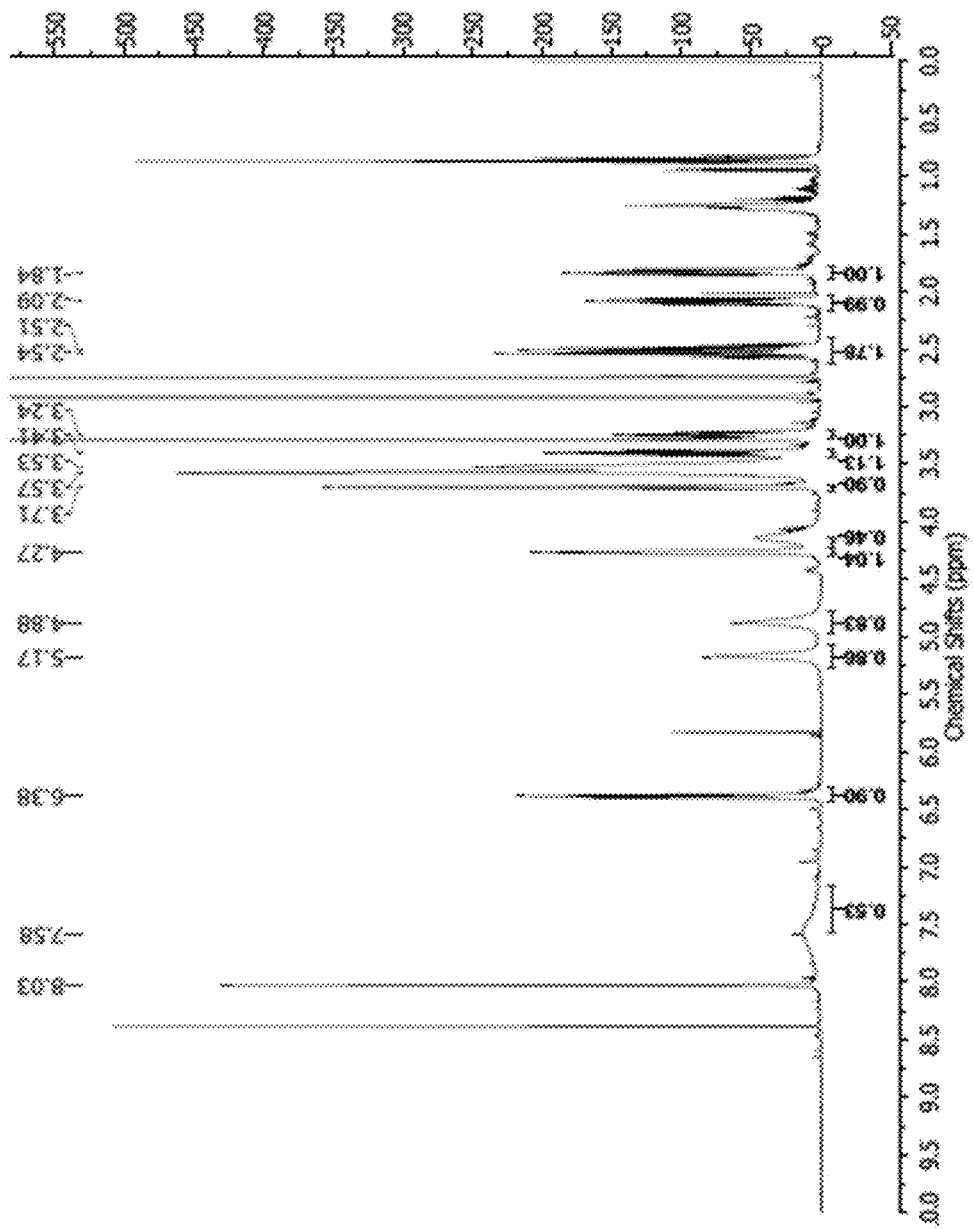
FIG. 10 shows an exemplary $^1$H NMR spectrum of dihydro base DHdC in DMF-$d_7$ at 20° C.
Figure 11:
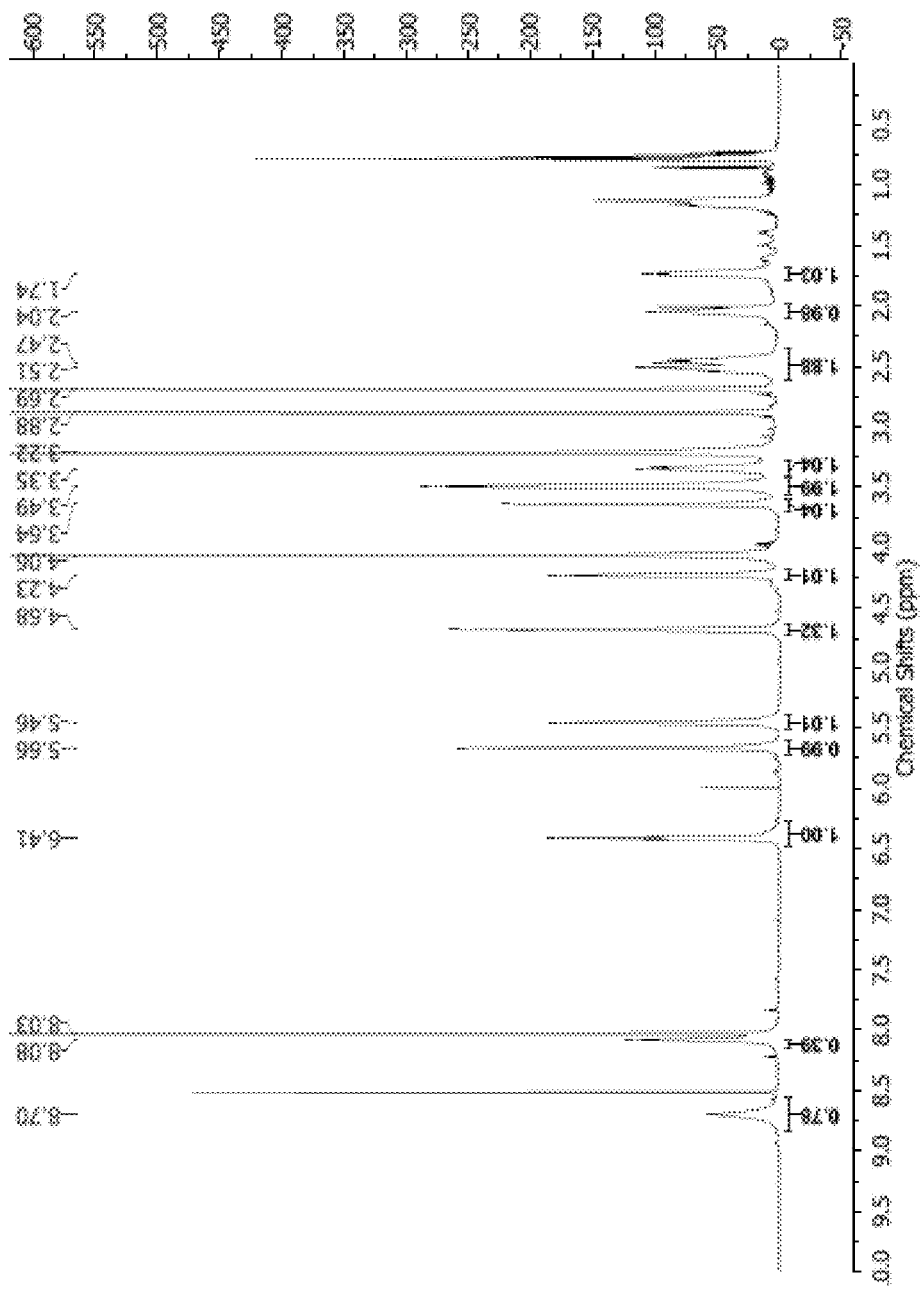
FIG. 11 shows an exemplary $^1$H NMR spectrum of dihydro base DHdC in DMF-$d_7$ at −60° C.

Variable Temperature (VT) $^1$H NMR Experiments Showing Multiple Tautomerism of Dihydro Base DHdC To determine whether DHdC displays multiple tautomers that could allow it to base pair with both adenine and guanine (FIGS. 8 and 9), variable temperature (VT) proton NMR was used. Low temperature NMR decreases the rate of interconversion among tautomers such that multiple tautomers can be observed on the NMR timescale. At 20° C., exchangeable protons on the base moiety are observed at 7.58 ppm and 4.14 ppm (FIG. 10). At −60° C., exchangeable protons on the base moiety are observed at 8.70 ppm, 8.08 ppm, and 4.68 ppm (FIG. 11). Protons with a chemical shift of 8.70, 8.08, and 7.58 ppm likely correspond to enolic, amido, or imino protons, while protons with a chemical shift of 4.68 and 4.14 ppm likely correspond to amino protons. The expected chemical shifts for enolic, amido, and imino protons are relatively close, and thus these species cannot be assigned at this stage. However, VT NMR clearly shows three resonances at low temperature, though only two active protons are present on the base moiety. Only the existence of multiple tautomeric species would explain the presence of three exchangeable protons resonances. Furthermore, the chemical shifts observed suggest that both the keto-amino and keto-imino/enol-imino tautomers occur. Based on their chemical structures, the keto-amino tautomer will pair with guanine and the keto-imino/enol-imino tautomers can pair with adenine. Due to the existence of multiple tautomers, DHdC may be able to alternatively base pair (FIG. 9) and cause adenine to guanine and guanine to adenine mutations, similarly to KP1212.

Example 3

Experiments Showing Multiple Tautomerism of Compound KP1212

Figure 13A:
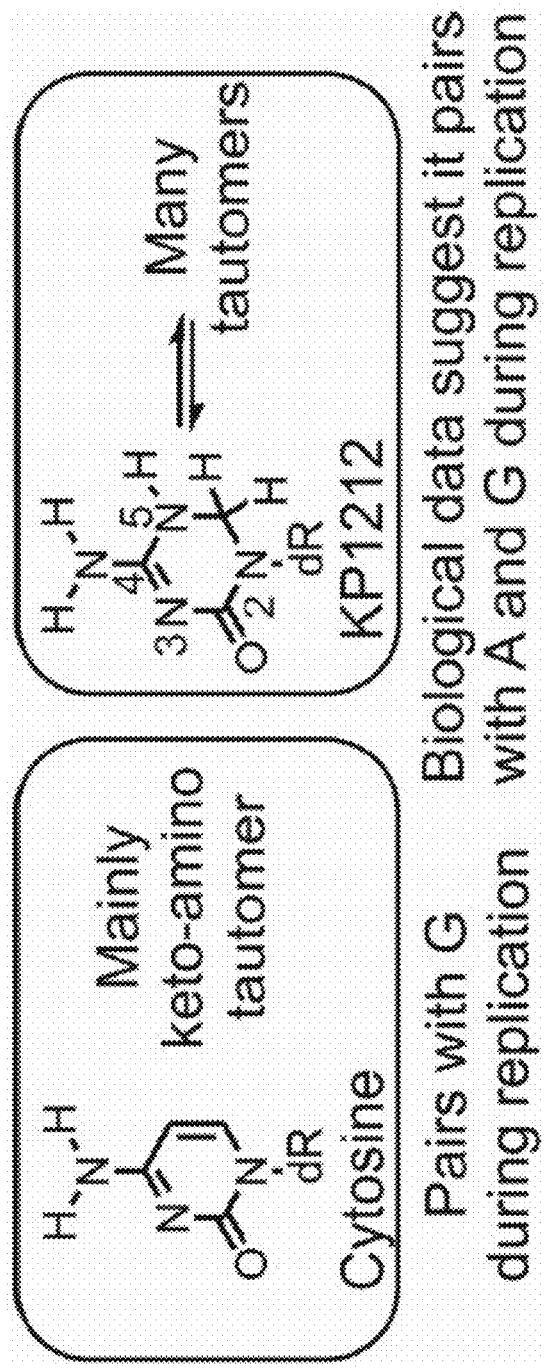
FIG. 13 shows exemplary schematic presentations of KP1212's mutagenic effect on viruses. (A) KP1212 exists as an array of different tautomeric forms, while cytosine almost exclusively exists as one form, the canonical keto-amino tautomer. (B) KP1212 is incorporated by viral polymerases, causing G to A and A to G mutations during viral replication. KP1212 is a poor substrate for human polymerases, which provides selectivity in its action against the virus. The progressive acquisition of mutations in the viral genome leads to viral population collapse.
Figure 13B:
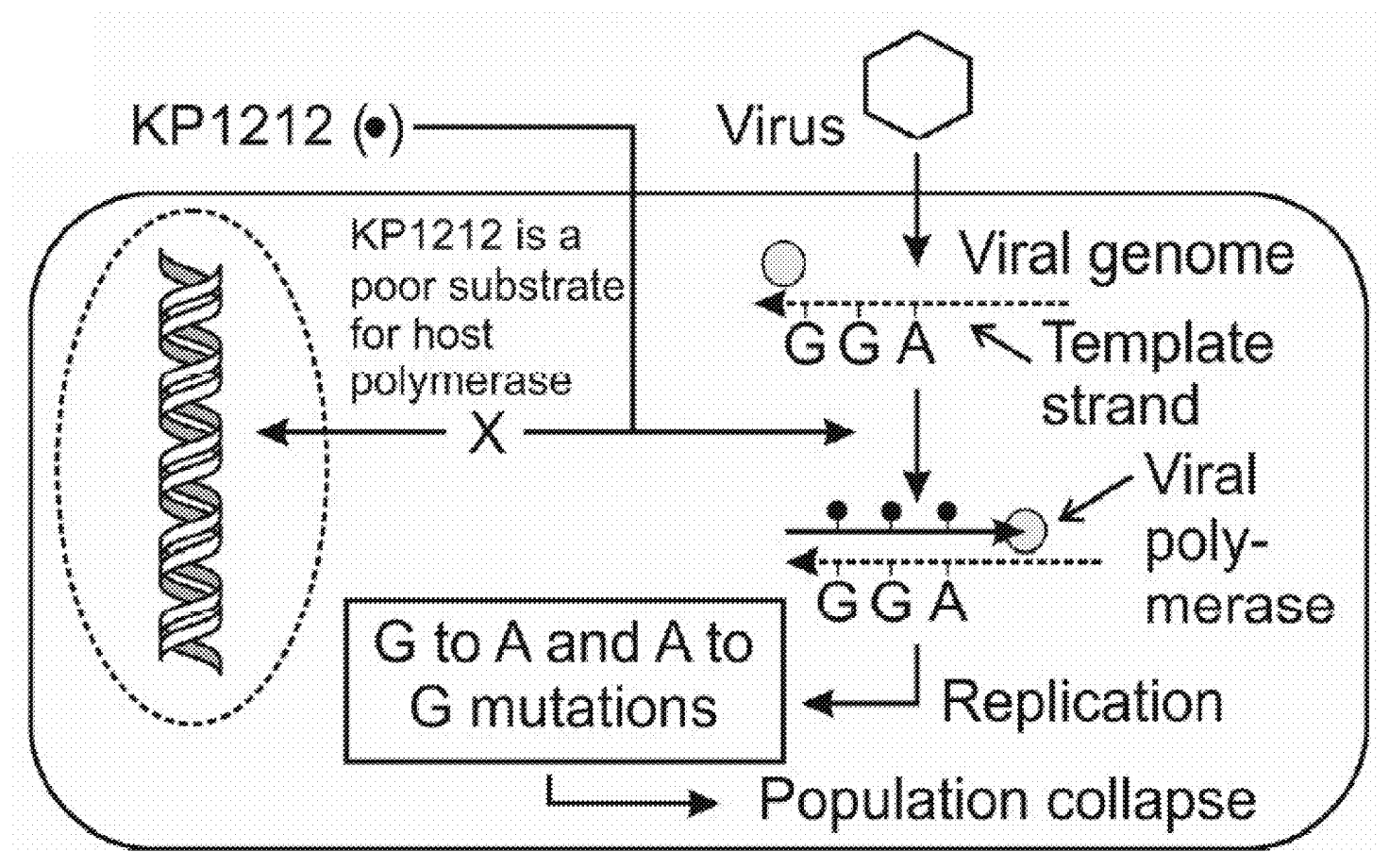

The mutagenic properties of KP1212 in cell culture reveal that it is likely to base-pair promiscuously with A and G, and that the progressive acquisition of mutations (primarily A to G and G to A transitions) precedes population collapse (FIG. 13B) (Harris, K. S., Brabant, W., Styrchak, S., Gall, A. & Daifuku, R. KP-1212/1461, a nucleoside designed for the treatment of HIV by viral mutagenesis. Antiviral Res. 67, 1-9

(2005)). These data are supported by biochemical experiments performed using purified polymerases that establish the ability of KP1212 to pair with either A or G, both when the modified base enters DNA from the nucleotide pool and when it acts as a template base (Murakami, E., Basavapathruni, A., Bradley, W. D. & Anderson, K. S. Mechanism of action of a novel viral mutagenic covert nucleotide: molecular interactions with HIV-1 reverse transcriptase and host cell DNA polymerases. Antiviral Res. 67, 10-17 (2005)). Understanding the chemical and structural basis of mutagenesis of this drug candidate is critical for both its future clinical progress and the development of new therapeutic agents that work by the principle of lethal mutagenesis.

Tautomerism of KP1212 leading to viral mutagenesis has been proposed to be the basis for the clinical activity of the drug candidate. There are, however, no direct data to support that view. In a search for a chemical rationale to explain the ambiguous pairing of KP1212 during replication, it was revealed that KP1212 adopts multiple tautomeric forms, some of which were unexpected. Using a battery of spectroscopic methods (1D, 2D and variable temperature NMR, FTIR and 2D IR) (Singh, V. et al. Direct observation of multiple tautomers of oxythiamine and their recognition by the thiamine pyrophosphate riboswitch. ACS Chem. Biol. In Press. (2013)), the array of tautomers exhibited by KP1212 were quantified and structurally characterized. Tautomer interconversion equilibria deconvoluted from NMR spectra provided data on the relative levels of tautomers in solution. In parallel with the spectroscopic studies, the qualitative and quantitative features of KP1212 mutagenesis were directly determined by inserting the KP1212 base into a single-stranded viral vector and measuring the intrinsic mutagenic properties of the base, both in vitro and in vivo. Finally, a model is proposed that correlates the mutagenic and clinical properties of KP1212 to its ability to exist as multiple tautomers.

NMR Spectroscopy Demonstrates the Existence of Multiple Tautomers of KP1212

Methods.

All NMR experiments were performed on Varian 500 MHz NMR spectrometers. The deuterated solvent DMF-$d_7$ was from Cambridge Isotope Laboratories, Andover, Mass., USA. 5-Aza-5,6-dihydro-2'-deoxycytidine (KP1212) nucleoside was from Berry & Associates Inc., Dexter, Mich., USA. The NMR sample was prepared by dissolving 10 mg of KP1212 nucleoside in 1.0 ml DMF-$d_7$ (final concentration ~44 mM). $^1$H NMR spectra were reported in parts per million (ppm) and were referenced to the signals for DMF-$d_7$ (8.03 ppm). $^{13}$C NMR spectra were referenced to the signals for DMF-$d_7$ (163.15 ppm).

Figure 14A:
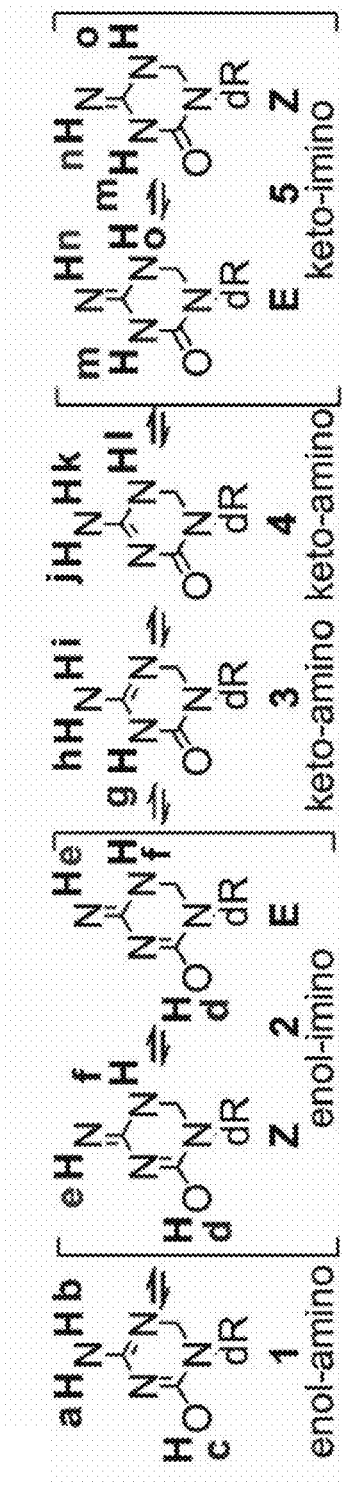
FIG. 14 shows exemplary $^1$H NMR results demonstrating the existence of different tautomeric forms of KP1212. (A) Structures of the five possible tautomeric forms of KP1212. The active protons (a-o) on the nucleobase portion of the molecule are grouped by their chemical environment (type): imino, amido, enol, and amino. (B) $^1$H NMR spectrum of KP1212 in DMF-$d_7$ at −50° C. (5.5 to 12.0 ppm). The peaks from the active protons on the nucleobase portion are labeled as i to vi and their corresponding areas are indicated. According to their chemical shifts, the type of the active protons on the KP1212 nucleobase that contribute to each peak is indicated. (C) Schematic of the deconvolution process of the $^1$H NMR spectrum of KP1212 at −50° C. depicting how the active proton peaks corresponding to each tautomer contribute to the overall spectrum. Each of the six peaks identified in the NMR spectrum in (B), denoted i to vi, is schematically represented as the bottom trace. To indicate each tautomer's respective contributions to the six peaks, schematic representations of the NMR signals of the active protons of each tautomer are shown. Each peak is labeled with a letter (a-o), which corresponds to the active protons labeled in (A). (D) Mathematical analysis of NMR spectrum using matrix algebra to calculate relative distribution of tautomers. The elements of matrix A represent the number of active protons from each tautomer (columns) that contribute to each of the six NMR peaks (rows). The matrix X elements are the unknown variables, which represent the relative amounts of each tautomer. Matrix B contains the areas corresponding to each peak in the NMR spectrum at −50° C. Linear equations were generated from the matrix equation A×X=B. Solving the system of linear equations yielded values for the unknowns, which provided the relative distribution of individual tautomers of KP1212.

KP1212 was studied by 1D, 2D and variable-temperature (VT) NMR techniques to investigate the presence of different tautomeric forms. Exemplary $^1$H and $^{13}$C chemical shift assignments of KP1212 are shown in Tables 5-7. FIG. 14A depicts the structures of all five possible tautomers (1 to 5) of KP1212, among which the three active protons on the nucleobase shift among the O2, N3, N4 and N5 positions. The NMR experiments were carried out in a solution of KP1212 in DMF-$d_7$; the solvent was chosen because it was aprotic, afforded good solubility of the compound and had a low freezing point (−61° C.). Before assigning the three active protons on the nucleobase moiety, all non-exchangeable protons in KP1212 and the two hydroxyl protons on the 3' and 5' positions were identified by carrying out 1D ($^1$H and $^{13}$C) and 2D (COSY, HSQC, and HMBC) NMR experiments. The NMR signals of the three active protons in the base portion of KP1212 were studied at different temperatures. At 20° C., the exchangeable protons on the KP1212 base (protons bound to either nitrogen or oxygen atoms on the base) displayed three broad peaks denoted 1, 2, and 3 in the bottom curve of FIG. 3.

When the temperature was decreased to −50° C., the three broad peaks resolved into six distinct proton resonances (FIG. 14B, denoted as peaks i-vi), which could be assigned to imino (designated as e and n in FIGS. 14A to 14C), amido (designated as g and m), enolic (designated as c and d) or amino (designated as a, b, f, h, i, j, k, l, and o) protons.

In the variable temperature NMR experiments of KP212, the signals from the imino protons could easily be separated from the enol and amino signals. However, the spectral information was not sufficient to distinguish between the imino protons of regioisomers 2Z and 2E (FIG. 14A) because the only difference between the two isomers is the configuration of the imino double bond. For the assignment of NMR signals, the isomers 2Z and 2E were treated as one species (2); similarly, the isomers 5E and 5Z were treated as one species (5) (FIG. 14A), According to the rules of keto-enol and amino-imino tautomerism of nucleic acid bases, five possible tautomers of KP1212 (FIG. 14A) were possible: enol-amino tautomer (form 1), enol-imino tautomer (form 2), keto-amino tautomer (form 3), keto-amino tautomer (form 4), and keto-imino tautomer (form 5).

At −50° C. six distinct proton resonances (FIG. 14B, i to vi) were observed, attributable to protons bound either to nitrogen or to oxygen atom (for only the base portion of the KP1212 molecule). Integration of the six broad peaks permitted estimation of the relative ratios of the five tautomeric species that exist in solution (FIG. 14A). Because each tautomer can generate only three discreet amino, imino, amido, and/or enol resonances, the observation of six proton resonances indicated the presence of multiple tautomeric forms of the KP1212 molecule in the solution state in DMF.

The total area of the six peaks is about 3.00, which corresponds exactly to the three active protons in the nucleobase of KP1212. By simulating the six peaks with Gaussian and Lorentzian functions and fitting the total areas to 3.00 (FIG. 16), the individual area of each peak was obtained (Table 7). The accuracy of those simulations could be achieved to about +1%. From the above analyses, the total area of the possible 15 active protons is 3.00. Each tautomer has three equivalent protons (which have equal integrated areas); adding together the proportions of the five tautomers should yield 1.00 or 100% in percentage.

Figure 15:
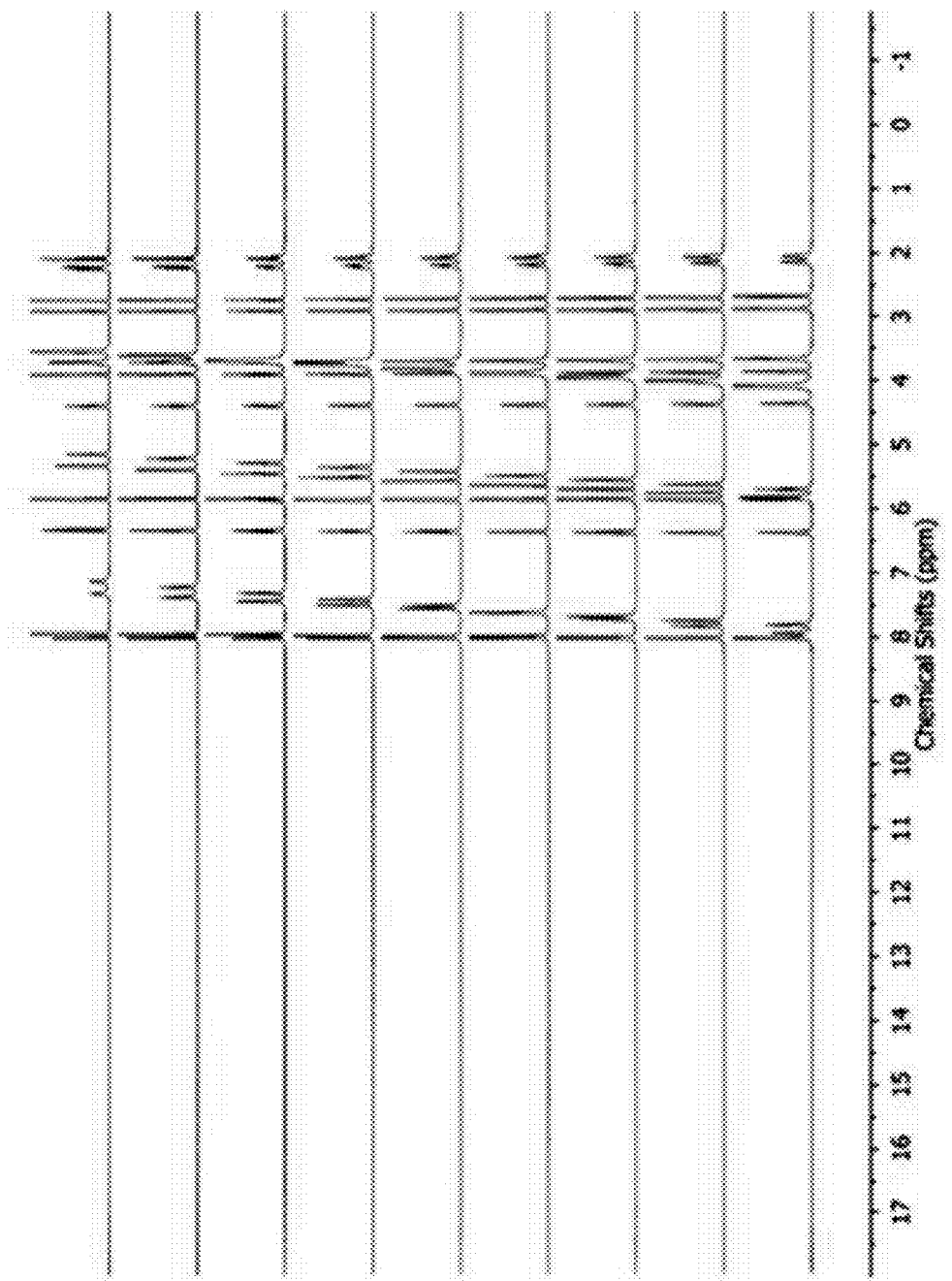
FIG. 15 shows exemplary variable temperature $^1$H NMR results of deoxycytidine in DMF-$d_7$ from 20 (top) to −60° C. (bottom) in 10° C. decrements. There is no signal above 8.5 ppm, which indicates no imino or enol tautomer exists under these conditions.

Because each tautomeric form has only a total of three exchangeable protons on the nucleobase, the observation of six proton resonances indicated the presence of a minimum of two tautomeric forms of KP1212. By contrast, the normal nucleoside deoxycytidine investigated under similar conditions displayed only one tautomeric form, the classical keto-amino tautomer (FIG. 13A) in DMF-$d_7$ over the same temperature interval (FIG. 15).

In the NMR spectrum of KP1212 in DMF-$d_7$ solution at −50° C., the chemical shifts for the imino/amido, enolic, and amino protons could be clearly differentiated. However, the imino proton signals corresponding to the Z and E geometric isomers of the imino tautomers (i.e., isomer 2Z versus 2E, or isomer 5Z versus 5E), were not separated by VT-NMR under the above conditions (FIG. 14A). Therefore, the subsequent quantification of the relative amounts of each tautomer from NMR data treated the imino geometric isomers together (i.e., 2Z & 2E together and 5Z & 5E together).

Figure 14B:
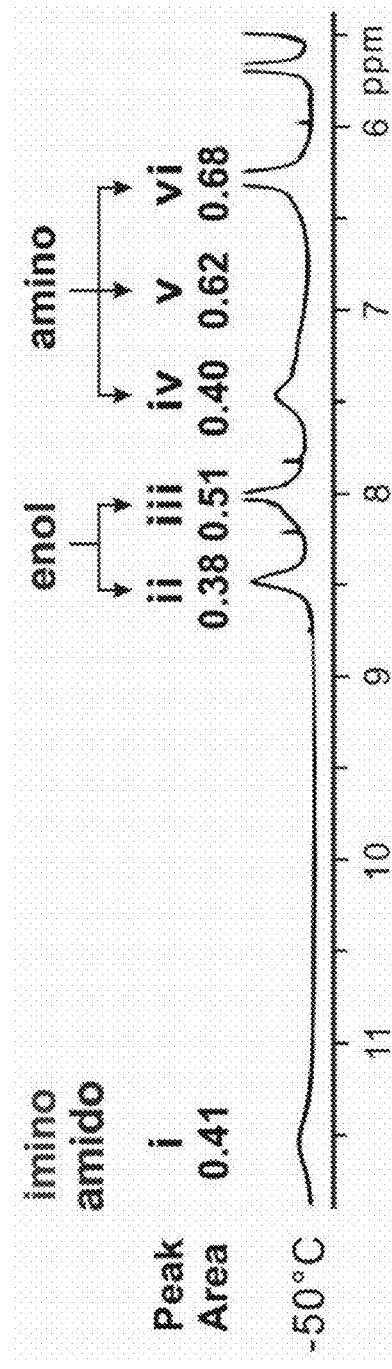
Figure 14C:
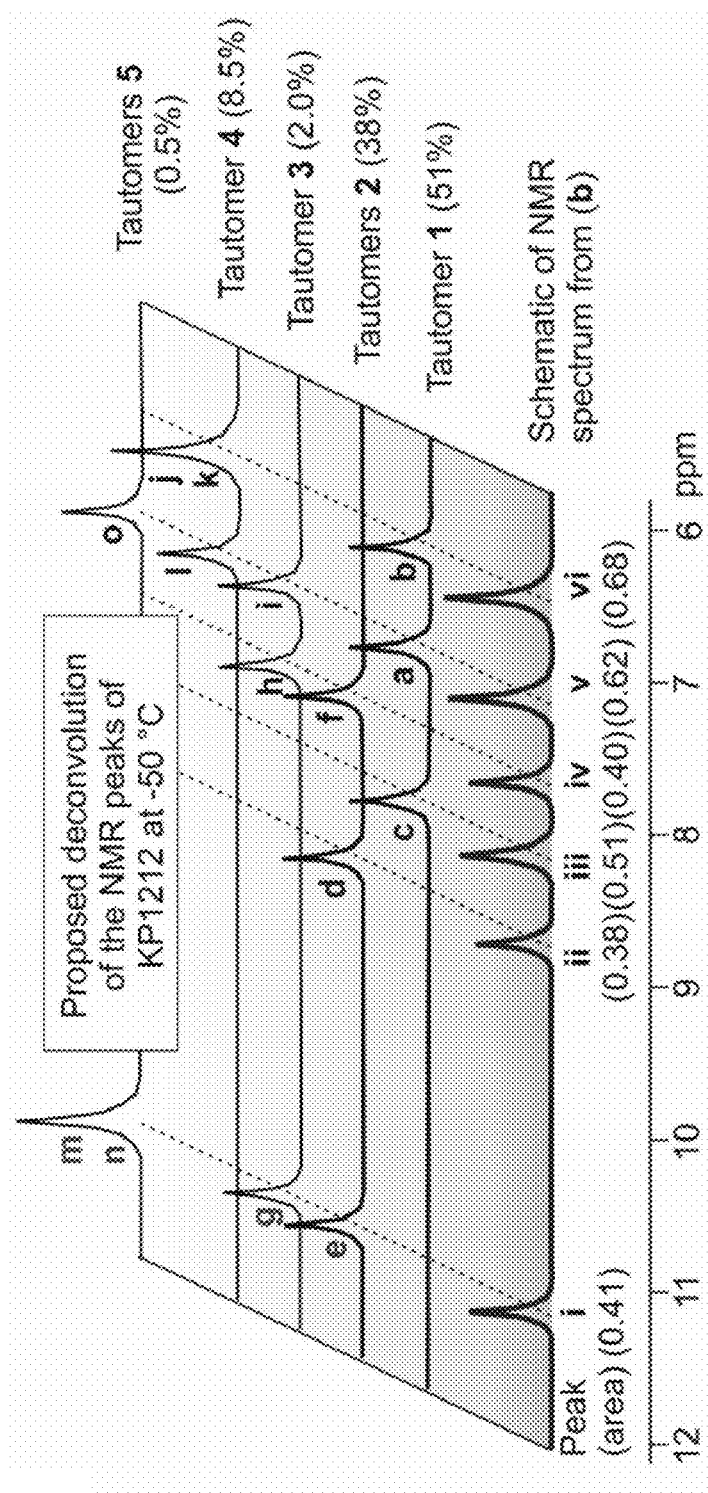
Figure 14D:
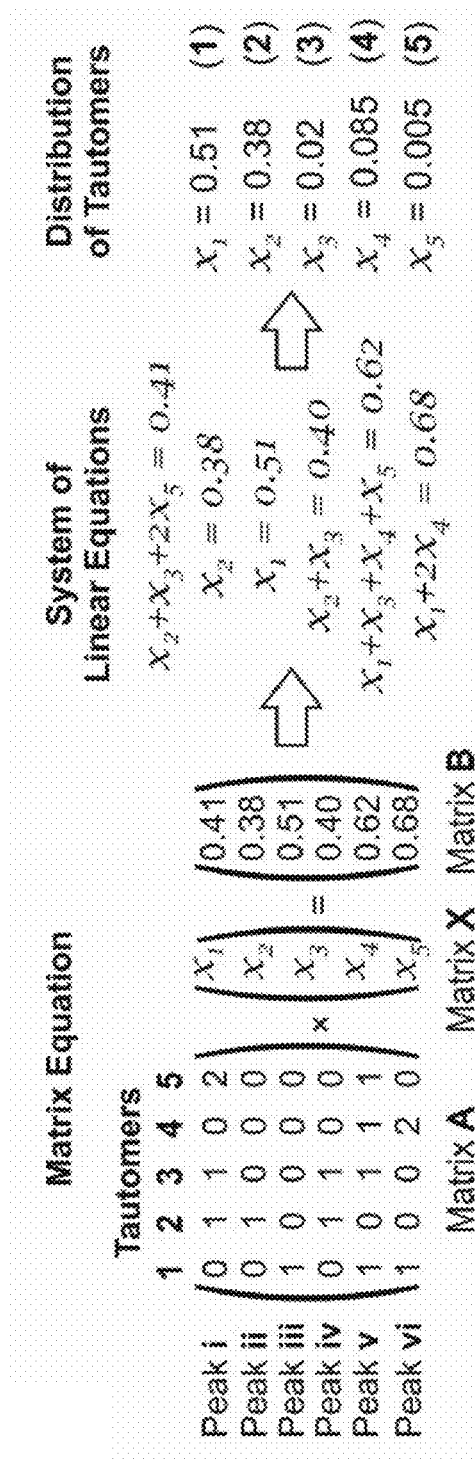
Figure 16:
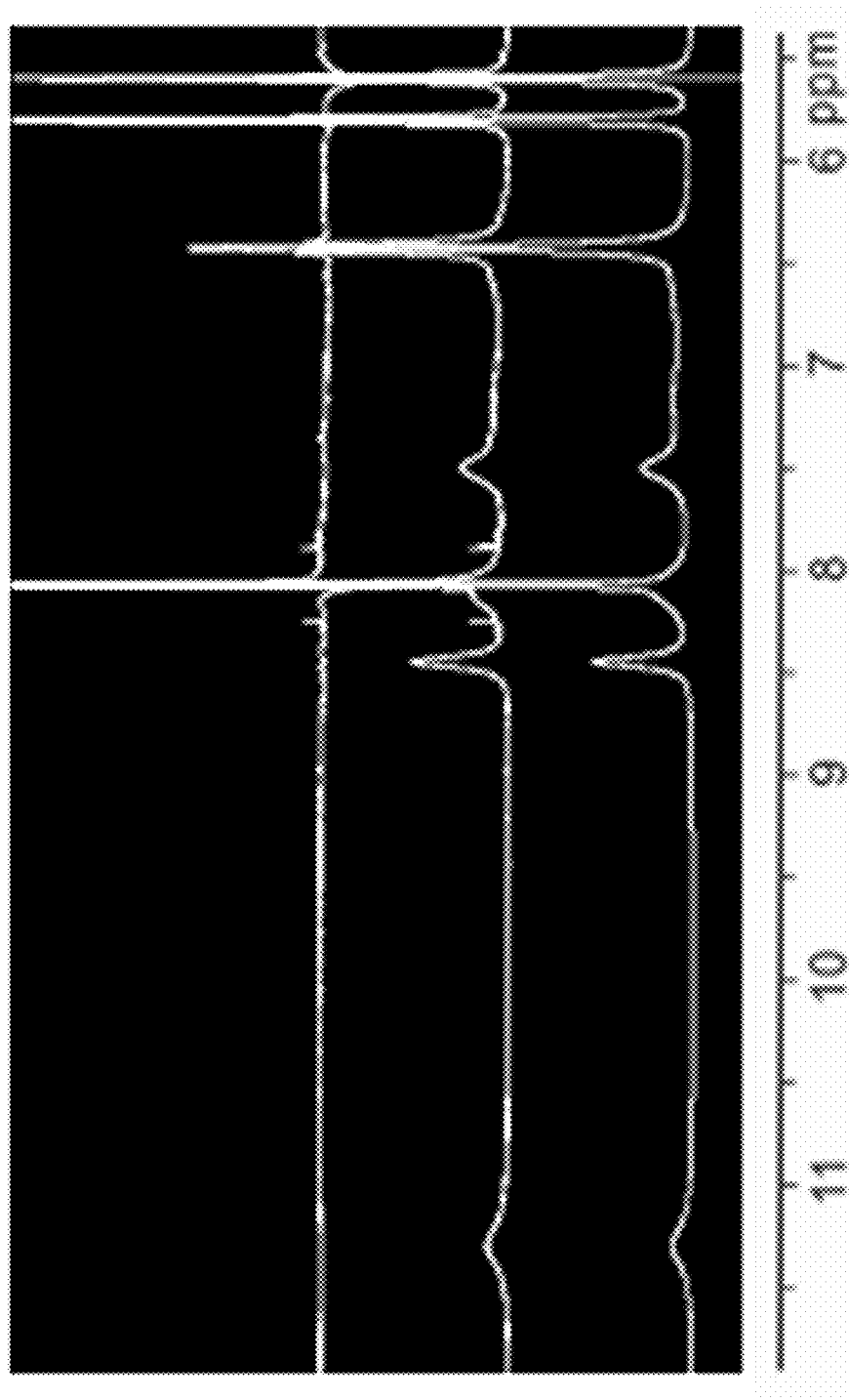
FIG. 16 shows exemplary simulated (bottom curve) and experimental (middle curve, 5.5 to 12.0 ppm) NMR spectra of KP1212 at −50° C. in DMF-$d_7$ and the difference spectrum (top curve) between the simulated and experimental spectra.

The NMR data also allowed the determination of the relative ratios of the tautomeric species present in the DMF solution at −50° C. (FIGS. 14B and 14C). Several peaks in the NMR spectrum partially overlapped (e.g., iv and v), so the raw data were reconstructed using a least squares fit algorithm (FIG. 16). The reconstructed peaks from the simulation were integrated, yielding an estimate of the relative amounts of each of the proton resonances in the spectrum. The deconvolution of the NMR spectrum was done in two steps: 1) each tautomer was analyzed for the types of protons (imino/enolic/ amido/amino) it contained on the nucleobase; this analysis revealed which of the 6 NMR peaks observed contained which of the proton signals from a given tautomer. 2) Based on the peak assignments from part 1), a system of linear equations was set up using the relative amounts of tautomers as unknown variables (FIG. 14D). The matrix form of this system is also shown in FIG. 14D. Each NMR peak provided a linear equation whereby the peak area should be equal to the sum of all tautomers (as relative amounts) containing protons that contribute to that peak. The solutions of these equations yielded the relative ratios of the tautomeric species present in DMF at −50° C. (FIG. 14D).

The unique solution of the system of equations presented above also served as a validation for the correct NMR assignment of different tautomer resonances. An exhaustive analysis was performed where other possible assignments were explored. However, in all other cases, the resulting system of linear equations either had no solution, or did not produce chemically sensible results (e.g., negative amounts of a given tautomer). Moreover, it was also investigated whether a smaller number of tautomers could explain the spectroscopic data. A comprehensive analysis showed that only when 5 tautomeric species are considered, the assignment becomes possible.

The relative proportions of the tautomeric species of KP1212 deconvoluted from the NMR spectrum highlighted some unique and non-obvious features of the molecule. Contrary to our expectations, the enol tautomers of KP1212 were found to be the dominant species at −50° C. in DMF (51% for 1, 38% for 2, FIG. 14C), while the keto tautomers 3 to 5 collectively constituted only 11% of the total mixture. By contrast, for normal DNA bases (such as cytosine), the keto tautomers are the major ones, while enol tautomers are very rare (Watson, J. D. & Crick, F. H. Genetical implications of the structure of deoxyribonucleic acid. Nature 171, 964-967 (1953); Miles, H. T. Tautomeric forms in a polynucleotide helix and their bearing on the structure of DNA. Proc. Natl. Acad. Sci. U.S.A. 47, 791-802 (1961)). Taken together, the NMR observations demonstrated the existence of various tautomeric forms of KP1212 in solution, suggesting a putative mechanistic basis for the observed mutagenic properties of KP1212.

IR Spectroscopy Establishes the Tautomeric Properties of KP1212 in Aqueous Solution Methods.

For both 1D FTIR and 2D IR experiments, the H/D exchanged KP1212 was dissolved at a concentration of 20 mg/ml (88 mM) in 0.5 M phosphate buffer pD (pH reading in $D_2O$) 7.9. About 25 μl of sample solution was sandwiched between two $CaF_2$ windows separated by a 50 μm TEFLON spacer. Variable-temperature FTIR spectra were collected using Nicolet 380 FTIR spectrometer at 1.0 $cm^{-1}$ resolution with 16 scans per spectrum. Spectra for both the sample and the $D_2O$ were collected with the same procedure and the solvent spectra were subtracted from the sample spectra.

Absorptive 2D IR spectra were collected using a 2D IR spectrometer as described in detail previously (Chung, H. S., Khalil, M., Smith, A. W. & Tokmakoff, A. Transient two-dimensional IR spectrometer for probing nanosecond temperature-jump kinetics. Rev. Sci. Instrum. 78, 063101 (2007)). The relative polarizations of the pulses were set to be perpendicular (ZZYY). The waiting time (τ2) between the first two pulses and the third pulse was fixed at 150 fs. The coherence time between the first and the second pulse was scanned in 4 fs steps from −60 fs to 2.8 ps and 2.0 ps for rephasing and non-rephasing spectra, respectively. The coherence time (τ1) was Fourier-transformed to obtain the first frequency axis ω1. The heterodyned signal was dispersed in a monochromator to obtain the ω3 frequency dimension and collected using a 64×2 pixel mercury-cadmium-telluride (MCT) array detector. Linear absorption from the solvent and solute was divided out along both the ω1 and ω3 axes to remove spectral distortions (Jones, K. C., Ganim, Z., Peng, C. S. & Tokmakoff, A. Transient two-dimensional spectroscopy with linear absorption corrections applied to temperature-jump two-dimensional infrared. J. Opt. Soc. Am. B 29, 118-129 (2012)).

While NMR spectroscopy demonstrated the presence of different tautomeric forms of KP1212, most of the measurements were carried out at low temperature, with the nucleoside dissolved in the non-aqueous solvent DMF. To probe whether KP1212 can also form multiple tautomers under more physiologically relevant conditions, variable temperature FTIR and 2D IR experiments were performed in $D_2O$ solutions of KP1212, buffered with deuterated potassium phosphate (0.5 M, pD=7.9). In the region of in-plane double bond vibrations for aromatic heterocycles (FIG. 17), vibrational bands from different tautomers are expected to have distinct patterns (Miles, H. T. Tautomeric forms in a polynucleotide helix and their bearing on the structure of DNA. Proc. Natl. Acad. Sci. U.S.A. 47, 791-802 (1961)). The vibrational mode at 1666 $cm^{-1}$ was assigned to the carbonyl stretch present in the KP1212 keto tautomers based on the characteristic vibrational frequency and the broad line-shape. Deoxycytidine is known to display a similar keto-carbonyl stretch at 1651 $cm^{-1}$ (Peng, C. S., Jones, K. C. & Tokmakoff, A. Anharmonic vibrational modes of nucleic acid bases revealed by 2D IR spectroscopy. J. Am. Chem. Soc. 133, 15650-15660 (2011)). However, compared to deoxycytidine at a similar concentration, the intensity of the KP1212 carbonyl stretch was clearly reduced, indicating a possible reduction in the population of keto tautomers and the presence of a significant enol tautomer population.

Figure 17:
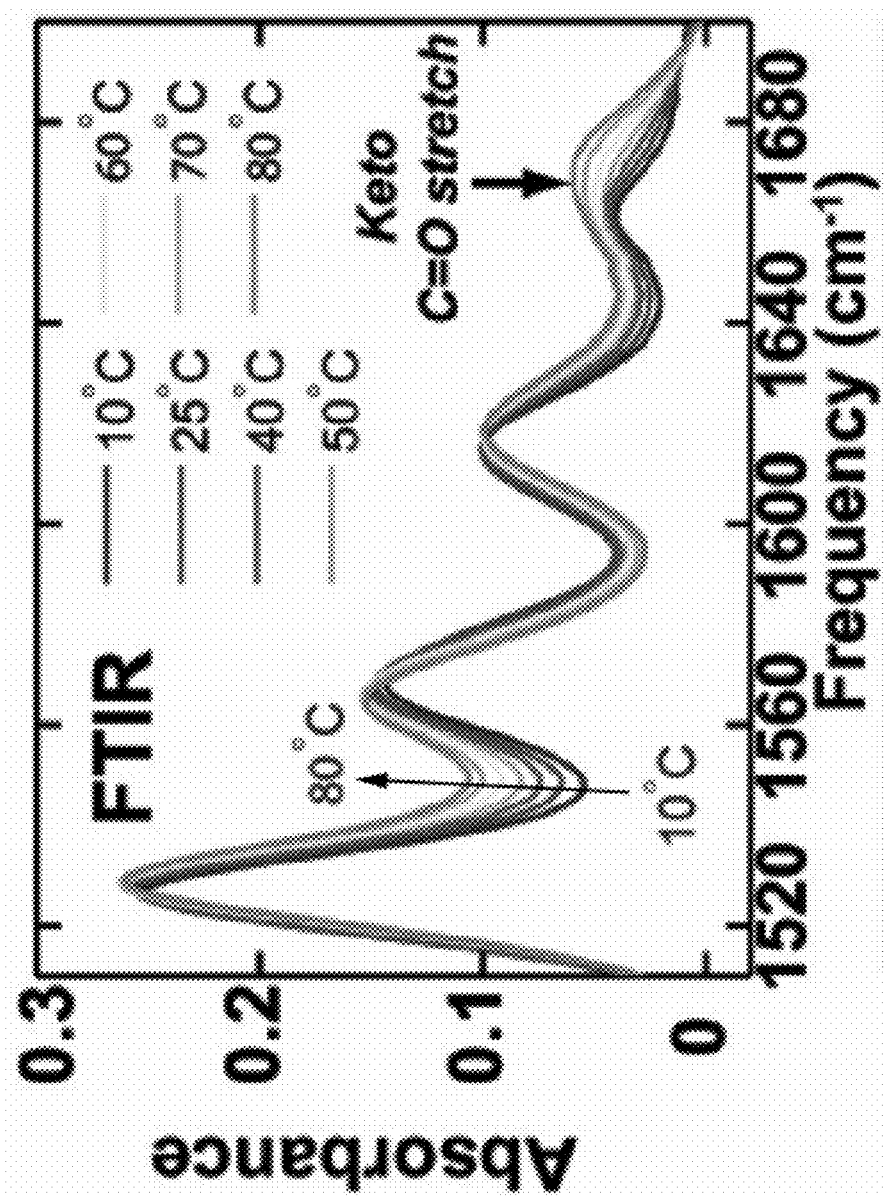
FIG. 17 shows exemplary IR results demonstrating the existence of different tautomeric forms of KP1212. Variable temperature FTIR spectra of KP1212 in deuterated 0.5 M phosphate phosphate buffer pD=7.9 were taken at various temperatures (10° C.-80° C., indicated by the arrow on the left-hand side). The arrow on the right-hand side indicates the temperature-dependent increase of the keto carbonyl stretch.

To provide further evidence of the existence of multiple tautomers, 2D IR spectra of KP1212 were recorded. 2D IR spectroscopy is analogous to 2D NMR: sequences of ultrafast IR pulses are employed to excite molecular vibrations, and the energy flow from one vibration to others is then detected. The correlation of excitation and detection frequencies allows mixtures of tautomers to be separated through the cross-peaks that encode their intramolecular vibrational couplings (Peng, C. S. & Tokmakoff, A. Identification of lactam-lactim tautomers of aromatic heterocycles in aqueous solution using 2D IR spectroscopy. J. Phys. Chem. Lett. 3, 3302-3306 (2012); Peng, C. S., Baiz, C. R. & Tokmakoff, A. Direct observation of ground-state lactam-lactim tautomerization using temperature-jump transient 2D IR spectroscopy. Proc. Natl. Acad. Sci. U.S.A. 110, 9243-9248 (2013)). The 2D IR spectrum of KP1212 showed intense cross-peaks among the three lower frequency diagonal peaks. However, no cross-peaks were detected between the C=O stretch peak and the other peaks, indicating that the 1666 $cm^{-1}$ mode and the lower frequency modes originated from two separate species, namely, keto and enol tautomers, respectively. The variable temperature IR data were also consistent with the 2D IR result. When the temperature was increased, the C=O peak intensity increased while some of the lower frequency modes decreased in intensity (FIG. 17). This result indicated that both keto and enol tautomeric forms were present in solution, in a thermodynamic equilibrium, and the proportion of the keto tautomeric form increased at elevated temperatures. Taken together, the IR data helped establish the presence of multiple tautomeric forms of KP1212 in aqueous solution at a physiological pH.

Example 4

DNA Polymerase Extension Assays Demonstrate the Mutagenic Properties of KP1212

Cell Strains.

All *E. coli* strains used in this work contain the F' episome, which enables infection by M13 phage. GW5100 strain was used for large scale preparation of M13 phage DNA, SCS 110 (JM110, endAl) was used for amplification of progeny phage post-electroporation, and NR9050 was the strain of choice for double agar plating with X-GAL for blue-clear detection of plaques. The *E. coli* strains used to replicate lesion-containing phage were HK81 (as AB1157, but nalA) and HK82 (as AB1157, but nalA alkB22; AlkB-deficient).

Oligonucleotide Synthesis.

All oligonucleotides and primers were obtained from Integrated DNA Technologies (IDT) unless otherwise specified. Oligonucleotides of the sequence 5'-GAAGACCTXG-GCGTCC-3' (SEQ ID NO: 1), where X is either KP1212 or m3C were synthesized and purified as previously described. DNA concentration was measured by UV absorbance using the extinction coefficients (E) at 260 nm For lesion-containing oligonucleotides, the extinction coefficient was approximated with that of an oligonucleotide containing normal C instead of KP1212 or m3C. Sixteen-mer oligonucleotides with the same sequence but with X=G, A, T, or C, were used as controls (SEQ ID NO: 1). The 19-mer 'competitor' oligonucleotide of the sequence 5'-GAAGACCTGGTAGCG-CAGG-3' (SEQ ID NO: 2) was used in the CRAB assay. Scaffold oligonucleotides (5'-GGTCTTCCACTGAAT-CATGGTCA TAC-3' (SEQ ID NO: 3) and 5'-AAAAC-GACGGCCAGTGAATTGGACGC-3' (SEQ ID NO: 4)) were used to align and ligate the 16-mers containing lesions into the EcoRI-cleaved single-stranded M13 vector during genome construction. The following primers were used to PCR-amplify the DNA of the progeny phage for the REAP and CRAB assays: 5'-YCAGCTATGACCATGATTCAGTG-GAAGAC-3' (SEQ ID NO: 5) (REAP and CRAB forward primer); 5'-YCAGGGTTTTCCCAGTCACGACGTTG-TAA-3' (SEQ ID NO: 6) (CRAB reverse primer); 5'-YTG-TAAAACGACGGCCAGTGAATTGGACG-3' (SEQ ID NO: 7) (REAP reverse primer). Y denotes an aminoethoxyethyl ether group present at the 5' ends to prevent their labeling with [γ-$^{32}$P]-ATP in subsequent reactions.

KP1212 or the m3C control lesion were incorporated into 16mer oligonucleotides (5'-GAAGACCTXGGCGTCC-3' (SEQ ID NO: 1), where X is the lesion or the guanine control) by using phosphoramidite solid-phase methods described before (Delaney, J. C. & Essigmann, J. M. Assays for determining lesion bypass efficiency and mutagenicity of site-specific DNA lesions in vivo. Meth. Enzymol. 408, 1-15 (2006); Delaney, J. C. & Essigmann, J. M. Mutagenesis, genotoxicity, and repair of 1-methyladenine, 3-alkylcytosines, 1-methylguanine, and 3-methylthymine in alkB *Escherichia coli*. Proc. Natl. Acad. Sci. U.S.A. 101, 14051-14056 (2004)). The phosphoramidites were from Berry & Associates Inc., Dexter, Mich., USA. The syntheses were done at the Keck Oligonucleotide Synthesis Facility, Yale School of Medicine, New Haven, Conn., USA.

Enzymes and Chemicals.

EcoRI, HaeIII, BbsI, HinFI, T4 DNA Ligase, T4 DNA polymerase, BSA, and their enzyme reaction buffers were from New England Biolabs. Shrimp alkaline phosphatase (SAP) was from Roche. P1 nuclease, 5-bromo-4-chloro-3-indolyl-beta-D-galactopyranoside (X-GAL) and isopropyl-P-D-1-thiogalactopyranoside (IPTG) were from Sigma Aldrich. OPTIKINASE was from Affymetrix. SEPHADEX G-50 Fine resin was from Amersham Biosciences. HYDROXY-LAPATITE resin, 19:1 acrylamide:bisacrylamide solution, and N,N,N',N'-tetra-methyl-ethylenediamine (TEMED) were from Bio-Rad. Phenol:chloroform:isoamyl alcohol (25:24:1; pH 8) was from Invitrogen. [γ-$^{32}$P]-ATP was from Perkin Elmer. ATP (cold) was from GE Healthcare Lifesciences.

Double Agar Overlay Plaque Method for Phage Analysis.

This method, adapted from Delaney et al. (Delaney, J. C. & Essigmann, J. M. Mutagenesis, genotoxicity, and repair of 1-methyladenine, 3-alkylcytosines, 1-methylguanine, and 3-methylthymine in alkB *Escherichia coli*. Proc. Natl. Acad. Sci. U.S.A. 101, 14051-14056 (2004)), was used for determining phage titers to ensure statistical robustness throughout the experiment, and in particular to insure that the electroporation of the constructed genomes produced a sufficient number ($10^5$-$10^6$) of initial events. This method was not used for mutational analyses. Briefly, a 1:6 dilution of a saturated overnight culture of NR9050 was grown in 2×YT medium for 1 h at 37° C. with aeration. A mixture of 300 μl of the dilute overnight culture, 10 μl IPTG (24 mg/ml), 25 μl of 1% thiamine, and 40 μl X-GAL (40 mg/ml in DMF) was added to 2.5 ml top agar maintained in a molten state at 52° C. The resulting mixture was used to plate both electroporated cells and appropriate dilutions of supernatants containing phage particles onto B-broth plates. These plates were allowed to solidify for 10 min at room temperature and then incubated overnight at 37° C. to obtain dark blue, light blue, or clear plaques.

M13 Phage DNA.

M13mp7(L2) phage single-stranded DNA starting material was isolated as follows. A well-isolated plaque from an M13 stock plated using the double agar overlay method was plugged using a sterile Pasteur pipette and vortexed in 1 ml LB, 200 μl of which was used to make a starter culture (grown overnight) by mixing with 10 μl of an overnight saturated culture of GW5100 cells in 10 ml LB. One milliliter of this phage starter culture was then used to inoculate GW5100 cells, which had been grown using 500 μl of an overnight saturated culture in 250 ml of fresh 2×YT medium for 2 h at 37° C. and shaken at 275 rpm. The inoculated culture was grown further for 8 h at 37° C. with aeration, after which the cells were pelleted and discarded. The supernatant was supplemented with 4% PEG 8000 MW and 0.5 M NaCl, which allowed the precipitation of the phage, over 24 h at 4° C. The phage were pelleted, resuspended in 5 ml TE pH 8, and extracted four times with 3 ml 25:24:1 phenol:chloroform: isoamyl alcohol. The aqueous phase was passed through a 0.5 g HYDROXYLAPATITE column (BioRad), washed with 5 ml TE, and eluted in 1 ml fractions with 12 ml of 0.16 M phosphate buffer. The DNA containing fractions were identified by spotting on an agarose gel plate containing ethidium bromide. The phosphate buffer in those fractions was then exchanged for TE by three washes in MICROSEP 100K spin dialysis columns (Pall Lifesciences). The DNA obtained was at a yield of >1 pmol/ml of 2×YT large culture, and was stored at −20° C. until further use.

Construction of Genomes.

The M13mp7(L2) phage features a hairpin structure that contains an EcoRI site, for easy linearization. Twenty pmol of M13 single-stranded DNA were linearized by incubation with 40 U of EcoRI for 8 h at 23° C. Scaffolds (25 pmol in 1 μl each) were annealed to the ends of the linearized genome by incubation at 50° C. for 5 min followed by cooling to 0° C. over 50 min. In addition, 30 pmol of each 16-mer oligonucleotide insert was 5' phosphorylated using 15 U of OPTIKINASE, in OPTIKINASE buffer supplemented with 1 mM ATP, at 37° C. for 1 h. The phosphorylated oligonucleotide was subsequently ligated into the linearized genome by incubation with 1 mM ATP, 10 mM DTT, 25 μg/ml BSA, and 800 U T4 DNA ligase for 8 h at 16° C. The powerful exonuclease activity of T4 DNA polymerase (0.25 U/pl, 4 h at 37° C.) was then used to degrade the scaffolds. Finally, the constructed M13 genome was purified by extraction with 100 μl 25:24:1 phenol:chloroform:isoamyl alcohol, followed by removal of residual phenol and salts using a QIAQUICK column (Qiagen). Recovery yields of 30-45% were obtained.

Genome Validation and Normalization.

The incorporation of lesion-containing oligonucleotides in M13 genomes was confirmed and the relative concentration of the constructed genomes was determined and normalized using the following procedure. A 10-fold molar excess of scaffolds (previously used in constructing the genomes) were annealed to about 0.35 pmol of each genome in 5 µl. The genomes were cleaved with 10 U of HinFI in the presence of 1 U SAP (which dephosphrylates the newly formed 5' ends) by incubating at 37° C. for 1 h followed by phosphatase inactivation at 80° C. for 5 min and a slow (0.2° C./sec) cooling down to 20° C. The 5' ends were then labeled at 37° C. for 1 h with 1.66 pmol [γ-$^{32}$P]-ATP (6000 Ci/mmol) in a 12 µl reaction containing NEBuffer 2, 5 mM DTT, 150 pmol cold ATP, 5 U OPTIKINASE and 10 U HaeIII. After quenching the reaction with 12 µl Maxam-Gilbert loading dye (98% formamide, 10 mM EDTA, 0.025% bromophenol blue and 0.025% xylene cyanol FF), the products were resolved using 20% denaturing PAGE until the xylene cyanol dye migrated a distance of 12 cm. The bands corresponding to fully-ligated genomes were then quantified using phosphorimagery and normalized with respect to one another. The genomes were then diluted to the same final concentration. The band generated from the competitor genome was used as a marker.

Post-normalization, a test electroporation was performed in HK81 electrocompetent cells using the control genome mixed in different ratios with the competitor genome. The results of the test electroporation were determined by plating the cells immediately after electroporation using the phage-overlay method to yield a dark blue (control):light blue (competitor) plaque count ratio. The ratio that yielded a 80:20 dark blue:light blue phage count was selected as the formulation ratio for the bypass assay of the lesion-containing genomes.

Preparation of Electrocompetent Cells.

A saturated overnight culture of the desired strain was diluted 1:100 in LB medium and grown at 37° C. with shaking at 275 rpm until it reached early log phase ($OD_{600}$ about 0.4-0.5), typically 2-3 h. The cells were then pelleted by centrifugation at 9500 rpm (Sorvall GSA rotor), resuspended and washed three times with 175 ml cold sterile water, and finally resuspended in a minimal volume of 10% glycerol. Four hundred ml culture typically yielded 5 ml of electrocompetent cells, which were aliquoted and stored at −80° C. prior to use.

Lesion Bypass (CRAB), and Mutagenesis (REAP), and In Vitro Replication Assays.

Lesion-containing genomes were mixed with the competitor genome (80:20 molar ratio) and electroporated in triplicate into 100 µl competent cells using a 2 mm-gap cuvette and a BTX electroporator set to 2.5 kV and 125 a Typical pulse lengths were 4.9 msec. The cells were immediately transferred to 10 ml LB and an aliquot was immediately plated using the agar overlay method to verify that a minimum of $10^5$ independent initial electroporation events occurred in 10 ml of culture. Incubation for 6 h at 37° C. with aeration generated the progeny phage, which were then reamplified in SCS 110 cells (10 µl overnight culture and 100 µl of the 6 h supernatant in 10 ml LB) to dilute out the residual genomic DNA used for electroporation. Single-stranded M13 progeny phage DNA was isolated from 1.4 ml of supernatant using a Q1Aprep Spin M13 Kit with final DNA suspension in 100 µl elution buffer. CRAB forward and reverse primers were used to amplify the region of interest from 15 µl per Q1Aprep elution sample in a total volume of 25 µl containing 50 pmol of each primer, 1×Pfu Turbo buffer, 1.25 U Pfu Turbo DNA polymerase and 25 mM of each dNTP. The PCR program used 30 cycles of 67° C. (1 min) annealing and 72° C. (1 min) extensions. After purification using QIAQUICK PCR purification columns, 4 µl of the PCR product were treated with BbsI (1.5 U) and SAP (0.3 U) in a total volume of 6 µl by incubating at 37° C. for 4 h. After phosphatase inactivation, (80° C. for 5 min), the 5' ends were then radiolabeled using [γ-$^{32}$P]-ATP (1.66 pmol, 10 µCi/µl, 6000 Ci/mmol), cold ATP (16 pmol) and 5 U of OPTIKINASE at 37° C. for 30 min. Following the kinase inactivation at 65° C. for 20 min, the labeled product was then trimmed by HaeIII (10 U in a final volume of 10 µl) at 37° C. for 2 h, and diluted 1:1 in formamide loading dye. PAGE separation on a 20% denaturing gel, run for about 3.5 h at 550 V, until the xylene cyanol dye migrated 10.5 cm, yielded two bands for each sample: an 18-mer originating from the lesion-containing genome and a 21-mer originating from the competitor genome. The gels were visualized on a phosphorimager (Typhoon 7000, GE Healthcare Life Sciences); the band intensities were quantified using IMAGEJ software (National Institutes of Health). Lesion bypass was calculated as the percentage ratio of the intensity of the 18-mer band (lesion signal) to the intensity of the 21-mer band (competitor signal).

The REAP assay methodology is identical to the CRAB assay except for the PCR primers, which amplified only the progeny DNA originating from the lesion-carrying genomes. Following electrophoresis, the 18-mer bands were excised from the gel, crushed and extracted with 200 µl water. After desalting with SEPHADEX G-50 Fine resin spin columns, the samples were lyophilized to dryness, resuspended in 5 µl containing 1 µg P1 Nuclease in 30 mM sodium acetate (pH 5.3) and 10 mM zinc chloride, and incubated at 50° C. for 1 h. One µl of each sample was then spotted onto PEI-TLC plates and separated using 200 ml of a saturated solution of $(NH_4)_2HPO_4$ adjusted to pH 5.8. After 24 h of development, the TLC plates were air-dried and quantified using phosphorimagery.

The single-stranded, lesion-containing genomes, constructed above were also used as templates for in vitro polymerase extension assays. Fifty fmol of each genome were mixed with 50 pmol of REAP forward and reverse primers, 1.25 U Pfu Turbo DNA polymerase and 5 nmol of each dNTP in 1×Pfu Turbo buffer. The first cycle of a PCR program (annealing at 67° C., extension at 72° C.) allowed the Pfu Turbo polymerase to synthesize the complementary strand and place a base opposite the lesion. As replication occurs at 72° C. and Pfu Turbo is one of the most accurate polymerases known, possessing a robust 3'-5' exonuclease activity for proofreading, this assay captures the most stringent intrinsic base-pairing preference of the DNA lesion. Subsequently, 29 PCR cycles amplified the newly formed strand and generated a product that was then analyzed using the exact downstream steps of the REAP assay described above.

For the in vivo toxicity and mutagenicity studies, the oligonucleotides were ligated into an M13mp7(L2) single-stranded viral genome by using reported methods (Delaney, J. C. & Essigmann, J. M. Assays for determining lesion bypass efficiency and mutagenicity of site-specific DNA lesions in vivo. Meth. Enzymol. 408, 1-15 (2006); Delaney, J. C. & Essigmann, J. M. Mutagenesis, genotoxicity, and repair of 1-methyladenine, 3-alkylcytosines, 1-methylguanine, and 3-methylthymine in alkB *Escherichia coli*. Proc. Natl. Acad. Sci. U.S.A. 101, 14051-14056 (2004)). The viral genomes were then electroporated into *E. coli* strains HK81 (as AB1157, but nalA) and HK82 (as AB1157, but nalA alkB22; AlkB-deficient), or used as templates for in vitro polymerase extension studies. Lesion toxicity was measured using the CRAB assay and mutational analysis was performed by using the REAP assay (Delaney, J. C. & Essigmann, J. M. Assays for determining lesion bypass efficiency and mutagenicity of site-specific DNA lesions in vivo. Meth. Enzymol. 408, 1-15 (2006)).

Figure 18A:
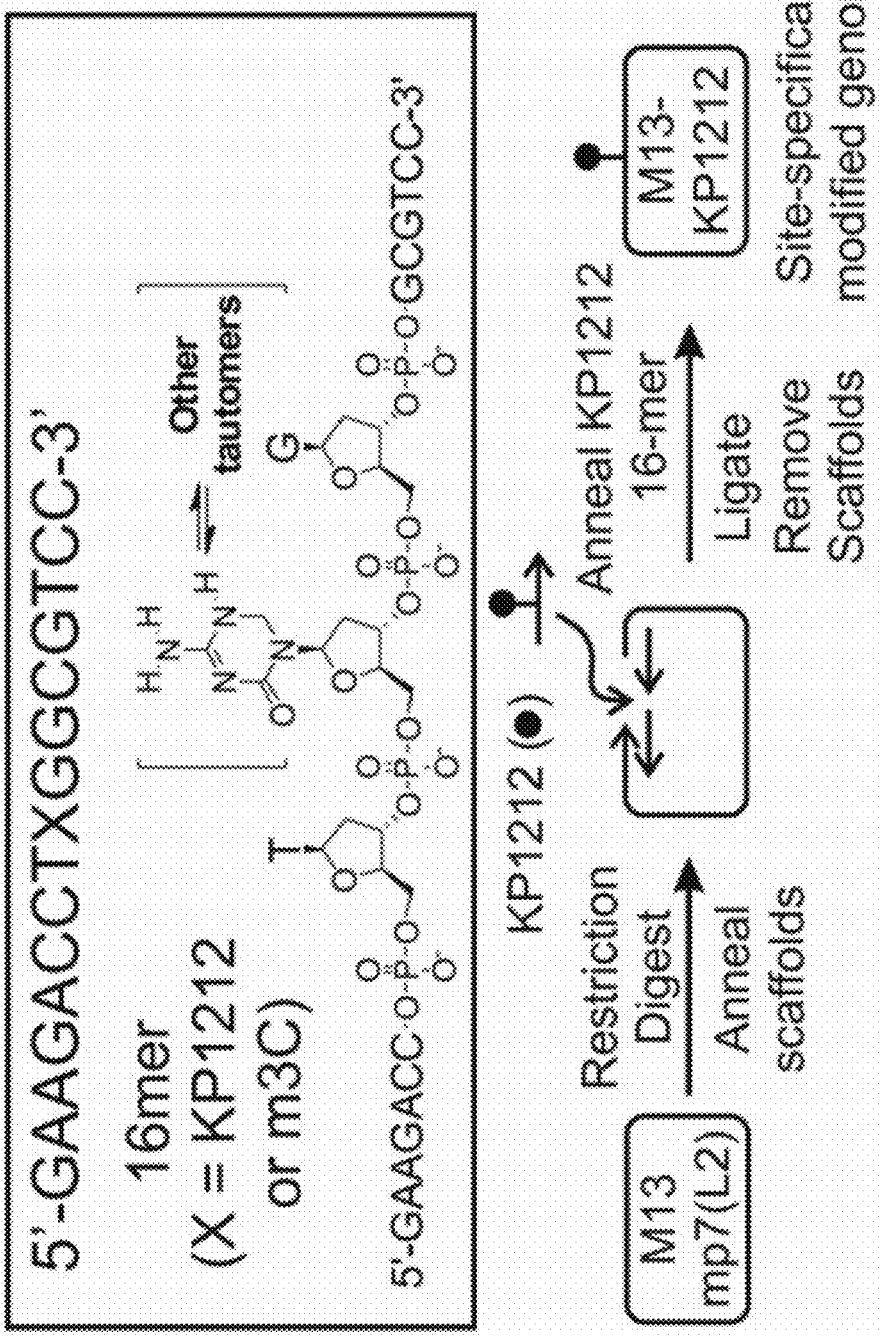
FIG. 18 shows exemplary in vivo and in vitro demonstration of the promiscuous base-pairing properties of KP1212. (A) A 16mer oligonucleotide containing KP1212 (SEQ ID NO: 1) (or controls) at a specific site was chemically synthesized and ligated into the genome of an M13 bacteriophage. (B) The KP1212-containing M13 genomes were replicated within *E. coli* cells. Progeny were analyzed to characterize the amount and the type of nucleic acid base placed opposite the lesion during replication. The relative reduction in lesion vs. non-lesion competitor progeny formation was used as an estimate of the extent to which KP1212 and m3C inhibited DNA replication. (C) The KP1212-containing M13 genomes were used as templates for in vitro polymerase extension assays, carried out at 72° C., using the high-fidelity DNA polymerase PfuTurbo. (D) Bypass efficiency (CRAB assay) of KP1212, m3C, C in HK81 (AlkB$^+$) and HK82 (AlkB$^-$) *E. coli* cells. m3C and undamaged C were used as controls. Genomes were made and normalized to one another before being combined with a competitor genome. Each mixture was transformed into the corresponding cell strain in triplicate, and bypass efficiency was calculated by using the undamaged C genome as 100% bypass, with error bars representing one standard deviation. (E) Mutagenesis (REAP assay) of KP1212, m3C, and C in HK82 (AlkB$^-$) *E. coli* cells. m3C, undamaged C, and an approximately equimolar mixture of genomes carrying unmodified G/A/T/C bases at the site of inquiry (denoted as GATC) were used as controls. Genomes containing the lesions of interest were transfected into *E. coli* in triplicate. The percentage of G, A, T, and C incorporated opposite the lesion site reveals the base-pairing preference of the lesions, with error bars representing one standard deviation.
Figure 18B:
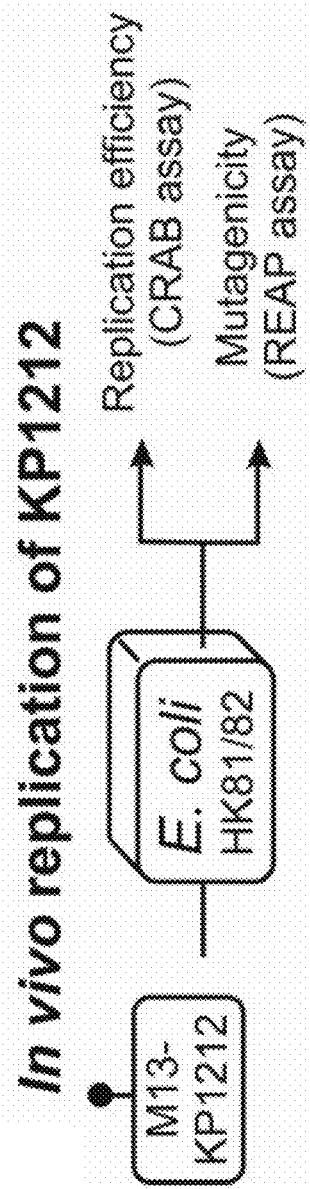

The base-pairing preferences of KP1212 were analyzed in vitro and in living cells. A DNA template containing a single KP1212 was constructed (FIGS. 18A to 18C) and used to determine the amount and type of the opposing-strand base(s) placed by polymerases across from KP1212. In addition, the extent to which KP1212 present in the template strand acted as a replication block was determined.

Mutagenicity and toxicity studies were performed by using methods established in reported work, where a single nucleoside (in this case, KP1212) was incorporated at a defined site in the single-stranded DNA circular genome of an M13 virus (Delaney, J. C. & Essigmann, J. M. Assays for determining lesion bypass efficiency and mutagenicity of site-specific DNA lesions in vivo. Meth. Enzymol. 408, 1-15 (2006); Delaney, J. C. & Essigmann, J. M. Mutagenesis, genotoxicity, and repair of 1-methyladenine, 3-alkylcytosines, 1-methylguanine, and 3-methylthymine in alkB Escherichia coli. Proc. Natl. Acad. Sci. U.S.A. 101, 14051-14056 (2004)). This viral genome was used as a template both for in vitro polymerase extension assays and, for the in vivo assays, as a vector that was replicated in E. coli hosts. The experimental system was specifically designed to avoid certain DNA repair processes, because KP1212 was present in a single-stranded genome. Most glycosylases acting in the base excision repair pathway, as well as the enzymes of the nucleotide excision repair pathway require double stranded DNA substrates (Friedberg, E. C. DNA repair and mutagenesis 2nd ed. (ASM Press, 2006)).

Figure 18C:
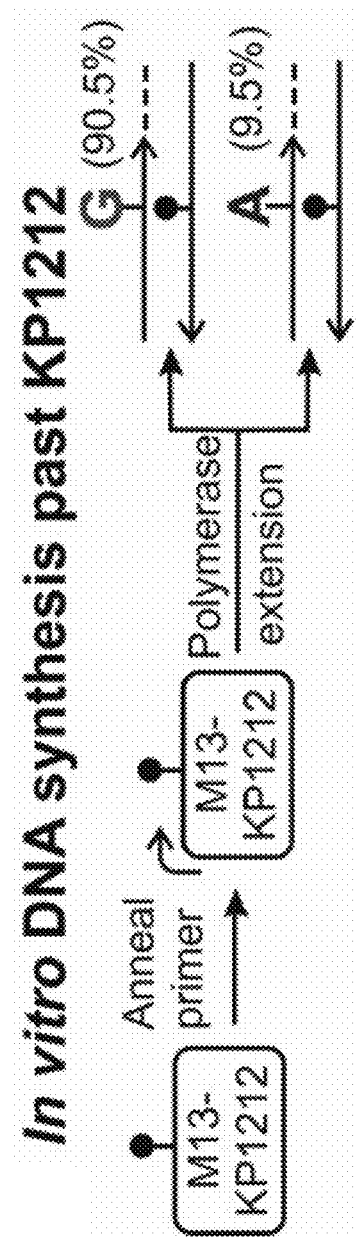
Figure 18D:
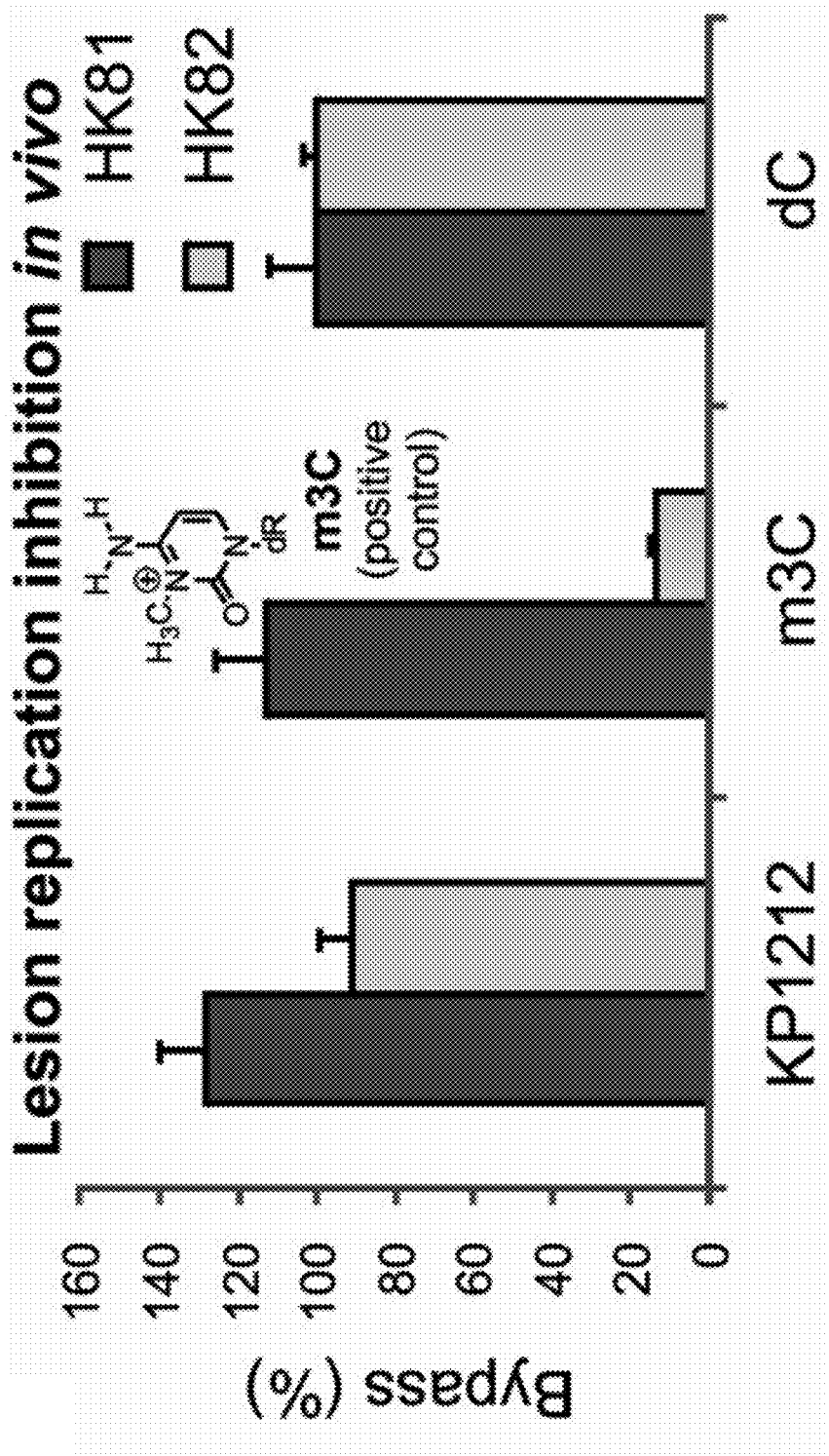
Figure 18E:
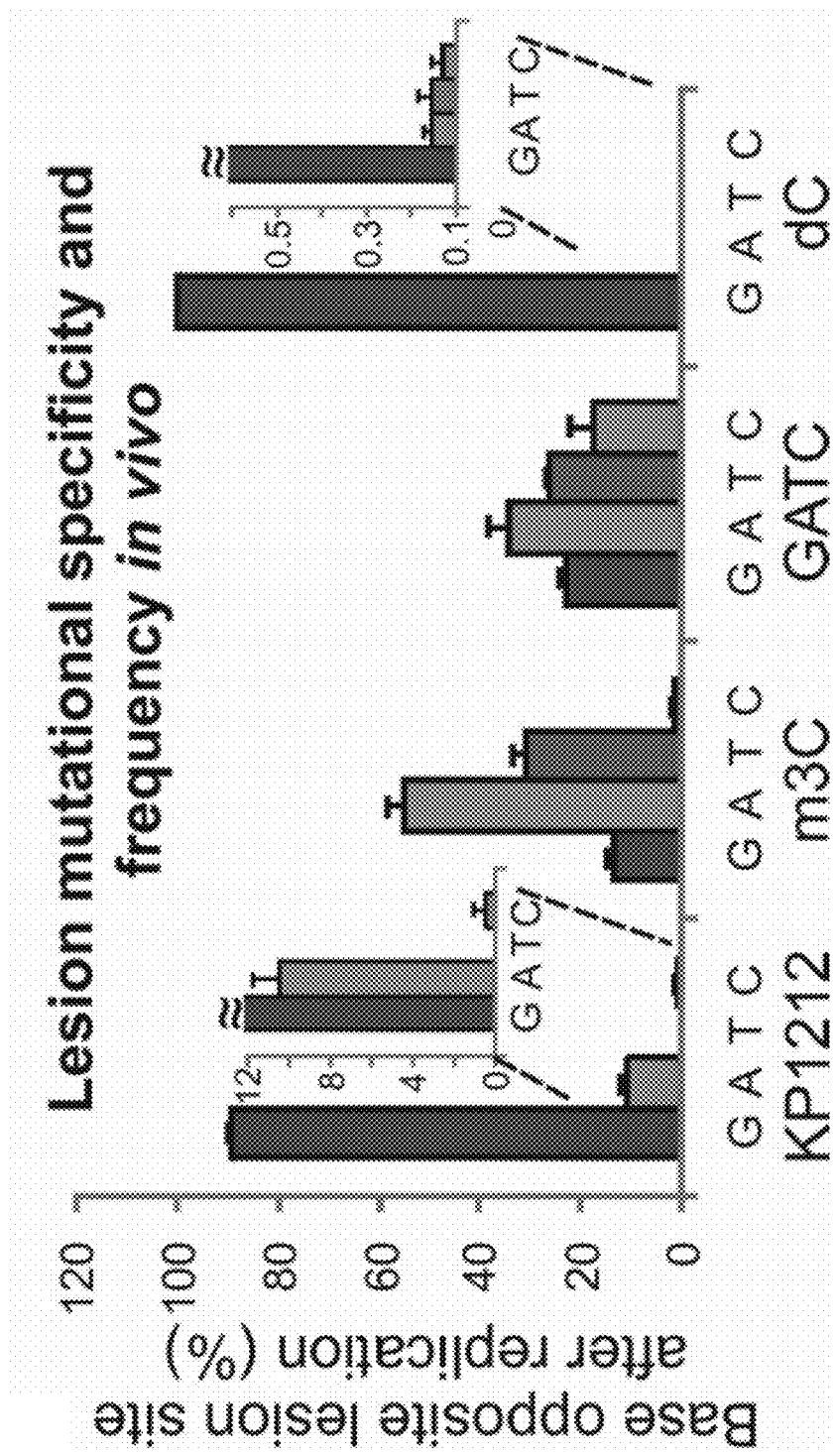

KP1212 was found not to be a replication block in E. coli (FIG. 18D). In this experiment, 3-methylcytosine (m3C), an established toxic and mutagenic DNA lesion (Delaney, J. C. & Essigmann, J. M. Mutagenesis, genotoxicity, and repair of 1-methyladenine, 3-alkylcytosines, 1-methylguanine, and 3-methylthymine in alkB Escherichia coli. Proc. Natl. Acad. Sci. U.S.A. 101, 14051-14056 (2004)), was used as a positive control. As expected, the data showed that m3C was very toxic to replication in cells that lack AlkB (an enzyme that repairs m3C) and that toxicity was abolished in cells that expressed the repair enzyme for the lesion (Delaney, J. C. & Essigmann, J. M. Mutagenesis, genotoxicity, and repair of 1-methyladenine, 3-alkylcytosines, 1-methylguanine, and 3-methylthymine in alkB Escherichia coli. Proc. Natl. Acad. Sci. U.S.A. 101, 14051-14056 (2004)). By comparison with m3C, KP1212 was not a replication block, but it was mutagenic both in vitro and in vivo (FIGS. 18C, 18E and Tables 3 and 4). Once again, m3C was the positive control and its mutagenicity in repair deficient cells was clearly evident (FIG. 18E). Consistent with previous reports, m3C was found to mispair with both A and T (Delaney, J. C. & Essigmann, J. M. Mutagenesis, genotoxicity, and repair of 1-methyladenine, 3-alkylcytosines, 1-methylguanine, and 3-methylthymine in alkB Escherichia coli. Proc. Natl. Acad. Sci. U.S.A. 101, 14051-14056 (2004)). By contrast with the dC control, which only pairs with G, KP1212 was shown to pair in vivo with both G (90%) and A (10%) (FIG. 18E). Given that KP1212 is a cytosine analog, and therefore expected to pair with G, the mutation frequency of KP1212 can be defined as the frequency with which it paired with any non-G base, in this case A. Therefore, KP1212 has an in vivo mutation frequency of approximately 10%. To rule out the indirect effects that the cellular environment might have on the mutagenicity of KP1212 (e.g., DNA repair or metabolism), the template containing KP1212 was also replicated in vitro, at 72° C. using PfuTurbo DNA polymerase. The reaction conditions (high temperature and a high-fidelity polymerase containing a powerful "proofreading" 3'-exonuclease) were specifically chosen to capture only the intrinsic base-pairing properties of KP1212. The results of the in vitro experiment indicated that G was placed opposite KP1212 90.5% of the time, while A was placed opposite of KP1212 9.5% of the time (FIG. 18C). These data were nearly identical to the ones observed in the in vivo experiment. Taken together, the polymerase extension assays established that: 1) KP1212 is mutagenic in living cells, by pairing with both A and G, and 2) the mispairing properties of KP1212 are intrinsic to the base.

TABLE 3

Polymerase bypass efficiencies (reported as a percentage relative to unmodified G) of C, KP1212, and m3C as determined by the CRAB assay. The data tabulated below are also shown in FIG. 18D.

| Lesion | HK82 | | HK82SOS | | HK81 | |
|---|---|---|---|---|---|---|
| | Avg. | Std. Dev. | Avg. | Std. Dev. | Avg. | Std. Dev. |
| C | 100% | 4% | 100% | 16% | 100% | 12% |
| KP1212 | 91% | 9% | 124% | 14% | 128% | 11% |
| m3C | 14% | 1% | 45% | 4% | 113% | 12% |

Avg.: average.
Std. Dev.: standard deviation.

TABLE 4

Mutagenicity of C, KP1212, GATC, and m3C as determined by the REAP assay. The data tabulated below in part (a) are also shown in FIG. 18E.

| Lesion/base | Average | | | | Standard deviation | | | |
|---|---|---|---|---|---|---|---|---|
| | % G | % A | % T | % C | % G | % A | % T | % C |
| (a) HK82 | | | | | | | | |
| C | 0.0 | 0.0 | 0.0 | 100.0 | 0.0 | 0.0 | 0.0 | 0.0 |
| KP1212 | 0.4 | 0.0 | 10.5 | 89.1 | 0.6 | 0.0 | 1.3 | 1.0 |
| m3C | 1.3 | 30.6 | 54.9 | 13.2 | 0.6 | 3.0 | 3.7 | 1.8 |
| GATC | 17.2 | 25.8 | 34.4 | 22.6 | 4.8 | 1.0 | 3.5 | 1.6 |
| (b) HK82-SOS | | | | | | | | |
| C | 0.0 | 0.1 | 0.0 | 99.9 | 0.0 | 0.0 | 0.0 | 0.1 |
| KP1212 | 0.2 | 0.1 | 10.3 | 89.4 | 0.2 | 0.1 | 3.1 | 32 |
| m3C | 3.2 | 33.6 | 57.5 | 5.7 | 1.3 | 1.4 | 19 | 2.6 |
| GATC | 20.5 | 29.5 | 33.1 | 16.9 | 0.6 | 0.4 | 0.7 | 0.3 |
| (c) HK81 | | | | | | | | |
| C | 0.0 | 0.1 | 0.0 | 99.9 | 0.0 | 0.1 | 0.0 | 0.1 |
| KP1212 | 0.1 | 0.2 | 9.5 | 90.2 | 0.0 | 0.1 | 0.3 | 0.2 |
| m3C | 0.0 | 0.0 | 0.0 | 100.0 | 0.0 | 0.0 | 0.0 | 0.0 |
| GATC | 20.8 | 32.8 | 31.6 | 14.8 | 1.9 | 0.8 | 0.9 | 2.5 |

Multiple tautomeric forms of canonical nucleic acid bases have long been thought to exist and to be the basis for spontaneous mutations (Kunkel, T. A. DNA replication fidelity. J. Biol. Chem. 279, 16895-16898 (2004); Watson, J. D. Molecular biology of the gene 6th ed. (Pearson/Benjamin Cummings; Cold Spring Harbor Laboratory Press, 2008); Goodman, M. F. DNA models. Mutations caught in the act. Nature 378, 237-238 (1995); Lowdin, P.-O. Proton tunneling in DNA and its biological implications. Rev. Mod. Phys. 35, 724-732 (1963)). Because minor tautomers (e.g., enol or imino) are typically rare, direct evidence to support their existence has been a challenge to experimentalists. The present study, by using a battery of complementary spectroscopic tools (Singh, V. et al. Direct observation of multiple tautomers of oxythiamine and their recognition by the thiamine pyrophosphate riboswitch. ACS Chem. Biol. In Press. (2013)), has shown that KP1212, unlike canonical nucleic acid bases, existed as an ensemble of up to five tautomers in solution. The data further show that KP1212 displayed a strong propensity to exist in an enol form, rather than the classical keto form characteristic of nucleic acid bases. It is tempting to speculate that one or more members of the structural ensemble of KP1212 isomers were responsible for the mutagenic properties of the base. Nevertheless, the explicit relationship between the minor tautomers observed by spectroscopy and the mutagenic properties of KP1212 seen in the biological experiments is not immediately obvious. Proposed below is a model that attempts to correlate the mutagenic properties of KP1212 to its ability to adopt multiple tautomeric forms.

Figure 19:
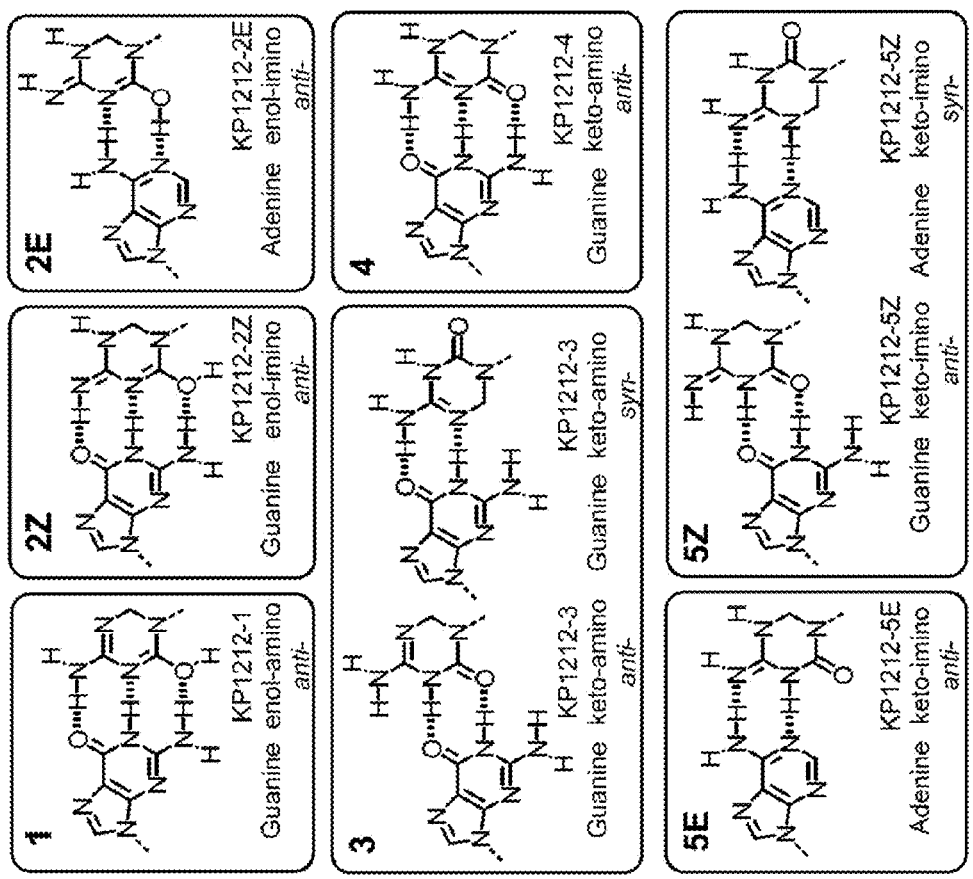
FIG. 19 shows an exemplary mechanistic model explaining the mutagenesis of KP1212 by the distinct base-pairing preferences of its different tautomers. KP1212 tautomers are paired with purine bases (G or A), by maximizing the number of possible hydrogen bonds between the bases. Tautomers 1, 2Z, 4, and 5E have a canonical Watson-Crick face and therefore are proposed to pair exclusively with either G or A. The remaining tautomers are proposed to pair either in wobble position (2E, 3, and 5Z) or involving a syn-conformer of KP1212 (3 and 5Z).

One of the fundamental assumptions in developing a mutagenesis model is that each KP1212 tautomer has a distinct base-pairing preference. To establish these preferences, in a relatively simple modeling exercise each tautomer was analyzed for its most probable base-pairing partner on the basis of hydrogen bonding. The primary criterion for correct base-pairing was formation of the maximum number of Watson-Crick type hydrogen bonds between the bases. Each type of hydrogen bond was considered to confer an equal stabilization energy. Configurations in which multiple base pairs had equal hydrogen bond numbers were considered equally probable. Since KP1212 is a cytosine (pyrimidine) analog, and the primary mutagenic events are A to G or G to A, our modeling exercise explored only purine-pyrimidine putative base pairs. Several KP1212 tautomers featured a canonical Watson-Crick face. Thus, tautomers enol-amino (1), enol-imino (2Z) and keto-amino (4) were predicted to pair with guanine, while keto-imino (5E) was predicted to pair with adenine (FIG. 19). The remaining tautomers could not adopt a canonical Watson-Crick face and therefore were hypothesized to pair in other geometries (i.e., wobble pairings, or syn-conformer pairings). FIG. 19 shows different possibilities for tautomers 2E, 3 and 5Z, which can pair with guanine (3), adenine (2E), or both (5Z).

Using the aforementioned model, the tautomeric distribution deconvoluted from the NMR data (FIGS. 14C and 14D) allows predictions to be made on the type and amount of base-pairing to be expected for KP1212. The model predicts that most of the time KP1212 would pair with G, which corresponded to the cumulative proportion of tautomers 1, 2Z, 3 and 4. Because KP1212 was also present as tautomers 2E or 5E, the model predicts it can also pair with A. Additionally, tautomer 5Z can pair with either G or A. The relative distribution of tautomers deconvoluted from the NMR spectra did not provide quantitative information on the relative ratios between the cis/trans imine geometric isomers (i.e., 2Z & 2E or 5E and 5Z). Therefore, it was not possible to estimate precisely how often KP1212 pairs with G vs. A. However, if the additional assumption were made that the imine geometric isomers were present in equal proportions (i.e., their free energies were similar), then the model predicts that KP1212 would pair ~80% of the time with G, and ~20% of the time with A. These numbers are reasonably in accord with the experimentally observed mutagenic properties of KP1212 (FIGS. 18C and 18E), correctly predicting that: 1) the dominant base-pairing partner of KP1212 is guanine; and, 2) KP1212 can also pair with adenine, at a lower frequency.

The model presented above assumes that genetic information corruption induced by KP1212 is due to the tautomerism and/or syn-anti rotamerism. However, other chemical properties, such as ionization and anomerization, could also contribute to the mutagenic properties of a nucleoside analog. The formation of ionized base pairs has been proposed to account for the mutagenicity of 5-fluro-uracil (Bonnac, L. F., Mansky, L. M. & Patterson, S. E. Structure-activity relationships and design of viral mutagens and application to lethal mutagenesis. J. Med. Chem. 2013 Dec. 12; 56(23):9403-14). The telltale sign of the involvement of ionized base pairs is a pH dependence of mutagenicity. In preliminary studies using an in vitro polymerase extension reaction, the mispairing frequency of KP1212 did not vary significantly over a small pH range (pH 7.0 and 7.8). However, further work is needed to establish the extent (if any) to which ionized base-pairs contribute to the mutagenicity of KP1212. The other mechanism that may contribute to mutagenesis involves the anomerization of the sugar portion of the nucleoside, generating an alpha-anomer (Matoušová, M. et al. 2'-deoxy-5,6-dihydro-5-azacytidine—a less toxic alternative of 2'-deoxy-5-azacytidine: a comparative study of hypomethylating potential. Epigenetics 6, 769-776 (2011)). The presence of the alpha-anomer of the KP1212 nucleoside, however, was ruled out from $^1$H and $^{13}$C NMR studies (Tables 5 and 6).

TABLE 5

$^1$H chemical shift assignments of KP1212 in DMF-$d_7$ at 20° C.

| $^1$H Position | $^1$H Chemical Shift in DMF-$d_7$ | $^1$H Peak Multiplicity and Coupling Constant (J in Hz) |
|---|---|---|
| 6 a | 4.57 | Quartet, J = 11.5, 2.0 |
| 6 b | 4.57 | Quartet, J = 11.5, 2.0 |
| 1' | 6.27 | Triplet, J = 7.3 |
| 2' a | 2.15 | Multiplet |
| 2' b | 1.87 | Multiplet |
| 3' | 4.26 | Singlet (br) |
| 3'-OH | 5.20 | Singlet (br) |
| 4' | 3.71 | Multiplet |
| 5' a | 3.57 | Singlet (br) |
| 5' b | 3.57 | Singlet (br) |
| 5'-OH | 4.91 | Singlet (br) |
| HOD in DMF | 3.53 | Singlet (br) |
| DMF (aldehyde) | 8.03 | Singlet |
| DMF (methyl a) | 2.92 | Quintet |
| DMF (methyl b) | 2.75 | Quintet |

TABLE 6

$^{13}$C chemical shift assignments of KP1212 in DMF-$d_7$ at 20° C.

| $^{13}$C Position | $^{13}$C Chemical Shift in DMF | $^{13}$C Chemical Shift in D$_2$O |
|---|---|---|
| 2 | N/A | 161.84 (from HMBC) |
| 4 | N/A | 160.91 (from HMBC) |
| 6 | N/A | 52.30 (from HSQC) |
| 1' | 83.20 (from HSQC) | 85.11 |
| 2' | 37.06 | 36.48 |
| 3' | 72.41 | 72.41 |
| 4' | 87.39 | 86.31 |
| 5' | 63.63 | 63.11 |
| DMF (aldehyde) | 163.15 | |
| DMF (methyl a) | 35.65 | |
| DMF (methyl b) | 30.52 | |

TABLE 7

Chemical shifts, areas, and assignments of the active protons on the nucleobase part of KP1212 in DMF-$d_7$ at −50° C.

| Peak | Chemical Shift (ppm) | Simulated area | Assignment | Calculated area | Difference |
|---|---|---|---|---|---|
| i | 11.44 (imino + amido) | 0.41 | 2e + 5n + 5m + 3g | 0.41 | 0.00 |
| ii | 8.43 (enol) | 0.38 | 2d | 0.38 | 0.00 |
| iii | 8.06 (enol) | 0.51 | 1c | 0.51 | 0.00 |

TABLE 7-continued

Chemical shifts, areas, and assignments of the active protons on the nucleobase part of KP1212 in DMF-$d_7$ at $-50°$ C.

| Peak | Chemical Shift (ppm) | Simulated area | Assignment | Calculated area | Difference |
|---|---|---|---|---|---|
| iv | 7.43 (amino) | 0.40 | 2f + 3h | 0.40 | 0.00 |
| v | 7.08 (amino) | 0.63 | 1a + 4l + 5o + 3i | 0.62 | −0.01 |
| vi | 6.48 (amino) | 0.67 | 1b + 4j + 4k | 0.68 | +0.01 |

The genetic and spectroscopic results presented here complement earlier biochemical work by Anderson and coworkers who performed a detailed analysis of the kinetics of pairing of KP1212 by HIV RT, DNA polymerase γ and DNA polymerase β (Murakami, E., Basavapathruni, A., Bradley, W. D. & Anderson, K. S. Mechanism of action of a novel viral mutagenic covert nucleotide: molecular interactions with HW-1 reverse transcriptase and host cell DNA polymerases. Antiviral Res. 67, 10-17 (2005)). Using single turnover methods, they observed that the quantitative features of KP1212 pairing with opposing bases is very polymerase dependent. It is difficult to extrapolate their data to ours but some observations are noteworthy. They predict a mutation rate that is five-fold or more lower than what was observed here, but this result seems reasonable given the differences in the systems used (e.g., they provided pre-steady-state and single turnover kinetic constants, whereas what was looked at here is the end product under steady-state conditions in the presence of all four dNTPs; moreover, some of the present studies were carried out in living cells, whereas their study was performed in vitro). Nevertheless, their data, as the data here, predict pairing of KP1212 with both G and A, with pairing with G being the favored event.

A recent theoretical analysis of lethal mutagenesis applied to HIV predicts that a 2-6 fold enhancement in mutation rate will result in error catastrophe and population collapse (Tripathi, K., Balagam, R., Vishnoi, N. K. & Dixit, N. M. Stochastic simulations suggest that HIV-1 survives close to its error threshold. PLoS Comput. Biol. 8, e1002684 (2012)). These data are in accord with more experimental predictions by Loeb and Harris (Loeb, L. A. et al. Lethal mutagenesis of HIV with mutagenic nucleoside analogs. Proc. Natl. Acad. Sci. U.S.A. 96, 1492-1497 (1999); Harris, K. S., Brabant, W., Styrchak, S., Gall, A. & Daifuku, R. KP-1212/1461, a nucleoside designed for the treatment of HIV by viral mutagenesis. Antiviral Res. 67, 1-9 (2005)). In this context, how does the 10% mutation frequency of KP1212 measured in the current study relates to the viral population collapse observed in biological systems? One necessary assumption is that the 10% mutation frequency observed in vitro and in vivo in this study would also apply to a system in which HIV reverse transcriptase (RT) was the replication system. When HIV RT replicates the HIV genome, it introduces about 1 error in $10^4$ bases replicated, or 1 error per genome (the HIV genome is 9749 bases long). The net increase in the viral mutation frequency due to KP1212 will depend not only on its intrinsic mutagenicity (10%), but also on how many KP1212 bases get incorporated every replication cycle. Given that each KP1212 has a 10% chance of miscoding, for every ten KP1212s present in the HIV genome, on average 1 additional mutation per replication cycle will be introduced, which corresponds to a 2 fold increase in the viral mutation frequency. Therefore, to achieve a 2-6 fold increase in mutation frequency, HIV RT needs to introduce 1-5 additional mutations, which can be achieved by incorporating 10-50 KP1212s every replication round.

The number of KP1212 bases incorporated depends on the concentration of the KP1212 triphosphate, relative to the concentration of dCTP (KP1212 is a deoxycytidine analog) in the dNTP pool, and the relative catalytic efficiency of the viral polymerase to incorporate KP1212 relative to dCTP. Kinetic data of Anderson show that HIV RT is 15 times more efficient ($k_{cat}/K_M$) at incorporating dCTP over KP1212 trisphosphate (Murakami, E., Basavapathruni, A., Bradley, W. D. & Anderson, K. S. Mechanism of action of a novel viral mutagenic covert nucleotide: molecular interactions with HIV-1 reverse transcriptase and host cell DNA polymerases. Antiviral Res. 67, 10-17 (2005)). Therefore, to incorporate 10-50 KP1212s per cycle into the HIV genome, which contains about 2400 guanines (Van der Kuyl, A. C. & Berkhout, B. The biased nucleotide composition of the HIV genome: a constant factor in a highly variable virus. Retrovirology 9, 92 (2012)), the concentration of the KP1212 triphosphate should be 6-30% of that of dCTP, which corresponds (assuming an intracellular concentration of dCTP of ~10 μM (Gandhi, V. V. & Samuels, D. C. A review comparing deoxyribonucleoside triphosphate (dNTP) concentrations in the mitochondrial and cytoplasmic compartments of normal and transformed cells. Nucleosides Nucleotides Nucleic Acids 30, 317-339 (2011))) to 0.6-3.2 μM KP1212 triphosphate. Micromolar concentrations are achievable in clinical settings for nucleotide analogs, such as AZT (Rodman, J. H. et al. Systemic pharmacokinetics and cellular pharmacology of zidovudine in human immunodeficiency virus type 1-infected women and newborn infants. J. Infect. Dis. 180, 1844-1850 (1999)). This calculation in fact is an overestimate of the level of KP1212 needed to cause HIV population collapse, since it only takes into account incorporation of KP1212 coming from the nucleotide pool opposite G. The observed A to G mutations both in cell culture (Harris, K. S., Brabant, W., Styrchak, S., Gall, A. & Daifuku, R. KP-1212/1461, a nucleoside designed for the treatment of HIV by viral mutagenesis. Antiviral Res. 67, 1-9 (2005)) and clinical isolates (Mullins, J. I. et al. Mutation of HIV-1 genomes in a clinical population treated with the mutagenic nucleoside KP1461. PLoS ONE 6, e15135 (2011)) suggest that KP1212 is also incorporated opposite A. Since the HIV genome has an even higher percentage of A (35%) than G (24%) (Van der Kuyl, A. C. & Berkhout, B. The biased nucleotide composition of the HIV genome: a constant factor in a highly variable virus. Retrovirology 9, 92 (2012)), the concentration of KP1212 needed to achieve the 2-6 fold increase in the mutation rate of HIV should be even lower than the range estimated above (0.6-3.2 μM). While the 10% mutation frequency of KP1212 is sufficient to induce HIV population collapse in cell culture experiments, if one were to design a better lethal mutagen, what would its theoretically maximum mutation frequency be? This value will depend on the number of possible base-pairing partners of the candidate lethal mutagen. If a pool nucleotide can pair only with two partners (e.g., A and G, using KP1212 as an example), it would be maximally mutagenic when it can pair with A half of the time and with G half of the time. Its mutation frequency would be 50%. Similarly, if a nucleotide has three pairing possibilities, it could achieve a mutation frequency of 67%, and if it has four (the maximum) pairing partners, its maximal mutation frequency would be 75%. KP1212 pairs only with two partners and has a mutation frequency measured at 10%, so, by the criteria described above, it is still five-fold away from the theoretical maximum mutation rate. The experimental system developed here provides an approach whereby one can assess, in quantitative terms, the proximity of any future antiviral mutagenic candidate to the theoretically maximum mutation rate.

Stepping back, the lethally mutagenic power of a pool nucleotide derives from several factors (FIG. 13B): (1) the likelihood that its nucleoside precursor will appear in the bloodstream and penetrate target cells, (2) its efficient conversion to the triphosphate form, which must be acceptable to the polymerase of the targeted system (e.g., HIV RT; and, of course the nucleotide ideally should be unacceptable to the host polymerases to avoid off-target effects), (3) the likelihood that the molecule will diversify in solution into ambiguously pairing forms (e.g., enol tautomers, imine tautomers, syn-anti rotamers, etc.), (4) the presence of ambiguously pairing forms of the lethal mutagen in the active site of a polymerase, (5) the actual formation of promiscuous base pairs in the active site, and (6) avoidance of polymerase proofreading, enzymatic repair and recombination to suppress mutations. While complex, it is useful to break the overall problem down to discrete steps in order to evaluate each from the experimental standpoint. This work addressed, among other things, steps that involved the diversification of the candidate lethal mutagen in solution and the ability of the diversified mutagen population to cause mutations in vitro and in vivo.

In summary, this study utilized, among other things, in concert a slate of synthetic, spectroscopic, and genetic methods to investigate how a candidate antiviral agent achieved its mutagenic mechanism of action. The discovery of multiple tautomeric forms of KP1212 in solution presents opportunities, through the synthesis of new analogs, for rationally reprogramming the genetic landscapes of replicating organisms. The toolset described herein could be applied to advance the development of other tautomerizable/rotamerizable nucleosides that could be used to elevate the inherent mutation rates of other fast-mutating viruses, such as those of the hepatitis C, influenza, and Dengue families, above the error catastrophe limit.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating a viral infection in a subject in need thereof, the method comprising administering to the subject a therapeutically effective amount of a pharmaceutical composition comprising:

a compound of the formula:

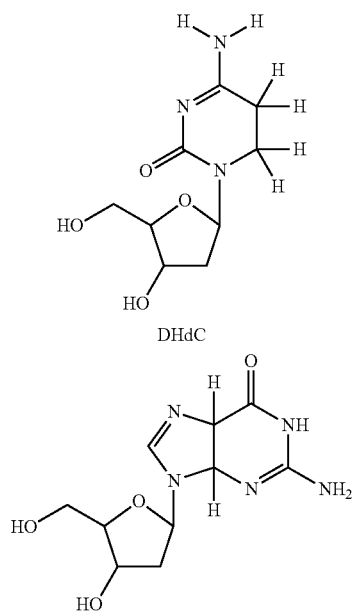

DHdC

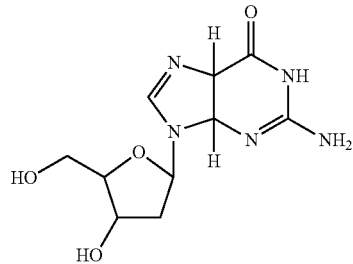

4,5-DHdG

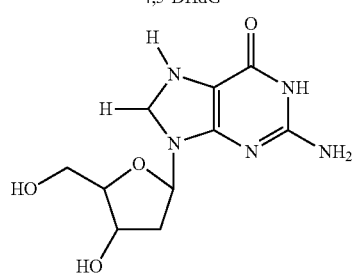

7,8-DHdG

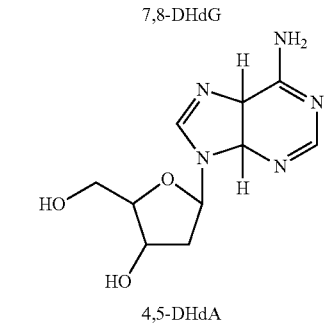

4,5-DHdA

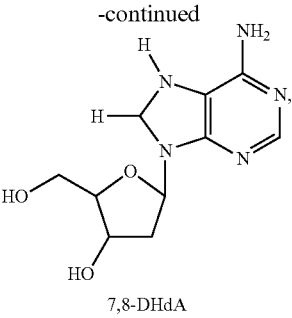

7,8-DHdA or a pharmaceutically acceptable salt thereof; and
optionally a pharmaceutically acceptable excipient.

2. The method of claim 1, wherein the viral infection is human immunodeficiency virus (HIV) infection, hepatitis C virus infection, respiratory syncytial virus (RSV) infection, Lassa fever virus infection, or poliovirus infection.

3. The method of claim 1 or 2, wherein the subject is a human.

4. The method of claim 1, wherein the pharmaceutical composition further comprises an additional pharmaceutical agent.

5. The method of claim 4, wherein the additional pharmaceutical agent is an antiviral agent.

6. A method of increasing the mutation rate of a RNA of a virus, the method comprising contacting the virus with an effective amount of a pharmaceutical composition comprising:

a compound of the formula:

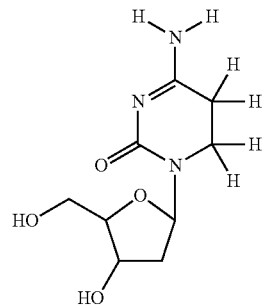

DHdC

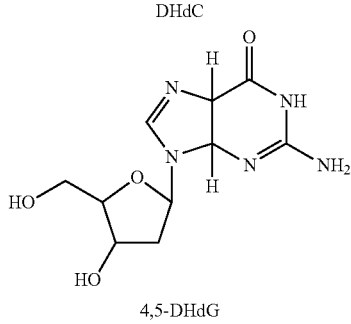

4,5-DHdG

-continued

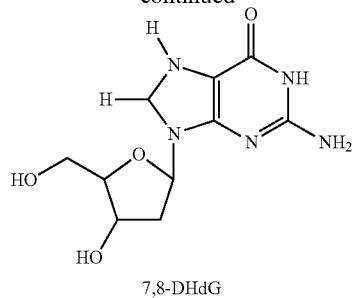
7,8-DHdG

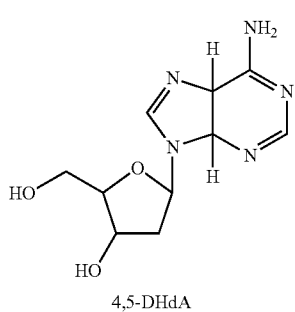
4,5-DHdA

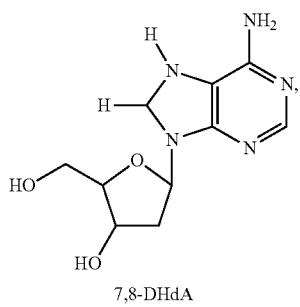
7,8-DHdA or a pharmaceutically acceptable salt thereof;
and optionally a pharmaceutically acceptable excipient;
and optionally an additional pharmaceutical agent.

7. A method of killing a virus, the method comprising contacting the virus with an effective amount of a pharmaceutical composition comprising:
a compound of the formula:

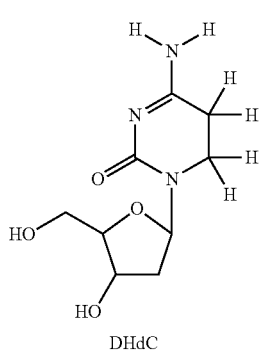
DHdC

-continued

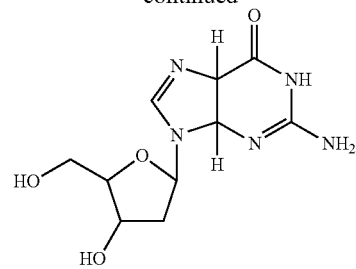
4,5-DHdG

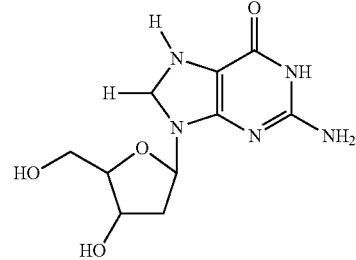
7,8-DHdG

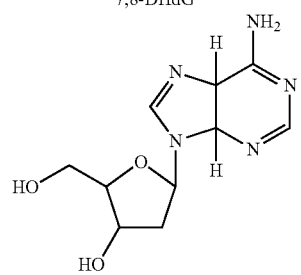
4,5-DHdA

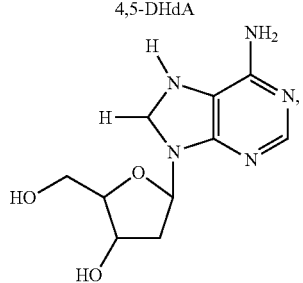
7,8-DHdA or a pharmaceutically acceptable salt thereof;
and optionally a pharmaceutically acceptable excipient;
and optionally an additional pharmaceutical agent.

8. A method of inhibiting replication of a virus, the method comprising contacting the virus with an effective amount of a pharmaceutical composition comprising:
a compound of the formula:

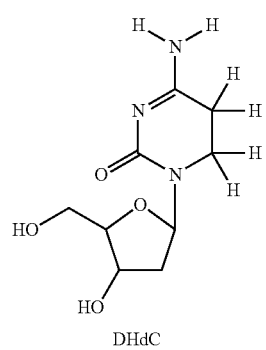
DHdC

-continued

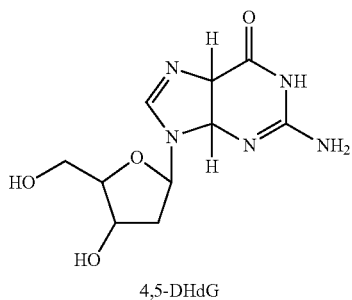

4,5-DHdG

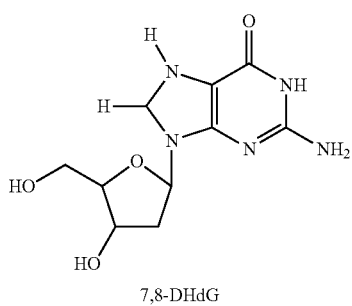

7,8-DHdG

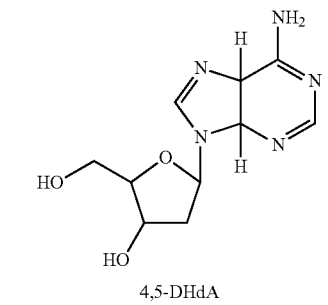

4,5-DHdA

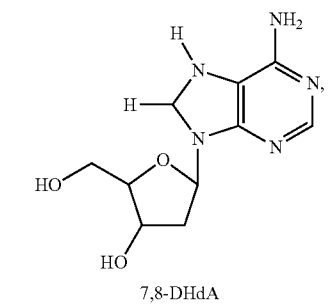

7,8-DHdA or a pharmaceutically acceptable salt thereof;
and optionally a pharmaceutically acceptable excipient;
and optionally an additional pharmaceutical agent.

9. The method of any one of claims 6, 7, and 8, wherein the virus is human immunodeficiency virus (HIV), hepatitis C virus, respiratory syncytial virus (RSV), Lassa fever virus, or poliovirus.

10. A method of increasing the mutation rate of a DNA of a virus, the method comprising contacting the virus with an effective amount of a pharmaceutical composition comprising:
a compound of the formula:

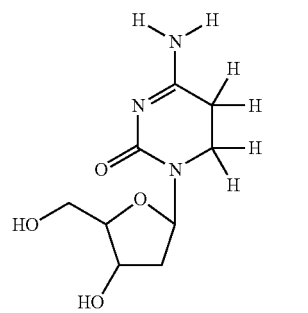

DHdC

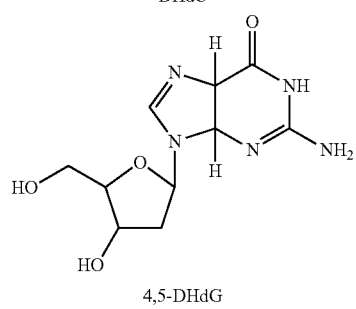

4,5-DHdG

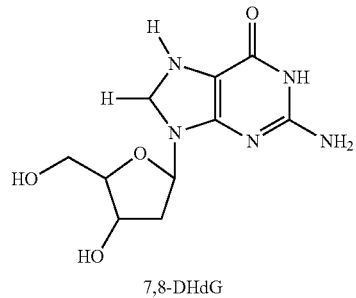

7,8-DHdG

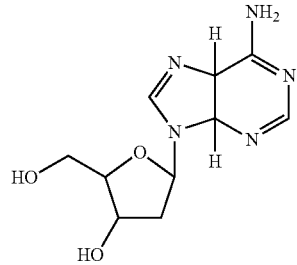

4,5-DHdA

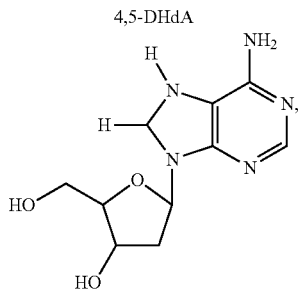

7,8-DHdA or a pharmaceutically acceptable salt thereof;
and optionally a pharmaceutically acceptable excipient;
and optionally an additional pharmaceutical agent.

* * * * *

SEQUENCE LISTING

```
<160> NUMBER OF SEQ ID NOS: 7

<210> SEQ ID NO 1
<211> LENGTH: 16
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is KP1212, 3-methylcytosine, a, c, g, or t
```

<400> SEQUENCE: 1
gaagacctng gcgtcc                                                      16

<210> SEQ ID NO 2
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 2
gaagacctgg tagcgcagg                                                   19

<210> SEQ ID NO 3
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 3
ggtcttccac tgaatcatgg tcatac                                           26

<210> SEQ ID NO 4
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 4
aaaacgacgg ccagtgaatt ggacgc                                           26

<210> SEQ ID NO 5
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is an an aminoethoxyethyl ether group

<400> SEQUENCE: 5
ncagctatga ccatgattca gtggaagac                                        29

<210> SEQ ID NO 6
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is an an aminoethoxyethyl ether group

<400> SEQUENCE: 6
ncagggtttt cccagtcacg acgttgtaa                                        29

<210> SEQ ID NO 7
<211> LENGTH: 29
<212> TYPE: DNA
<213> ORGANISM: Artificial Sequence
<220> FEATURE:
<223> OTHER INFORMATION: Synthetic Oligonucleotide

```
<220> FEATURE:
<221> NAME/KEY: misc_feature
<222> LOCATION: (1)..(1)
<223> OTHER INFORMATION: n is an an aminoethoxyethyl ether group

<400> SEQUENCE: 7
ntgtaaaacg acggccagtg aattggacg                                    29
```